US011788138B2

(12) United States Patent
Drmanac et al.

(10) Patent No.: US 11,788,138 B2
(45) Date of Patent: *Oct. 17, 2023

(54) NUCLEIC ACID SEQUENCING USING AFFINITY REAGENTS

(71) Applicants: MGI Tech Co., Ltd., Shenzhen (CN); BGI Shenzhen, Shenzhen (CN)

(72) Inventors: Radoje Drmanac, Los Altos Hills, CA (US); Snezana Drmanac, Los Altos Hills, CA (US); Handong Li, San Jose, CA (US); Xun Xu, Shenzhen (CN); Matthew J. Callow, Redwood City, CA (US); Leon Eckhardt, Soquel, CA (US); Naibo Yang, Burlingame, CA (US)

(73) Assignees: MGI Tech Co., Ltd., Shenzhen (CN); BGI Shenzhen, Shenzhen (CN)

( * ) Notice: Subject to any disclaimer, the term of this patent is extended or adjusted under 35 U.S.C. 154(b) by 92 days.

This patent is subject to a terminal disclaimer.

(21) Appl. No.: 17/084,482

(22) Filed: Oct. 29, 2020

(65) Prior Publication Data

US 2021/0254150 A1 Aug. 19, 2021

Related U.S. Application Data

(63) Continuation of application No. 15/862,566, filed on Jan. 4, 2018, now Pat. No. 10,851,410.

(60) Provisional application No. 62/490,511, filed on Apr. 26, 2017, provisional application No. 62/442,263, filed on Jan. 4, 2017.

(51) Int. Cl.
| | |
|---|---|
| *C12P 19/34* | (2006.01) |
| *C12Q 1/6874* | (2018.01) |
| *C12Q 1/6876* | (2018.01) |
| *C07K 16/44* | (2006.01) |
| *C12Q 1/6804* | (2018.01) |
| *A61K 47/00* | (2006.01) |
| *C12Q 1/6869* | (2018.01) |
| *C07K 16/28* | (2006.01) |

(52) U.S. Cl.
CPC ............ *C12Q 1/6874* (2013.01); *A61K 47/00* (2013.01); *C07K 16/2851* (2013.01); *C07K 16/44* (2013.01); *C12Q 1/6804* (2013.01); *C12Q 1/6869* (2013.01); *C12Q 1/6876* (2013.01); *C07K 2317/73* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 5,053,336 A | 10/1991 | Vanderlaan et al. | |
| 6,664,079 B2 | 12/2003 | Ju et al. | |
| 10,851,410 B2 | 12/2020 | Drmanac et al. | |
| 2003/0104460 A1 | 6/2003 | Rabbani et al. | |
| 2004/0157230 A1 | 8/2004 | Kallander et al. | |
| 2005/0130270 A1 | 6/2005 | Cupo et al. | |
| 2011/0118142 A1 | 5/2011 | Clarke et al. | |
| 2014/0242579 A1 | 8/2014 | Zhou et al. | |
| 2018/0044727 A1 | 2/2018 | Vijayan et al. | |
| 2018/0223358 A1 | 8/2018 | Drmanac et al. | |

FOREIGN PATENT DOCUMENTS

| | | |
|---|---|---|
| CN | 1297058 A | 5/2001 |
| CN | 104448001 | 3/2015 |
| WO | 2002103039 | 12/2002 |
| WO | 2003003014 | 1/2003 |
| WO | 03073088 | 9/2003 |
| WO | 2013044018 | 3/2013 |
| WO | 2014114665 | 7/2014 |
| WO | 2016065248 | 4/2016 |
| WO | 2017185026 | 10/2017 |
| WO | 2018129214 | 7/2018 |

OTHER PUBLICATIONS

U.S. Appl. No. 15/862,566, Non-Final Office Action dated Dec. 16, 2019, 6 pages.
U.S. Appl. No. 15/862,566, Notice of Allowance dated Jul. 29, 2020, 9 pages.
Australian Application No. 2018205472, First Examination Report dated Dec. 7, 2021, 3 pages.
European Application No. 18736171.2, Notice of Decision to Grant dated Apr. 29, 2022, 2 pages.
European Application No. 18736171.2, Office Action dated May 31, 2021, 3 pages.
Japanese Application No. 2019-536551, Office Action dated Jul. 13, 2021, 4 pages (1 page of English translation).
Japanese Application No. 2019-536551, Office Action dated Feb. 9, 2021, 8 pages (5 pages of English translation).
Korean Application No. 10-2019-7022620, Notice of Decision to Grant dated Oct. 25, 2021, 4 pages 4 pages (1 page of English translation).
International Application No. PCT/US2019/060779, International Preliminary Report on Patentability dated May 20, 2021, 15 pages.
Földesi et al., The Fluoride Cleavable 2-(Cyanoethoxy) Methyl (CEM) Group as Reversible 3′-O-Terminator for DNA Sequencing-by-Synthesis-Synthesis, Incorporation, and Cleavage, Nucleosides, Nucleotides & Nucleic Acids, vol. 26, No. 3, 2007, pp. 271-275.
Guo et al., Four-Color DNA Sequencing With 3′-O-Modified Nucleotide Reversible Terminators and Chemically Cleavable Fluorescent Dideoxynucleotides, Proceedings of the National Academy of Sciences, vol. 105, No. 27, Jul. 8, 2008, pp. 9145-9150.

(Continued)

*Primary Examiner* — Kenneth R Horlick
(74) *Attorney, Agent, or Firm* — Kilpatrick Townsend & Stockton LLP

(57) ABSTRACT

The invention provides compositions and methods for sequencing nucleic acids and other applications. In sequencing by synthesis, unlabeled reversible terminators are incorporated by a polymerase in each cycle, then labeled after incorporation by binding to the reversible terminator a directly or indirectly labeled antibody or other affinity reagent.

47 Claims, 17 Drawing Sheets

(56) References Cited

OTHER PUBLICATIONS

Hutter et al., Labeled Nucleoside Triphosphates with Reversibly Terminating Aminoalkoxyl Groups, Nucleosides, Nucleotides and Nucleic Acids, vol. 29, Nos. 11-12, Nov. 2010, pp. 879-895.
Knapp et al., Fluoride-Cleavable, Fluorescently Labelled Reversible Terminators: Synthesis and Use in Primer Extension, Chemistry—A European Journal, vol. 17, No. 10, Mar. 1, 2011, pp. 2903-2915.
Application EP18736171.2 , "Extended European Search Report", dated Oct. 6, 2020, 5 pages.
Feederle et al., "Antibodies Specific for Nucleic Acid Modifications", Ribonucleic Acid, vol. 14 No. 9, 2017, pp. 1089-1098.
Gonchoroff et al., "A Monoclonal Antibody Reactive With 5-Bromo-2-Deoxyuridine That Does Not Require DNA Denaturation", Cytometry, vol. 6, No. 6, 1985, pp. 506-512.
Johnston et al., "Antibody-Nucleic Acid Interactions. Monoclonal Antibodies Define Different Antigenic Domains in 2',5'-Oligoadenylates", Biochemistry, vol. 24, 1985, pp. 4710-4718.
Khan et al., "Antibodies Specific to a Deoxyribodinucleotide Sequence", Nucleic Acids Research, vol. 4, No. 9, 1977, pp. 2997-3006.
Munns et al., "Antibody Nucleic Acid Complexes. Lmmunospecific Retention of N6-Methyladenosinecontaining Transfer Ribonucleic Acid.", Biochemistry, vol. 17, No. 13, 1978, pp. 2573-2578.
Munns et al., "Characterization of Antibodies Specific for N6-methyladenosine and for 7-Methylguanosine", Biochemistry, vol. 16, No. 10, 1977, pp. 2163-2168.
Application PCT/US2018/012425 , "International Preliminary Report on Patentability", dated Jul. 18, 2019, 12 pages.
Application PCT/US2018/012425 , "International Search Report and Written Opinion", dated Mar. 26, 2018, 15 pages.
Application PCT/US2019/060779 , "International Search Report and Written Opinion", dated Apr. 23, 2020, 20 pages.
Application PCT/US2019/060779 , "Invitation to Pay Additional Fees and, Where Applicable, Protest Fee", dated Feb. 10, 2020, 3 pages.
Reynaud et al., "Monitoring of Urinary Excretion of Modified Nucleosides in Cancer Patients Using a Set of Six Monoclonal Antibodies", Cancer Letters, 1991, pp. 255-262.
Vold , "Preparation and Specificity of Antibodies Directed Tow a Rd the Ri Base Methylated Nucleotide, 2'-0-Methylguanosine 5'-monophosphate", Biochimica et Biophysica Acta, vol. 655, 1981, pp. 265-267.
Application No. EP22174722.3 , Extended European Search Report, dated Nov. 17, 2022, 7 pages.
Steemers et al., "Whole-Genome Genotyping with the Single-Base Extension Assay", Nature Methods, vol. 3, No. 1, Jan. 2006, pp. 31-33.
Chen et al., "The History and Advances of Reversible Terminators Used in New Generations of Sequencing Technology", Genomics Proteomics Bioinformatics, vol. 11, No. 1, Feb. 1, 2013, pp. 34-40.
European Application No. 18736171.2, Communication of Notice of Opposition dated Mar. 2, 2023, enclosing Notice of Opposition filed Feb. 23, 2023, 48 pages.
Munns et al., "Antibodies Specific for Modified Nucleosides: an Immunochemical Approach for the Isolation and Characterization of Nucleic Acids", Progress in Nucleic Acid Research and Molecular Biology, vol. 24, 1980, pp. 109-165.

NUCLEIC ACID SEQUENCING USING AFFINITY REAGENTS

CROSS-REFERENCE TO RELATED APPLICATIONS

This application claims priority to and is a Continuation of application Ser. No. 15/862,566 filed Jan. 4, 2018, now U.S. Pat. No. 10,851,410, which claims benefit of U.S. Provisional Application No. 62/442,263, filed Jan. 4, 2017, and U.S. Provisional Application No. 62/490,511, filed Apr. 26, 2017. The entire content of these applications is incorporated herein by reference for all purposes.

BACKGROUND OF THE INVENTION

The need for low cost, high-throughput, methods for nucleic acid sequencing and re-sequencing has led to the development "massively parallel sequencing" (MPS) technologies. One commonly used method for sequencing DNA is referred to as "sequencing-by-synthesis" (SBS), such as disclosed in Ronaghi et al., Science, 281:363-365, 1998; Li et al., Proc. Natl. Acad. Sci. USA, 100:414-419, 2003; Metzker, Nat Rev Genet. 11:31-46, 2010; Ju et al., Proc. Natl. Acad. Sci. USA 103:19635-19640, 2006; Bentley et al., Nature 456:53-59, 2008; and in U.S. Pat. Nos. 6,210,891, 6,828,100, 6,833,246, and 6,911,345, and U.S. Pat. Pub. N2016/0130647.

SBS requires the controlled (i.e., one at a time) incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. In one approach reversible terminator nucleotides (RTs) are used to determine the sequence of the DNA template. In the most commonly used SBS approach, each RT comprises a modified nucleotide that includes (1) a blocking group that ensures that only a single base can be added by a DNA polymerase enzyme to the 3' end of a growing DNA copy strand, and (2) a fluorescent label that can be detected by a camera. In the most common SBS methods, templates and sequencing primers are fixed to a solid support and the support is exposed to each of four DNA nucleotide analogs, each comprising a different fluorophore attached to the nitrogenous base by a cleavable linker, and a 3'-O-azidomethyl group at the 3'-OH position of deoxyribose, and DNA polymerase. Only the correct, complementary base anneals to the target and is subsequently incorporated at the 3' terminus of primer. Nucleotides that have not been incorporated are washed away and the solid support is imaged. TCEP (tris(2-carboxyethyl)phosphine) is introduced to cleave the linker and release the fluorophores and to remove the 3'-O-azidomethyl group, regenerating a 3'-OH. The cycle can then be repeated (Bentley et al., Nature 456, 53-59, 2008). A different fluorescent color label is used for each of the four bases, so that in each cycle of sequencing, the identity of the RT that is incorporated can be identified by its color.

Despite the widespread use of SBS, improvements are still needed. For example, current SBS methods require expensive reversibly terminated dNTPs (RTs) with a label (e.g., dye) on the base connected with a cleavable linker resulting in a) a chemical scar left on the incorporated bases after label cleavage, b) less efficient incorporation, c) quenching, d) excited dye induced termination of extension, and reducing signal in each sequencing cycle.

BRIEF SUMMARY OF THE INVENTION

The present invention relates to methods and compositions for nucleic acid analysis and sequencing. Disclosed herein is an SBS sequencing method in which the last incorporated nucleotide base is identified by binding of an affinity reagent (e.g., antibody, aptamer, affimer, knottin, etc.) that recognizes the base, the sugar, a cleavable blocking group or a combination of these components in the last incorporated nucleotide. The binding is directly or indirectly associated with production of a detectable signal.

According to one embodiment, the invention provides methods of sequencing that employ non-labeled reversible terminator (NLRT) nucleotides. A reversible terminator (RT) nucleotide is a modified deoxynucleotide triphosphate (dNTP) or dNTP analog that contains a removable blocking group that ensures that only a single base can be added by a DNA polymerase enzyme to the 3' end of a growing DNA copy strand. As is well known, the incorporation of a dNTP (2'-deoxynucleoside triphosphates) to the 3' end of the growing strand during DNA synthesis involves the release of pyrophosphate, and when a dNTP is incorporated into a DNA strand the incorporated portion is a nucleotide monophosphate (or more precisely, a nucleotide monomer linked by phosphodiester bond(s) to one or two adjacent nucleotide monomers). A reversible terminator (RT) nucleotide is a modified deoxynucleotide triphosphate (dNTP) or dNTP analog that contains a removable blocking group that ensures that only a single base can be added by a DNA polymerase enzyme to the 3' end of a growing DNA copy strand. A non-labeled RT nucleotide does not contain a detectable label. In each cycle of sequencing, the nucleotide or nucleotide analogue is incorporated by a polymerase, extending the 3' end of the DNA copy strand by one base, and unincorporated nucleotides or nucleotide analogues are washed away. An affinity reagent is introduced that specifically recognizes and binds to an epitope(s) of the newly incorporated nucleotides or nucleotide analog. After an image is taken, the blocking group and the labeled affinity reagent are removed from the DNA, allowing the next cycle of sequencing to begin. In some embodiments the epitope recognized by the affinity reagent is formed by the incorporated nucleoside itself (that is, the base plus sugar) or the nucleoside and 3' blocking group. In some embodiments the epitope recognized by the affinity reagent is formed by the reversible terminator itself, the reversible terminator in combination with the deoxyribose, or the reversible terminator in combination with the nucleobase or nucleobase and deoxyribose.

According to one such embodiment, the present invention provides methods for sequencing a nucleic acid, comprising: (a) contacting a nucleic acid template comprising the nucleic acid, a nucleic acid primer complementary to a portion of said template, a polymerase, and an unlabeled RT of Formula I:

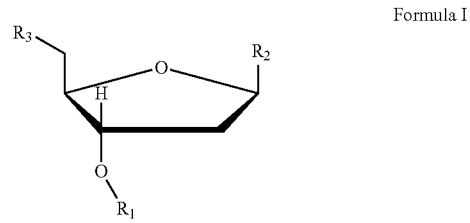

Formula I wherein: $R_1$ is a 3'-O reversible blocking group; $R_2$ is a nucleobase selected from adenine (A), cytosine (C), guanine (G), thymine (T), and analogues thereof; and $R_3$ comprises or consists of one or more phosphates; under conditions wherein the primer is extended to incorporate the unlabeled RT into a sequence complementary to the nucleic acid template, thereby producing an unlabeled extension product comprising the incorporated RT; (b) contacting the unlabeled extension product with an affinity reagent under conditions wherein the affinity reagent binds specifically to the incorporated RT to produce a labeled extension product comprising the RT; (c) detecting the binding of the affinity reagent, and (d) identifying the nucleotide incorporated into the labeled extension product to identify at least a portion of the sequence of said extension product, and therefor of the template nucleic acid.

In dNTP analogs commonly used for sequencing by synthesis, the nucleobase is conjugated to a cleavable linker that connects the base to a detectable label such as a fluorophore. See, e.g., US Pat. Pub. 2002/0227131. In contrast, in the dNTP analogs of the present invention generally $R_2$ is not a nucleobase conjugated to a dye or other detectable label by a linker.

According to another embodiment, such a method further comprises (d) removing the reversible blocking group from the RT to produce a 3'-OH; and (e) removing the affinity reagent from the RT.

According to another embodiment, such a method further comprises repeating steps of the method one or more times, that is, performing multiple cycles of sequencing, wherein at least a portion of the sequence of said nucleic acid template is determined.

According to another embodiment, such a method comprises removing the reversible blocking group and the affinity reagent in the same reaction.

According to another embodiment, such a method comprises removing the affinity reagent(s) without removing the reversible blocking group(s) and re-probing with difference affinity reagents.

In such methods, the affinity reagent may include antibodies (including binding fragments of antibodies, single chain antibodies, bispecific antibodies, and the like), aptamers, knottins, affimers, or any other known agent that binds an incorporated NLRT with a suitable specificity and affinity. In one embodiment, the affinity reagent is an antibody. In another embodiment, the affinity reagent is an antibody comprising detectable label that is a fluorescent label.

According to an embodiment, $R_1$ is selected from the group consisting of allyl, azidomethyl, aminoalkoxyl, 2-cyanoethyl, substituted alkyl, unsubstituted alkyl, substituted alkenyl, unsubstituted alkenyl, substituted alkynyl, unsubstituted alkynyl, substituted heteroalkyl, unsubstituted heteroalkyl, substituted heteroalkenyl, unsubstituted heteroalkenyl, substituted heteroalkynyl, unsubstituted heteroalkynyl, allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethenyl, formimidate, formhydroxymate, vinyloethenyl, ethylenoethenyl, cyanoethylenyl, nitroethylenyl, amidoethylenyl, amino, cyanoethenyl, cyanoethyl, alkoxy, acyl, methoxymethyl, aminoxyl, carbonyl, nitrobenzyl, coumarinyl, and nitronaphthalenyl.

According to another embodiment, $R_2$ is a nucleobase selected from adenine (A), cytosine (C), guanine (G), and thymine (T).

According to another embodiment, $R_3$ consists of or comprises one or more phosphates.

The term non-labeled reversible terminator (NLRT) may refer to the triphosphate form of the nucleotide analog, or may refer to the incorporated NLRT.

According to another embodiment of the invention, methods are provided for sequencing a nucleic acid, comprising: (a) providing a DNA array comprising (i) a plurality of template DNA molecules, each template DNA molecule comprising a fragment of the nucleic acid, wherein each of said plurality of template DNA molecules is attached at a position of the array, (b) contacting the DNA array with a nucleic acid primer complementary to a portion of each of said template DNA molecules, a polymerase, and an unlabeled RT of Formula I:

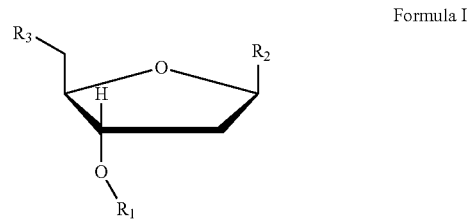

Formula I wherein: $R_1$ is a 3'-O reversible blocking group; $R_2$ is a nucleobase selected from adenine (A), cytosine (C), guanine (G), thymine (T), and analogues thereof; and $R_3$ consists of or comprises one or more phosphates; under conditions wherein the primer is extended to incorporate the unlabeled RT into a sequence complementary to at least some of said plurality of said template DNA molecules, thereby producing unlabeled extension products comprising the RT; (c) contacting the unlabeled extension products with an affinity reagent comprising a detectable label under conditions wherein the affinity reagent binds specifically to the RT to produce labeled extension products comprising the RT; and (d) identifying the RT in the labeled extension products to identify at least a portion of the sequence of said nucleic acid.

According to one embodiment of the invention, such a method comprises: (b) contacting the DNA array with a nucleic acid primer complementary to a portion of each of said template DNA molecules, a polymerase, and a set of unlabeled RTs of Formula I that comprises a first RT in which $R_2$ is A, a second RT in which $R_2$ is T, a third RT in which $R_2$ is C, and a fourth RT in which $R_2$ is G, under conditions in which the primer is extended to incorporate the unlabeled RTs into sequences complementary to at least some of said plurality of said template DNA molecules, thereby producing unlabeled extension products comprising the RTs; (c) contacting the unlabeled extension products with a set of affinity reagents under conditions in which the set of affinity reagents binds specifically to the incorporated RTs to produce labeled extension products comprising the RTs, wherein: (i) the set of affinity reagents comprises a first affinity reagent that binds specifically to the first RT, a second affinity reagent that binds specifically to the second RT, a third affinity reagent that binds specifically to the third RT, and, optionally, a fourth affinity reagent that binds specifically to the fourth RT; (ii) each of said first, second, and third affinity reagents comprises a detectable label; and (d) identifying the RTs in the labeled extension products by identifying the label of the affinity reagent bound to the RTs at their respective positions on the array to identify at least a portion (e.g., one base per cycle) of the sequence of said nucleic acid. According to a related embodiment, each of said first, second, third and fourth affinity reagents comprises a detectable label. According to another related embodiment, each of said first, second, and third affinity reagents comprises a different detectable label. According to another related embodiment, each of the first, second, and third affinity reagents comprises the same label (e.g., same fluorophore(s)) in different amounts, resulting in signals of different intensities. According to another embodiment, the affinity reagents bound to incorporated RTs are not directly labeled but are indirectly labeled using secondary affinity reagents.

According to another embodiment of the present invention, DNA arrays are provided. Such arrays comprise: a plurality of template DNA molecules, each DNA molecule attached at a position of the array, a complementary DNA sequence base-paired with a portion of the template DNA molecule at a plurality of the positions, wherein the complementary DNA sequence comprises at its 3' end an incorporated RT; and an affinity reagent attached specifically to at least some of the RTs, the affinity reagent comprising a detectable label that identifies the RT to which it is attached.

According to another embodiment of the invention, kits are provided that comprise: (a) an unlabeled RTs of Formula I:

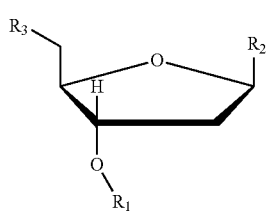

Formula I wherein: $R_1$ is a 3'-O reversible blocking group; $R_2$ is a nucleobase selected from adenine (A), cytosine (C), guanine (G), thymine (T), and analogues thereof; and $R_3$ consists of or comprises one or more phosphates; (b) a labeled affinity reagent that is binds specifically to one of the RT; and (c) packaging for the RT and the affinity reagent. According to another embodiment, such a kit comprises: a plurality of the RTs, wherein each RT comprises a different nucleobase, and a plurality of affinity reagents, wherein each affinity reagent binds specifically to one of the RTs.

BRIEF DESCRIPTION OF THE DRAWINGS

FIG. 3A 3'-O-azidomethyl-2'-deoxyguanine; FIG. 3B 3'-O-amino-2'-deoxyguanine; FIG. 3C 3'-O-cyanoethylene-2'-deoxyguanine; FIG. 3D 3'-O-phospho; FIG. 3E: 3'-ethyldisulfide-methylene-2'-deoxythymine.

In FIG. 4, "⌇" indicates the attachment point of the molecule to the remainder of the structure.

DETAILED DESCRIPTION OF THE INVENTION

1. Overview

Figure 1:
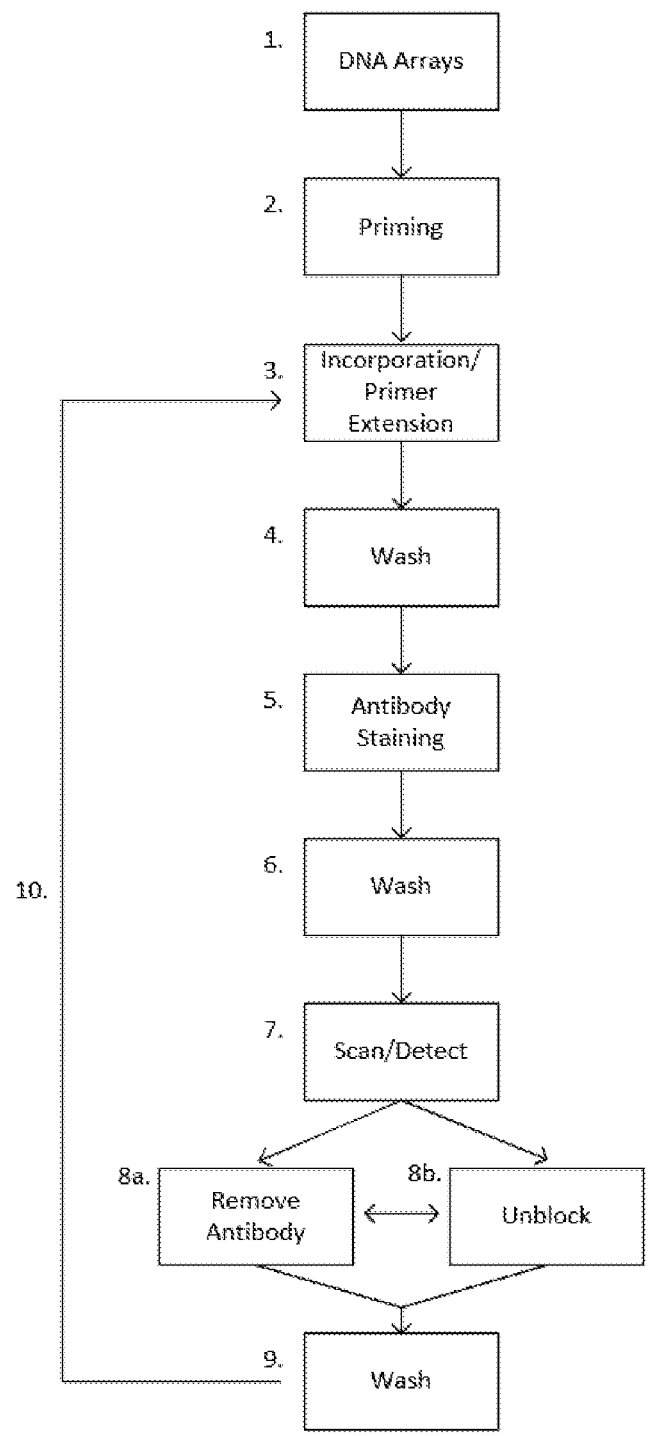
FIG. 1 is a flowchart that illustrates an example of a sequencing method of the invention.

In certain aspects, the present invention provides methods and compositions for sequencing-by-synthesis (SBS) or combinatorial probe anchor sequencing (cPAS) of nucleic acids that employ unlabeled reversible terminator nucleotides. In one approach, SBS is carried out by producing immobilized single stranded template DNAs at positions on an array. In most approaches, each immobilized single stranded template DNA is at a position with a large number of copies (e.g., amplicons) of like sequence. For example, bridge PCR may be used to generate a cluster of template sequences at a position on an array (Illumina), or rolling circle replication may be used to generate a single-stranded concatemer, or DNA nanoball (DNB), with many copies of the template sequences (Complete Genomics, Inc.). SBS is carried out by hybridizing a primer or primers to the template DNA and extending the primer to produce an extended primer, or growing DNA strand (GDS). Extending the primer refers to addition ("incorporation" or "incorporating") of nucleotides at the 3' end of the primer DNA strand while it is hybridized to the template. The nucleotide incorporated at the 3' terminus is complementary to the corresponding nucleotide of the primer such that by determining the identity of the incorporated nucleotide at each sequencing cycle the nucleotide sequence of the template may be determined.

In one prior art approach, labeled nucleotide analogs are incorporated into the GDS. Generally the labeled nucleotide analogs comprise a blocking group that insures that only a single nucleotide per step can be incorporated and a dye (typically a fluorescent dye) attached via a cleavable linker to the nucleotide. Each cycle of sequencing encompasses incorporating a labeled nucleotide analog at the end of the GDS, detecting the incorporated labeled nucleotide analog label, removing the label from the incorporated nucleotide analog, and removing the blocking group from the incorporated nucleotide analog to allow incorporation of a new labeled nucleotide analog. In contrast, the present invention does not require labeled nucleotide analogs that include a dye attached via a cleavable linker to a base or sugar.

In an alternative approach described in U.S. Pat. Pub. US2017/0240961, which is incorporated herein by reference, a nucleotide analog, when incorporated, comprises an affinity tag attached via a linker to the nucleotide. The affinity tag is one member of a specific binding pair (SBP). In one approach the affinity tag is biotin. After incorporation the incorporated nucleotide is exposed to an affinity reagent comprising the second member of the SBP (e.g., streptavidin) and a detectable label. The detectable label is detected to identify the incorporated nucleotide. Following detection, the incorporated nucleotide analog-affinity reagent complex is treated to cleave the linker and release the detectable label. In one approach the affinity tag is an antigen and the affinity reagent is a fluorescently labeled antibody that specifically binds the antigen. In contrast, the present invention does not require an affinity tag and employs, in some aspects, an affinity reagent that binds the nucleobase, sugar moiety, cleavable blocking group or a combination thereof, rather than to an affinity tag.

According to one aspect of the method disclosed herein, a non-labeled reversible terminator, i.e., a nucleotide analog that includes a reversible terminator or blocking group (Non-Labeled Reversible Terminator, or NLRT), is incorporated at the 3' terminus of the GDS, and then is exposed to an affinity reagent (e.g., antibody) that specifically binds to the incorporated NLRT (the "binding event"). After detection of the binding event, the affinity reagent is removed. In one approach a nucleotide analog comprising a reversible blocking group is incorporated at the 3' terminus of the GDS, and after detection of the binding event, the reversible blocking group and the affinity reagent are removed, optionally in the same step. In this approach, each cycle of sequencing includes: (i) incorporation of an NLRT comprising a blocking group by a DNA polymerase, followed by washing away unincorporated NLRT(s); (ii) contacting the incorporated nucleotide analog with an labeled affinity reagent that recognizes and specifically binds to the incorporated NLRT; (iii) detection of the binding of the affinity reagent; (iv) removal of the blocking group in a fashion that allows incorporation of an additional nucleotide analog (e.g., produces a hydroxyl group at the 3' position of a deoxyribose moiety), and (v) removal of the affinity reagent. This step may be followed by a new cycle or cycles in which a new nucleotide analog is incorporated and detected. The affinity reagent (e.g., antibody) may be directly labeled (e.g., a fluorescent labeled antibody) or may be detected indirectly (e.g., by binding of a labeled anti-affinity reagent secondary affinity reagent). Thus, it will be appreciated that a "labeled affinity reagent" may be directly labeled by, for example, conjugation to a fluorophore, or indirectly labeled.

In another approach a nucleotide analog comprising a reversible blocking group is incorporated at the 3' terminus of the GDS, and after detection of the binding event, the reversible blocking group and the affinity reagent are removed, In this approach, each cycle of sequencing includes: (i) incorporation of an NLRT comprising a blocking group by a DNA polymerase, optionally followed by washing away unincorporated NLRT(s); (ii) removal of the blocking group in a fashion that regenerates a hydroxyl (OH) group at the 3' positon of the deoxyribonucleotide; (iii) removing the blocking group of the allows incorporation of an additional nucleotide analog (e.g., produces a hydroxyl group at the 3' position of a deoxyribose moiety) contacting the incorporated nucleotide analog with an labeled affinity reagent that recognizes and specifically binds to the incorporated NLRT; (iii) detection of the binding of the affinity reagent; and (v) removal of the affinity reagent. This step may be followed by a new cycle or cycles in which a new nucleotide analog is incorporated and detected. The affinity reagent (e.g., antibody) may be directly labeled (e.g., a fluorescent labeled antibody) or may be detected indirectly (e.g., by binding of a labeled anti-affinity reagent secondary affinity reagent). Thus, it will be appreciated that a "labeled affinity reagent" may be directly labeled by, for example, conjugation to a fluorophore, or indirectly labeled.

SBS involves two or more cycles of primer extension in which a nucleotide is incorporated at the 3' terminus of the extended primer. The present invention makes use of affinity reagents, such as antibodies, to (i) detect the nucleotide incorporated at the 3' terminus of the extended primer ("3' terminal nucleotide") and (ii) identify the nucleobase of that 3' terminal nucleotide and distinguishing one nucleobase from another (e.g., A from G). Without intending to be bound by a specific mechanism, this is possible because each affinity reagent is designed to distinguish a 3' terminal nucleotide from other, "internal" nucleotides of the extended primer, even when the 3' terminal nucleotide and internal nucleotides comprise the same nucleobase. Each affinity reagent (or in some cases combination of affinity reagents) is also designed to detect properties of a 3' terminal nucleotide that identify the nucleobase associated with the 3' terminal nucleotide. A number of strategies, methods, and materials are provided for carrying out these and other steps. This section provides an overview in which many variations are omitted, and should not be considered limiting in any way.

In some approaches the SBS reactions of the invention are carried out using nucleotides with 3' reversible terminator moieties. In these approaches the incorporated 3' terminal nucleotide differs from the internal nucleotides based on the presence of the reversible terminator moiety. Thus, an affinity reagent that binds to a reversible terminator moiety in an extended primer is binding to (and thereby detects) the 3' terminal nucleotide, distinguishing it from internal nucleotides. In a different approach the incorporated 3' terminal nucleotide differs from the internal nucleotides based on the presence of a free 3'-OH (hydroxyl) group which is not present on internal nucleotides. Thus, an affinity reagent that binds to a free 3'-OH group in an extended primer is binding to the 3' terminal nucleotide is binding to (and thereby detects) the 3' terminal nucleotide, distinguishing it from internal nucleotides. In some approaches the free 3'-OH group is generated by cleavage of the reversible terminator in an incorporated nucleotide analog. In another approach, the free 3'-OH group results from incorporation of a nucleotide that does not comprise a reversible terminator moiety, such as a naturally occurring nucleotide. In an additional approach, combinable with either of two approaches described above, the incorporated 3' terminal nucleotide differs from the internal nucleotides based on other structural differences characteristic of a 3' terminal nucleotide including, but not limited to, greater accessibility of an affinity reagent to the deoxyribose sugar of a 3' terminal nucleotide relative to deoxyribose of internal nucleotides, greater accessibility of an affinity reagent to the nucleobase of a 3' terminal nucleotide to an affinity reagent relative to deoxyribose of internal nucleotides, and other molecular and conformational differences between the 3' terminal nucleotide and internal nucleosides.

Thus, in an aspect of the present invention, and as described in the Examples below, affinity reagents are used to detect these structural differences between the 3' terminal nucleotide of an extended primer and other nucleotides.

Also provided are a number of strategies, methods, and materials for detecting properties of the 3' terminal nucleotide that identify the nucleobase of the 3' terminal nucleotide. In one approach, naturally occurring nucleotides, or nucleotide analogs comprising naturally occurring nucleobases (e.g., A, T, C and G), are used in the sequencing reaction and incorporated into the primer extension product. Affinity reagents that specifically bind to one nucleobase (e.g., A) and distinguish that nucleobase from others to which it does not bind (e.g., T, C and G) are used to identify the nucleobase of the 3' terminal nucleotide. In another approach, nucleotide analogs comprising modified (i.e., not naturally occurring) nucleobases are used in the sequencing reaction and incorporated into the primer extension product. Affinity reagents that specifically bind to one modified nucleobase (e.g., modified A) and distinguish that modified nucleobase from other modified or natural nucleobases. An affinity reagent that specifically binds to a modified nucleobase generally recognizes the modification, such that the binding to modified nucleobases differs from binding to a naturally occurring nucleobase without the modification. For example, an affinity reagent that binds to an adenosine analog in which nitrogen at position 7 ($N^7$) is replaced by methylated carbon (see Structure XV, below) may not bind to the naturally occurring (unmodified) adenosine nucleobase, or may bind less avidly. Without intending to be bound by a particular mechanism, it is believed that an affinity reagent that specifically recognizes a modified moiety (in this case a modified nucleobase) does so by binding the modified feature (in this case, the portion of modified adenosine comprising the methylated-carbon). Stated differently, the affinity reagent binds an epitope that includes the methylated-carbon. It will be understood that the affinity reagent binds other portions of the incorporated nucleotide as well.

In yet another approach, nucleotides with 3' reversible blocking groups (reversible terminator nucleotides) are incorporated into the primer extension product. The blocking groups are removed at each sequencing cycle so that only the last incorporated nucleotide of the primer extension produce comprises a blocking group. In this approach affinity reagents that bind the blocking groups are used. In this approach, at least two nucleotide analogs (i.e., with different nucleobases) used in the sequencing reaction comprise different blocking groups. By, for illustration, using a first blocking group (e.g., 3'-O-azidomethyl) for a nucleotide comprising adenine or an adenine analog, a second, different blocking group (e.g., 3'-O-cyanoethylene) for a nucleotide comprising guanine or a guanine analog, etc., the specificity of the affinity reagent will identify the associated nucleobase. For example, extending the illustration above, if a 3' terminal nucleotide is recognized by an affinity reagent specific for 3'-O-cyanoethylene this indicates that the associated nucleobase is guanine or a guanine analog and the template base at this position is cytosine. In a variation of this approach, blocking groups that differ by only a small feature may be used, and the affinity reagent binds an epitope that includes the distinguishing small feature.

As described herein below, in one aspect of the present invention, affinity reagents that recognize and specifically bind to nucleotides or nucleotide analogs based on a combination of structural features are used (e.g., an affinity reagent that recognizes a particular blocking group and a specific nucleobase with particular modifications) are used. In this aspect, nucleotides or nucleotide analogs are designed and/or selected for the property of being recognized by a specific affinity reagent. In some cases, an affinity reagent that binds multiple structural features has the advantage of stronger and more specific affinity reagent binding. TABLE A, below, is a nonexhaustive collection of examples of structural differences that can be recognized by an affinity reagent to distinguish nucleotides having different nucleobases ($2^{nd}$ column) and the moieties in the last incorporated nucleotide that may be bound by an affinity reagent to provide enough binding efficiency and/or that distinguishes the last incorporated nucleotide from the internal nucleotides based on those features (3rd column).

TABLE A

| Affinity Reagent Class | (Specificity) Distinguishes incorporated nucleotide based on | Elements of Last Incorporated Nucleotide Bound By Affinity reagent |
|---|---|---|
| A | Differences in natural nucleobases (e.g., A, T, C, G) | 1. Nucleobase and sugar; 2. Nucleobase and blocking group; 3. Nucleobase and blocking group and sugar; |
| B | Differences in natural nucleobases along with modified features of nucleobase analogs (or "modified nucleobases") | 1. Modified features of nucleobase analogs; 2. Modified features of nucleobase analogs and sugar; 3. Natural nucleobases, modified features of nucleobase analogs, and blocking group; 4. Natural nucleobases, modified features of nucleobase analogs, and blocking group; |
| C | Differences in natural bases combined with differences in blocking groups (in at least some NLRTs) | 1. Nucleobase and variations in blocking group structure or entire blocking group; or 2. Nucleobase, variations in blocking group structure or entire blocking group and sugar; |
| D | Differences in blocking groups | 1. Different blocking groups and/or variations in similar blocking groups; 2. Different blocking groups and/or variations in similar blocking groups, nucleobase (natural or modified); or 3. Different blocking groups and/or variations in similar blocking groups, nucleobase (natural or modified) and sugar; |

TABLE A-continued

| Affinity Reagent Class | (Specificity) Distinguishes incorporated nucleotide based on | Elements of Last Incorporated Nucleotide Bound By Affinity reagent |
|---|---|---|
| E | Differences in natural nucleobases combined with specific nucleobase modifications of at least some nucleobases and differences in blocking groups of at least some NLRTs | 1. Natural nucleobases, modified features of nucleobase analogs, and blocking group; or 2. Natural nucleobases, modified features of nucleobase analogs, and blocking group and sugar. |

As discussed in detail below, the portion of the incorporated nucleotide analog to which the labeled affinity reagent binds may include, for example and not limitation, the nucleobase and the blocking group, or the nucleobase and/or the blocking group in combination with the sugar moiety of the nucleotide analog. See Table A, below. Binding of the labeled affinity reagent may depend on the position of the target nucleotide, e.g., distinguishing between a nucleotide analog having a blocking group at the 3' terminus of the GDS, and a similar nucleotide analog (lacking the blocking group) that is located within or internal to the GDS. Binding of the labeled affinity reagent also depends upon the nucleobase itself, such that the affinity reagents binds to one target NLRT (e.g., NLRT-A) incorporated at the end of a GDS at one position on an array but not to other NLRTs (e.g., NLRT-C, -T, or -G) incorporated at the end of a GDS at a different position on an array.

The present invention has advantages over other SBS methods. Removal of the labeled affinity reagent does not leave behind a chemical "scar" resulting from groups left attached to the dNTP after cleavage of a linker. This is advantageous because such "scars" may reduce the efficiency of dNTP incorporation by polymerase. In addition, in this approach the affinity reagent may include multiple fluorescent moieties and provide a stronger signal than a single fluorescent dye attached to a dNTP according to commonly used methods. This approach also may cause less photodamage, since lower excitation power or shorter exposure times may be used. The approach disclosed herein is expected to allow longer reads (e.g., reads that are longer than 500 bases, or longer than 1000 bases) and/or more accurate reads longer than 50, 100 or 200 bases, (e.g., with fewer errors than one in 2000 bases or one in 5000 bases). The compositions and methods of the present invention also may be more economical than labeled reversible terminator (RT) methods commonly used for SBS. Unlabeled RTs cost less than labeled RTs. In standard SBS using labeled RTs, high concentrations of labeled RTs are used to drive the incorporation of the RT to completion, and most of the labeled RTs (70-99% or more) are not incorporated by polymerase and are washed away. Using lower cost unlabeled RTs thus reduces this cost. Moreover, in the labeling step of the present invention, in which a labeled affinity reagent is used, it may be sufficient for only a small percentage of target templates are bound by an affinity reagent that has multiple even 30% may be enough with efficiently labeled binders with multiple molecules of label to one molecule of binder; to be labeled (e.g., about 5%, or about 10%, or less than about 15%, less than about 20%, less than about 25%, or less than about 30%) in order to obtain a sufficient signal for imaging, particularly if the affinity reagent efficiently binds to the target dNTP and comprises multiple label molecules. A higher level of binding may be preferred if the affinity reagent bears only a single label molecule (e.g., 70 percent or more).

2. Definitions and Terms

As used herein, in the context of a nucleotide analog, the terms "unlabeled" and "non-labeled" are used interchangeably.

As used herein, unless otherwise apparent from context, "nonlabled reversible terminator [nucleotide]," "NLRT," "reversible terminator nucleotide," "reversible terminator," "RT," and the like are all used to refer to a sequencing reagent comprising a nucleobase or analog, deoxyribose or analog, and a cleavable blocking group. A nonlabled reversible terminator nucleotide may refer to a dNTP (i.e., a substrate for polymerase) or a reversible terminator nucleotide incorporated to into a primer extension product, initially at the 3' terminus and, following additional incorporation cycles, if any, in an "internal" portion of the primer extension product.

As used herein, a "dNTP" includes both naturally occurring deoxyribonucleotide triphosphates and analogs thereof, including analogs with a 3'-O cleavable blocking group.

As used herein, in the context of a cleavable blocking group of a nucleotide analog, the designation 3'-O-"is sometimes implied rather than explicit. For example, the terms "azidomethyl", "3'-O-azidomethyl" are interchangeable as will be apparent from context.

"Amplicon" means the product of a polynucleotide amplification reaction, namely, a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, rolling circle amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and U.S. Pub. No. 2006/0024711).

"Antigen" as used herein means a compound that can be specifically bound by an antibody. Some antigens are immunogens (see, Janeway, et al., Immunobiology, 5th Edition, 2001, Garland Publishing). Some antigens are haptens that are recognized by an antibody but which do not elicit an immune response unless conjugated to a protein. Exemplary antigens include NLRTs, reversible terminator blocking groups, dNTPs, polypeptides, small molecules, lipids, or nucleic acids.

"Array" or "microarray" means a solid support (or collection of solid supports such as beads) having a surface, preferably but not exclusively a planar or substantially planar surface, which carries a collection of sites comprising nucleic acids such that each site of the collection is spatially defined and not overlapping with other sites of the array; that is, the sites are spatially discrete. The array or microarray can also comprise a non-planar interrogatable structure with a surface such as a bead or a well. The oligonucleotides or polynucleotides of the array may be covalently bound to the solid support, or it may be non-covalently bound. Conventional microarray technology is reviewed in, e.g., Schena, Ed. (2000), Microarrays: A Practical Approach (IRL Press, Oxford). As used herein, "random array" or "random microarray" refers to a microarray where the identity of the oligonucleotides or polynucleotides is not discernable, at least initially, from their location but may be determined by a particular biochemistry detection technique on the array. See, e.g., U.S. Pat. Nos. 6,396,995; 6,544,732; 6,401,267; and 7,070,927; PCT publications WO 2006/073504 and 2005/082098; and U.S. Pat. Pub. Nos. 2007/0207482 and 2007/0087362.

The terms "reversible," "removable," and "cleavable" in reference to a blocking group have the same meaning.

The terms "reversible blocking group," of a reversible terminator nucleotide may also be referred to as a "removable blocking group," a "cleavable linker," a "blocking moiety," a "blocking group," "reversible terminator blocking group" and the like. A reversible blocking group is a chemical moiety attached to the nucleotide sugar (e.g., deoxyribose), usually at the 3'-O position of the sugar moiety, which prevents addition of a nucleotide by a polymerase at that position. A reversible blocking group can be cleaved by an enzyme (e.g., a phosphatase or esterase), chemical reaction, heat, light, etc., to provide a hydroxyl group at the 3'-position of the nucleoside or nucleotide such that addition of a nucleotide by a polymerase may occur.

"Derivative" or "analogue" means a compound or molecule whose core structure is the same as, or closely resembles that of, a parent compound, but which has a chemical or physical modification, such as a different or additional side group, or 2' and or 3' blocking groups, which allows the derivative nucleotide or nucleoside to be linked to another molecule. For example, the base can be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate and phosphoramidate linkages. The analogs should be capable of undergoing Watson-Crick base pairing. For example, deoxyadenosine analogues include didanosine (ddl) and vidarabine, and adenosine analogues include, BCX4430; deoxycytidine analogs include cytarabine, gemcitabine, emtricitabine (FTC), lamivudine (3TC), and zalcitabine (ddC); guanosine and deoxyguanosine analogues include abacavir, aciclovir, and entecavir; thymidine and deoxythymidine analogues include stavudine (d4T), telbivudine, and zidovudine (azidothymidine, or AZT); and deoxyuridine analogues include idoxuridine and trifluridine. "Derivative", "analog" and "modified" as used herein, may be used interchangeably, and are encompassed by the terms "nucleotide" and "nucleoside" defined herein.

"Incorporate" means becoming part of a nucleic acid molecule. In SBS, incorporation of an RT occurs when a polymerase adds an RT to a growing DNA strand through the formation of a phosphodiester or modified phosphodiester bond between the 3' position of the pentose of one nucleotide, that is, the 3' nucleotide on the DNA strand, and the 5' position of the pentose on an adjacent nucleotide, that is, the RT being added to the DNA strand.

"Label," in the context of a labeled affinity reagent, means any atom or molecule that can be used to provide a detectable and/or quantifiable signal. Suitable labels include radioisotopes, fluorophores, chromophores, mass labels, electron dense particles, magnetic particles, spin labels, molecules that emit chemiluminescence, electrochemically active molecules, enzymes, cofactors, and enzyme substrates. In some embodiments, the detection label is a molecule containing a charged group (e.g., a molecule containing a cationic group or a molecule containing an anionic group), a fluorescent molecule (e.g., a fluorescent dye), a fluorogenic molecule, or a metal. Optionally, the detection label is a fluorogenic label. A fluorogenic label can be any label that is capable of emitting light when in an unquenched form (e.g., when not quenched by another agent). The fluorescent moiety emits light energy (i.e., fluoresces) at a specific emission wavelength when excited by an appropriate excitation wavelength. When the fluorescent moiety and a quencher moiety are in close proximity, light energy emitted by the fluorescent moiety is absorbed by the quencher moiety. In some embodiments, the fluorogenic dye is a fluorescein, a rhodamine, a phenoxazine, an acridine, a coumarin, or a derivative thereof. In some embodiments, the fluorogenic dye is a carboxyfluorescein. Further examples of suitable fluorogenic dyes include the fluorogenic dyes commercially available under the Alexa Fluor© product line (Life Technologies, Carlsbad, Calif.). Alternatively, non-fluorogenic labels may be used, including without limitation, redoxgenic labels, reduction tags, thio- or thiol-containing molecules, substituted or unsubstituted alkyls, fluorescent proteins, non-fluorescent dyes, and luminescent proteins.

"Nucleobase" means a nitrogenous base that can base-pair with a complementary nitrogenous base of a template nucleic acid. Exemplary nucleobases include adenine (A), cytosine (C), guanine (G), thymine (T), uracil (U), inosine (I) and derivatives of these. References to thymine herein should be understood to refer equally to uracil unless otherwise clear from context. As used herein, the terms "nucleobase," "nitrogenous base," add "base" are used interchangeably.

A "naturally occurring nucleobase," as used herein, means adenine (A), cytosine (C), guanine (G), thymine (T), or uracil (U). In some cases, naturally occurring nucleobase refers to A, C, G and T (the naturally occurring bases found in DNA).

A "nucleotide" consists of a nucleobase, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) (or in the context of RNA, uracil (U)). The C-1 atom of deoxyribose is bonded to N-1 of a pyrimidine or N-9 of a purine. A nucleotide is also a phosphate ester or a nucleoside, with esterification occurring on the hydroxyl group attached to C-5 of the sugar. Nucleotides are usually mono-, di- or triphosphates. A "nucleoside" is structurally similar to a nucleotide, but does not include the phosphate moieties. Common abbreviations include "dNTP" for deoxynucleotide triphosphate.

"Nucleic acid" means a polymer of nucleotide monomers. As used herein, the terms may refer to single- or double-stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs. Non-naturally occurring analogs may include peptide nucleic acids, locked nucleic acids, phosphorothioate internucleosidic linkages, bases containing linking groups permitting the attachment of labels, such as fluorophores, or haptens, and the like. Nucleic acids typically range in size from a few monomeric units, e.g., 5-40, when they are usually referred to as "oligonucleotides," to several hundred thousand or more monomeric units. Whenever a nucleic acid or oligonucleotide is represented by a sequence of letters (upper or lower case), such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually nucleic acids comprise the natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogs, e.g., modified bases, sugars, or internucleosidic linkages. To those skilled in the art, where an enzyme has specific oligonucleotide or nucleic acid substrate requirements for activity, e.g., single-stranded DNA, RNA/DNA duplex, or the like, then selection of appropriate composition for the oligonucleotide or nucleic acid substrates is well within the knowledge of one of ordinary skill, especially with guidance from treatises, such as Sambrook et al., Molecular Cloning, Second Edition (Cold Spring Harbor Laboratory, New York, 1989), and like references.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Polynucleotide" is used interchangeably with the term "nucleic acid" to mean DNA, RNA, and hybrid and synthetic nucleic acids and may be single-stranded or double-stranded. "Oligonucleotides" are short polynucleotides of between about 6 and about 300 nucleotides in length. "Complementary polynucleotide" refers to a polynucleotide complementary to a target nucleic acid.

"Solid support" and "support" are used interchangeably and refer to a material or group of materials having a rigid or semi-rigid surface or surfaces. Microarrays usually comprise at least one planar solid phase support, such as a glass microscope slide.

As used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and/or methods known to those skilled in the art.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publications and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

3. Nucleotides and Nucleotide Analogs

In various embodiments SBS according to the invention may use non-labeled reversible terminators ("NLRT") (e.g., a nucleotide analog with a blocking group), non-labeled naturally occurring nucleotides (e.g., dATP, dTTP, dCTP and dGTP), or non-labeled nucleotide analogs that do not include a blocking group.

3.1 Non-Labeled Reversible Terminators (NLRT)

Non-labeled reversible terminators ("NLRT") of the invention are nucleotide analogs comprising a removable blocking group at the 3'-OH position of the deoxyribose. Although numerous reversible terminators have been described, and reversible terminators are widely used in SBS, the non-labeled reversible terminators used in accord with the present invention differ from those in commercial use because they are non-labeled and because they are used in conjunction with the affinity reagents described herein below. In an aspect the NLRTs of the invention are non-labeled. In one embodiment, non-labeled means the NLRT does not comprise a fluorescent dye. In one embodiment, non-labeled means the NLRT does not comprise a chemiluminescent dye. In one embodiment, non-labeled means the NLRT does not comprise a light emitting moiety.

In some embodiments, exemplary NLRTs have Structure 1, below, prior to incorporation of the NLRT into a DNA strand.

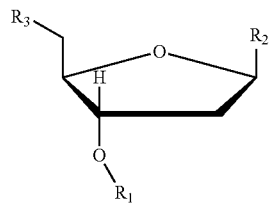

Structure I where $R_1$ is a 3'-O reversible blocking group, $R_2$ is, or includes, the nucleobase; and $R_3$ comprises at least one phosphate group or analog thereof.

Reversible blocking groups $R_1$ may be removed after incorporation of the NLRT into a DNA strand. After incorporation of the analog at the 3' terminus of a DNA strand, the removal of the blocking group results in a 3'-OH. Any reversible blocking group may be used. Exemplary reversible blocking groups are described below.

Nucleobases $R_2$ may be, for example, adenine (A), cytosine (C), guanine (G), thymine (T), uracil (U), or inosine (1) or analogs thereof. NLRTs may be referred to according to the nucleobase; for example, an NLRT that has an A nucleobase is referred to as NLRT-A. Thus, the corresponding NLRTs are referred to herein as "NLRT-A," "NLRT-C," "NLRT-G," "NLRT-T," "NLRT-U," and "NLRT-I," respectively. NLRT-T and NLRT-C may be referred to as NLRT-pyrimidines. NLRT-G and NLRT-A may be referred to as NLRT-purines.

Nucleobase $R_2$ may be any nucleobase or nucleobase analog (e.g., an analog of adenine, cytosine, guanine, thymine, uracil, or inosine). For example, a modification to the naturally occurring nucleobase may be made to increase the immune response to the analog when raising antibodies, or to increase the specificity of the antibody(s) for specific nucleobase.

$R_3$ may be 1-10 phosphate or phosphate analog groups. Phosphate analogs include phosphorothioate (PS), in which the phosphorothioate bond substitutes a sulfur atom for a non-bridging oxygen in the phosphate backbone of the DNA, or any other suitable phosphate analog known in the art. In some cases, $R_3$ may be 1-10 phosphate groups. In some cases, $R_3$ may be 3-12 phosphate groups. In some cases, the nucleotide analogue is a nucleoside triphosphate.

In certain embodiments $R_1$ of Formula I has a MW less than 184, often less than 174, often less than 164, often less than 154, often less than 144, often less than 134, often less than 124, often less than 114, often less than 104, often less than 94, and sometimes less than 84. $R_1$ may act as a hapten and elicit an immune response when conjugated to a larger carrier molecule such as KLH.

It will be appreciated that the unincorporated NLRT nucleotide analogue is suitable as a substrate for an enzyme with DNA polymerase activity and can be incorporated into a DNA strand at the 3' terminus. For example, the reversible blocking group should have a size and structure such that the NLRT is a substrate for at least some DNA polymerases. The incorporation of an NLRT may be accomplished via a terminal transferase, a polymerase or a reverse transcriptase. Any DNA polymerase used in sequencing may be employed, including, for example, a DNA polymerase from *Thermococcus* sp., such as 9° N or mutants thereof, including A485L, including double mutant Y409V and A485L. As is known in the art, polymerases are highly discriminating with regard to the nature of the 3' blocking group. As a result, mutations to the polymerase protein are often needed to drive efficient incorporation. Exemplary DNA polymerases and methods that may be used in the invention include those described in Chen, C., 2014, "DNA Polymerases Drive DNA Sequencing-By-Synthesis Technologies: Both Past and Present" *Frontiers in Microbiology*, Vol. 5, Article 305, Pinheiro, V. et al. 2012 "Polymerase Engineering: From PCR and Sequencing to Synthetic Biology" *Protein Engineering Handbook: Volume* 3:279-302. International patent publications WO2005/024010 and WO2006/120433, each of which is incorporated by reference for all purposes. In some cases the polymerase is DNA polymerase from *Thermococcus* sp., such as 9° N or mutants thereof, including A485L, including double mutant Y409V and A485L. Other examples include *E. coli* DNA polymerase 1, Klenow fragment of DNA polymerase I, T7 or T5 bacteriophage DNA polymerase, HIV reverse transcriptase; Phi29 polymerase, and Bst DNA polymerase.

It will be understood that modifications to the blocking group should not interfere with the reversible terminator function. That is, they should be cleavable to produce a 3'-OH deoxyribonucleotide.

In an embodiment, the RTs have Structure II, below, prior to incorporation of the RT into a DNA strand.

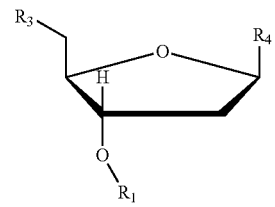

Structure II where $R_1$ is a 3'-O reversible blocking group, $R_4$ is a nucleobase selected from adenine (A), cytosine (C), guanine (G), thymine (T), and uracil (U); and $R_3$ comprises at least one (e.g., 1-10) phosphate. In some cases, $R_3$ is triphosphate.

In an embodiment the RTs have Structure III, below, after incorporation of the RT into a DNA strand.

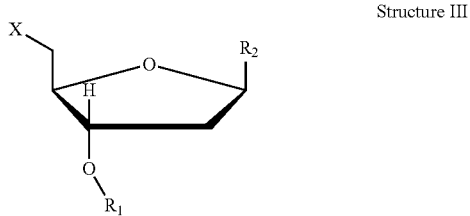

Structure III where $R_1$ is a 3'-O reversible blocking group, $R_2$ is a nucleobases such as adenine (A), cytosine (C), guanine (G), thymine (T), uracil (U), or inosine (I) or analogs thereof, and X is a polynucleotide (e.g., GDS) comprising 10-1000 nucleosides linked by phosphate-sugar bonds (e.g., phosphodiester bonds linking the 3' carbon atom of one nucleoside sugar molecule and the 5' carbon atom of another nucleoside sugar molecule).

In another embodiment, the RTs have Structure IV, after incorporation and removal of the reversible blocking group.

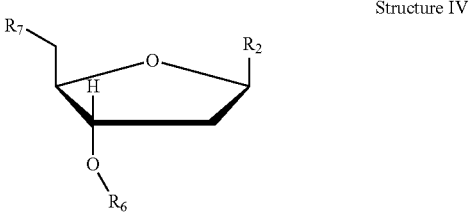

Structure IV $R_6$ is H and $R_7$ is a polynucleotide (e.g., GDS) comprising 10-1000 nucleosides linked by phosphate-sugar bonds, as defined above, or is $R_3$, as defined above.

In certain embodiments of Structures I, III and IV, $R_2$ is a nucleobase analog (e.g., an analog of A, T, G, C, U) with modifications that do not change the binding specificity of the base (i.e., A analog binds T, T analog binds A, etc.) and (ii) but which may render the analog more immunogenic than the naturally occurring base. In some embodiments the modification may comprise additions of a group comprising no more than 3 carbons. The added group is not removed from nucleosides as they are incorporated into the GDS so that the GDS comprises a plurality of nucleotides comprising the modification. In such embodiments the affinity reagent binds the terminal nucleotide analog, including the modification, but binds internal nucleotides with the modification with much lower affinity.

In applications in which there is more than one terminal nucleotide at a given end (e.g., 3' end), various methods can be used to block ends that are not of interest, e.g. by different blocking groups or attaching the "contaminating" end to a support. For DNB sequencing, for example, there may be 3' ends in addition to the 3' end that is used for sequencing. In PCR clusters produced by bridge PCR, sequencing templates are attached by the 5' end, thus the 3' end of the template is non-extendable with RTs or modified to prevent binding with the molecular binders described here.

3.2 Reversible Terminator Blocking Groups

Figure 3:
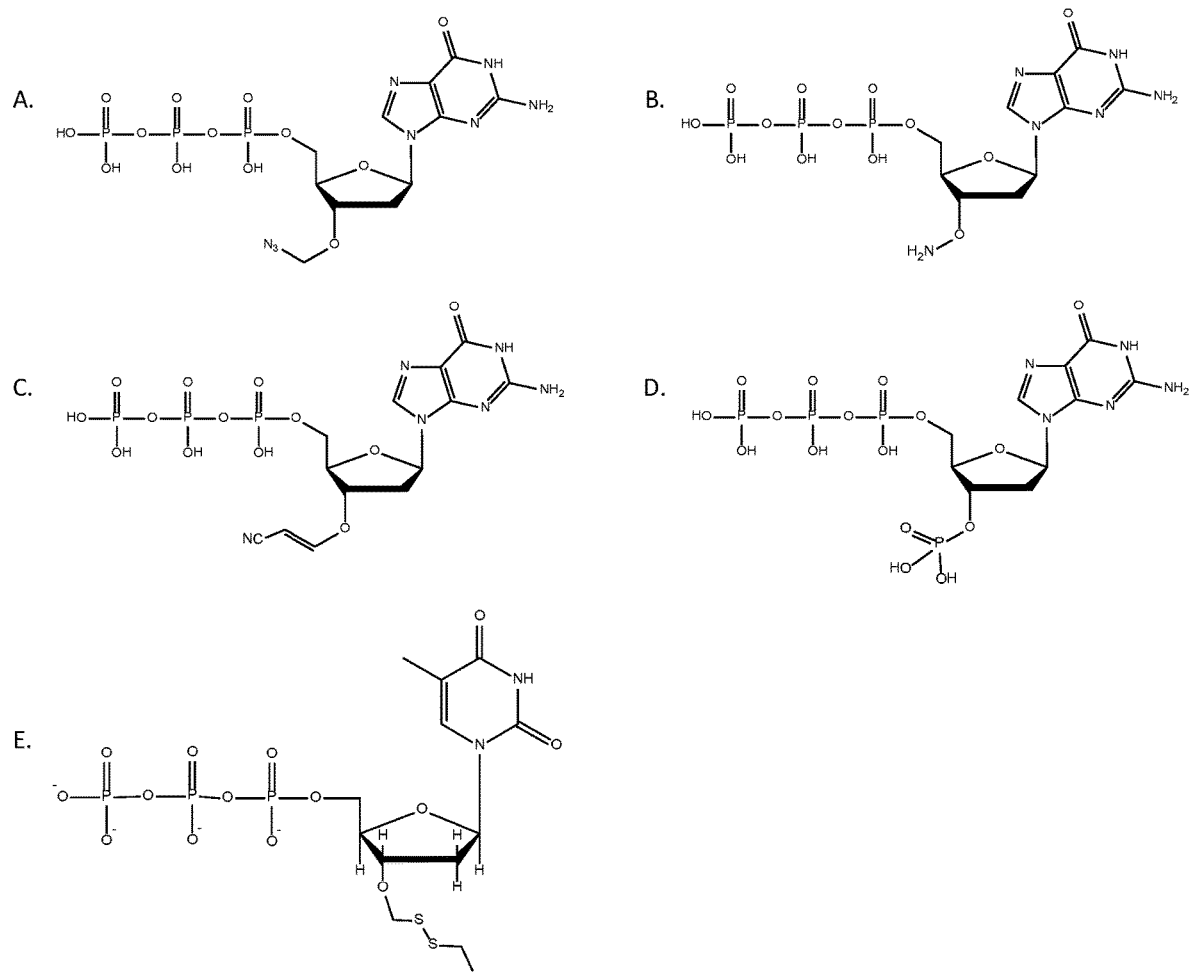
FIG. 3 shows examples of NLRT structures.
Figure 4:
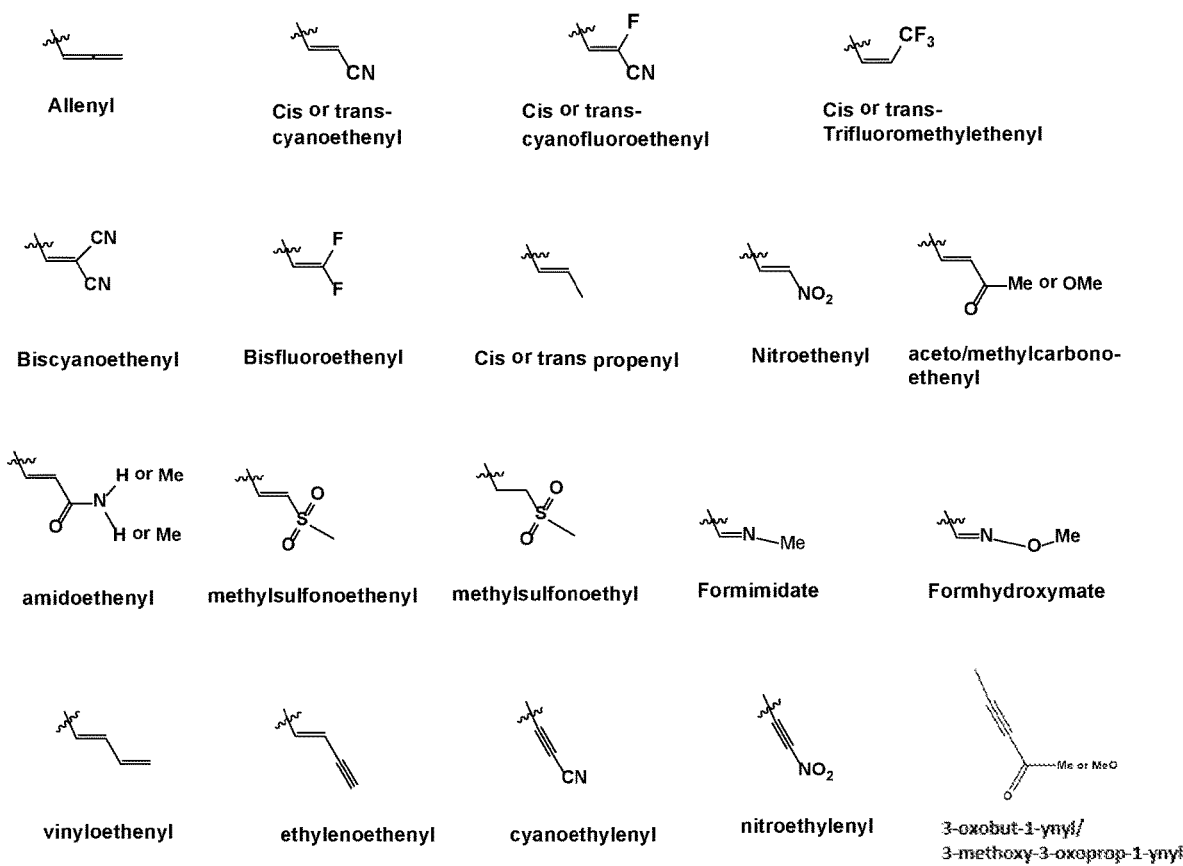
FIG. 4 illustrates various blocking groups that can be used in the practice of the invention.

An NLRT used in the present invention can include any suitable blocking group. In some embodiments a suitable blocking group is one that may be removed by a chemical or enzymatic treatment to produce a 3'-OH group. A chemical treatment should not significantly degrade the template or primer extension strand. Various molecular moieties have been described for the 3' blocking group of reversible terminators such as a 3'-O-allyl group (Ju et al., *Proc. Natl. Acad. Sci. USA* 103: 19635-19640, 2006), 3'-O-azidomethyl-dNTPs (Guo et al., *Proc. Natl Acad. Sci. USA* 105, 9145-9150, 2008), aminoalkoxyl groups (Hutter et al., *Nucleosides, Nucleotides and Nucleic Acids*, 29:879-895, 2010) and the 3'-O-(2-cyanoethyl) group (Knapp et al., *Chem. Eur. J.*, 17, 2903-2915, 2011). Exemplary RT blocking groups include —O-azidomethyl and —O-cyanoethenyl. Other exemplary RT blocking groups, for illustration and not limitation, are shown in FIGS. 3 and 4.

In other embodiments, $R_1$ of Formula I (supra) is a substituted or unsubstituted alkyl, substituted or unsubstituted alkenyl, substituted or unsubstituted alkynyl, substituted or unsubstituted heteroalkyl, substituted or unsubstituted heteroalkenyl, or substituted or unsubstituted heteroalkynyl. In some examples, $R_1$ can be selected from the group consisting of allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl, 3-oxobut-1-ynyl, and 3-methoxy-3-oxoprop-1-ynyl.

A variety of 3'-O reversible blocking groups ($R_1$ in Formula I) may be used in the practice of the invention. According to one embodiment of the methods of the invention, $R_1$ is selected from the group consisting of allyl, azidomethyl, aminoalkoxyl, 2-cyanoethyl, substituted alkyl, unsubstituted alkyl, substituted alkenyl, unsubstituted alkenyl, substituted alkynyl, unsubstituted alkynyl, substituted heteroalkyl, unsubstituted heteroalkyl, substituted heteroalkenyl, unsubstituted heteroalkenyl, substituted heteroalkynyl, unsubstituted heteroalkynyl, allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl, amino, cyanoethenyl, cyanoethyl, alkoxy, acyl, methoxymethyl, aminoxyl, carbonyl, nitrobenzyl, coumarinyl, and nitronaphthalenyl.

As used herein, the terms "alkyl," "alkenyl," and "alkynyl" include straight- and branched-chain monovalent substituents. Examples include methyl, ethyl, isobutyl, 3-butynyl, and the like. Ranges of these groups useful with the compounds and methods described herein include $C_1$-$C_{10}$ alkyl, $C_2$-$C_{10}$ alkenyl, and $C_2$-$C_{10}$ alkynyl. Additional ranges of these groups useful with the compounds and methods described herein include $C_1$-$C_8$ alkyl, $C_2$-$C_8$ alkenyl, $C_2$-$C_8$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

"Heteroalkyl," "heteroalkenyl," and "heteroalkynyl" are defined similarly as alkyl, alkenyl, and alkynyl, but can contain O, S, or N heteroatoms or combinations thereof within the backbone. Ranges of these groups useful with the compounds and methods described herein include $C_1$-$C_{10}$ heteroalkyl, $C_2$-$C_{10}$ heteroalkenyl, and $C_2$-$C_{10}$ heteroalkynyl. Additional ranges of these groups useful with the compounds and methods described herein include $C_1$-$C_8$ heteroalkyl, $C_2$-$C_8$ heteroalkenyl, $C_2$-$C_8$ heteroalkynyl, $C_2$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The alkyl, alkenyl, alkynyl, heteroalkyl, heteroalkenyl, or heteroalkynyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkyl, alkenyl, alkynyl, heteroalkyl, heteroalkenyl, or heteroalkynyl has a full complement of hydrogens, i.e., commensurate with its saturation level, with no substitutions, e.g., linear butane (—$(CH_2)_3$—$CH_3$).

In other embodiments, the reversible blocking group is an amino-containing blocking group (e.g., $NH_2$—). See, Hutter et al., 2010, *Nucleosides Nucleotides Nucleic Acids* 29(11), incorporated herein by reference, which describes exemplary amino-containing reversible blocking groups. In some embodiments, the reversible blocking group is an allyl-containing blocking group (e.g. $CH_2$=$CHCH_2$—). In some embodiments the reversible blocking group comprises a cyano group (e.g. a cyanoethenyl or cyanoethyl group). In some embodiments, the reversible blocking group is an azido-containing blocking group (e.g., $N_3$—). In some embodiments, the reversible blocking group is azidomethyl ($N_3CH_2$—). In some embodiments, the reversible blocking group is an alkoxy-containing blocking group (e.g., $CH_3CH_2O$—). In some embodiments, the reversible blocking group contains a polyethylene glycol (PEG) moiety with one or more ethylene glycol units. In some embodiments, the reversible blocking group is a substituted or unsubstituted alkyl (i.e., a substituted or unsubstituted hydrocarbon). In some embodiments, the reversible blocking group is acyl. See, U.S. Pat. No. 6,232,465, incorporated herein by reference. In some embodiments, the reversible blocking group is or contains methoxymethyl. In some embodiments, the reversible blocking group is or contains aminoxyl ($H_2NO$—). In some embodiments, the reversible blocking group is or contains carbonyl (O=CH—). In some embodiments, the reversible blocking group comprises an ester or phosphate group.

In some embodiments, the reversible blocking group is nitrobenzyl ($C_6H_4(NO_2)$—$CH_2$—). In some embodiments, the reversible blocking group is coumarinyl (i.e., contains a coumarin moiety or a derivative thereof) wherein, e.g., any one of the CH carbons of the coumarinyl reversible blocking group is covalently attached to the 3'-O of the nucleotide analogue.

In some embodiments, the reversible blocking group is nitronaphthalenyl (i.e., contains a nitronaphthalene moiety or a derivative thereof) wherein, e.g., any one of the CH carbons of the nitronaphthalenyl reversible blocking group is covalently attached to the 3'-O of the nucleoside analogue.

In some embodiments the reversible blocking group is selected from the group:

Structures VI-XIII

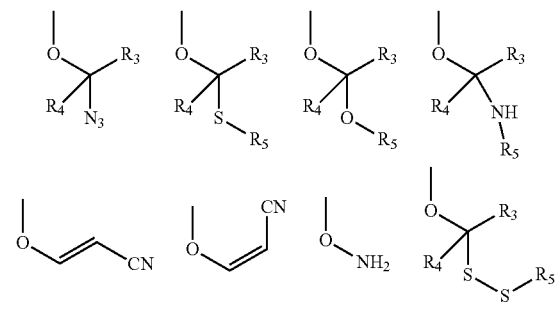

where $R_3$ and $R_4$ are H or alkyl, and $R_5$ is alkyl, cycloalkyl, alkenyl, cycloalkenyl, and benzyl. In certain embodiments the determination of $R_3$-$R_5$ is constrained by MW limitations described herein (e.g., see Section 3.2.1).

Other reversible blocking groups suitable for use in the present invention are described in the literature as a blocking group of a labeled reversible terminator. Generally any suitable reversible blocking group used in sequencing-by-synthesis may be used in the practice of the invention.

3.2.1 Properties of Reversible Terminator Blocking Groups and Nucleotides Containing Them Preferably, for sequencing applications, the blocking group of RTs is removable under reaction conditions that do not interfere with the integrity of the DNA being sequenced. The ideal blocking group will exhibit long term stability, be efficiently incorporated by the polymerase enzyme, cause total blocking of secondary or further incorporation and have the ability to be removed under mild conditions that do not cause damage to the polynucleotide structure, preferably under aqueous conditions.

In certain embodiments of the invention, a blocking group (including the deoxyribose 3' oxygen atom) has a molecular weight (MW) less than 200, often less than 190, often less than 180, often less than 170, often less than 160, often less than 150, often less than 140, often less than 130, often less than 120, often less than 110, and sometimes less than 100). Stated differently, in certain embodiments $R_3$ of Formula I has a MW less than 184, often less than 174, often less than 164, often less than 154, often less than 144, often less than 134, often less than 124, often less than 114, often less than 104, often less than 94, and sometimes less than 84.

The molecular weights of deoxyribonucleotide monophosphates are in the range of about 307 to 322 (dAMP 331.2, dCMP 307.2, dGMP 347.2 and dTMP 322.2). In certain embodiments, the NLRT moiety when incorporated into a GDS (i.e., not including the pyrophosphate of dNTPs) has a molecular weight less than 550, often less than 540, often less than 530, often less than 520, often less than 510, often less than 500, often less than 490, often less than 480, often less than 470, and sometimes less than 460.

3.3 Phosphate Containing Moieties

In some embodiments the $R_3$ moiety comprises one or more phosphate and/or phosphate analog moieties. In some embodiments the $R_3$ moiety may have the structure below (Structure V) where n=0 to 12 (usually 0, 1, 3, 4, 5 or 6) and X is H or any structure compatible with incorporation by polymerase in a primer extension reaction. For example, X may be alkyl or any of a variety of linkers described in the art. See, e.g., U.S. Pat. No. 9,702,001, incorporated herein by reference. It will be appreciated that in the process of incorporation of a reversible terminator into a GDS, moiety X is removed from the nucleotide (along with all but the alpha phosphate) such that X is not present in the incorporated reversible terminator deoxyribonucleotide. In certain embodiments X may be a detectable label or affinity tag, with the proviso that affinity reagents of the invention do not bind to moiety X, or discriminate among, reversible terminators based on the presence, absence or structure of moiety X, and that X is not present in the incorporated reversible terminator deoxyribonucleotide.

Structure XIV

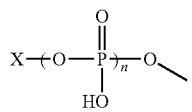

3.4 NLRT Sets

In some approaches SBS sequencing according to the invention comprises contacting a sequencing array with multiple NLRTs (e.g., NLRT-A, NLRT-T, NLRT-C and NLRT-G). The contacting may be carried out sequentially, one NLRT at a time. Alternatively, the four NLRTs may be contacted with the sequencing array at the same time, most often as a mixture of the four NLRTs. Together, the four NLRTs make up an "NLRT set." NLRTs of an NLRT set may be packaged as a mixture or may be packaged as a kit comprising each different NLRT is a separate container. In a mixture of the four NLRTs may include each base in equal proportion or may include unequal amounts.

In one embodiment each NLRT in an NLRT set comprises the same blocking group (e.g. azidomethyl). In one embodiment NLRTs in an NLRT set comprise different blocking groups (e.g. NLRT-A comprises azidomethyl and NLRT-T comprises cyanoethenyl; or NLRT-A and NLRT-G comprise azidomethyl and NLRT-C and NLRT-T comprise cyanoethenyl). If different blocking groups are used, such blocking groups are optionally selected such that the different blocking group can be removed by the same treatment. Alternatively the blocking groups may be selected to be removed by different treatments, optionally at different times. In one embodiment one or more NLRTs in a set comprises a modified (nonnaturally occurring nucleobase).

The NLRTs described herein can be provided or used in the form of a mixture. For example, the mixture can contain two, three, or four (or more) structurally different NLRTs. The structurally different NLRTs can differ in their respective nucleobases. For example, the mixture can contain four structurally different NLRTs each comprising one of the four natural DNA nucleobases (i.e., adenine, cytosine, guanine, and thymine), or derivatives thereof.

For sequencing purposes, different NLRTs in an NLRT set may be separately packaged then mixed on the sequencer itself (e.g., before delivery to a flow cell) or may be packaged together (i.e., premixed). Kits comprising NLRT sets (with different NLRTs packaged in separate containers or as a mixture in the same container) may be provided.

3.5 Nucleobase Analogs with Groups that Improve Affinity Reagent Binding

In one embodiment the nucleobase includes a non-removable chemical group that increases the specificity or affinity of the affinity reagent for the nucleobase when present at the 3' terminus of the growing DNA strand (i.e., as the last-incorporated base), but which is not recognized by, or not accessible to, the affinity reagent in nucleotides internal to the primer extension product. In one approach the modification is recognized by or bound by the affinity reagent but with a lower affinity or lower efficiency relative to the same modification in a 3' terminal nucleotide.

For illustration and not limitation, examples of such modified nucleobases include:

STRUCTURES XV-XVIII

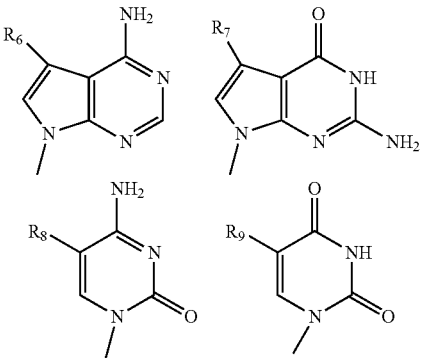

$R_6$, $R_7$, $R_8$, and $R_9$: may be the same or different, each selected from H, I, Br, F, Structures XIX-XXVIII, or any groups that do not interfere with base pairing. Note that when $R_9$ is methyl Structure XVIII in thymidine. In some cases, the modification has the additional benefit of increasing the antigenicity of the nucleotide.

STRUCTURES XIX-XXVIII

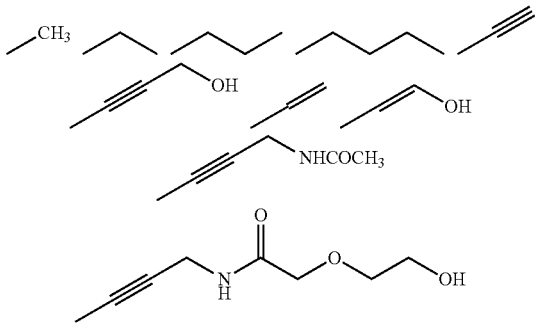

The molecular weights of naturally occurring nucleobases are: adenine 135; guanine 151, thymine 126 and cytosine 111. In some embodiments the nucleobase analog has a molecular weight that does not exceed that of the natural base by more than 10, 20, 30, 40, 50, 60, 70, 80, 90, or 100 Da.

3.6 Unblocked dNTPs

In one embodiment, natural dNTPs (e.g., dATP, dGTP, dCTP or dTTP) or dNTP analogs without a 3'-O-blocking group are used for sequencing. In some embodiments, the nucleotides are incorporated one at a time in the sequencing process, as in pyrosequencing or by a polymerase that halts after one base incorporation. Exemplary methods are described in the literature (see, e.g., Ju et al., 2006, *Proc. Natl. Acad. Sci. USA* 103:19635-40, 2006; Guo, *Proc. Natl Acad. Sci. USA* 105, 9145-50, 2008, and Ronaghi et al., *Science,* 281:363-365, 1998) which may be modified for use in the present invention by removal of a label and/or a linker connecting the label to the RT. In some approaches, dNTPs with different nucleobases are added and incorporated sequentially (e.g., A, then G, etc.). Usually nucleobase is separately imaged prior to addition of the next dNTP.

3.7 Deoxyribose Analogs

In some embodiments of the invention the sugar (deoxyribose) moiety is modified. For example, an NLRT with the nucleobase adenine, the blocking group azidomethyl, and the sugar deoxyribose can be distinguished from an NLRT with the nucleobase cytosine, the blocking group azidomethyl, and the sugar modified-deoxyribose using an affinity reagent that so that it is recognizes the blocking group and sugar moieties.

3.8 Nucleotides Without 3'-O Reversible Terminators

In a different aspect, useful in several applications, a nucleotide with a nonremovable (i.e., not cleavable) 3' blocking group is used in place of a NLRT. In one approach, after detection with the affinity reagent, the last-incorporated base is removed and its position is filed in with a nucleotide that is similar but that has a cleavable blocking group (Koziolkiewicz et al., FEBS Lett. 434:77-82, 1998).

The examples given above include reversible blocking groups attached to the nucleotide via the 3'-O of the deoxyribose sugar moiety. The present invention also includes NLRTs with reversible and non-reversible blocking groups attached to the 2'-O- of the deoxyribose sugar. These embodiments may be used for single base detection (single or a few base primer extension), monitoring gaps and nicks in DNA and other detection methods. Thus, one of ordinary skill in the art will be able to apply the methods and information herein to NLRTs with 2', rather than 3', blocking groups.

4. Affinity Reagents

The present invention uses affinity reagents that specifically bind to NLRTs at the 3' end of a GDS, e.g., after incorporation by a polymerase to the end of a growing DNA chain during SBS. In one embodiment the affinity reagent binds an NLRT of Structure III. In one embodiment the affinity reagent binds an NLRT of Structure IV.

4.1 Affinity Reagents Generally

In one aspect the invention relates to affinity reagents used to detect the presence or absence of an NLRT incorporated at the 3' end of a nucleic acid. An affinity reagent is a molecule or macromolecule that specifically binds an NLRT based on a structural feature of the incorporated NLRT. For example, an affinity reagent may specifically bind to an NLRT having, e.g., a particular base and/or particular reversible blocking group. For illustration, one example of an affinity reagent is a monoclonal antibody (mAb) that binds with high affinity to an incorporated NLRT at the 3' end of a DNA strand when the NLRT comprises the nucleobase adenosine and an azidomethyl reversible blocking group but does not bind with high affinity to an NLRT incorporated at the 3' end of a DNA strand when the NLRT comprises the nucleobase adenosine but has a 3' hydroxyl group rather than an azidomethyl reversible blocker, and does not bind with high affinity to an NLRT incorporated at the 3' terminus of a DNA strand comprising the nucleobase cytosine, guanine, or thymine, each with or without an azidomethyl reversible blocking group. Affinity reagents may be directly or indirectly labeled.

"Specificity" is the degree to the affinity reagent discriminates between different molecules (e.g., NLRTs) as measured, for example, by relative binding affinities of the affinity reagent for the molecules. With respect to the affinity reagents of the present invention, an affinity reagent should have substantially higher affinity for one NLRT (its target NLRT) than for other NLRTs (for example, the affinity reagent binds to a C nucleoside analogue but not to A, T or G). Also, the affinity reagent binds to its target nucleoside analog at the end of a polynucleotide when incorporated by a polymerase at the 3' end of a growing DNA chain, but not to a nucleotide base elsewhere on the DNA chain. An affinity reagent is specific for a particular NLRT, such as NLRT-A, if in the presence of a plurality (e.g., an array) of template polynucleotides are present in which 3'-termini of GDSs include NLRT-A, NLRT-T, NLRT-C, NLRT-G (e.g., in an array) the affinity reagent binds preferentially to NLRT-A under reaction conditions used in SBS sequencing. As used herein, "preferential binding" of an affinity agent to a first structure compared to a second structure means the affinity agent binds the first structure but does not bind the second structure or binds the second structure less strongly (i.e., with a lower affinity) or less efficiently.

In the context of the binding of an affinity reagent to an incorporated NLRT, the terms "specific binding," "specifically binds," and the like refer to the preferential association of an affinity reagent with a particular NLRT (e.g., NLRT-A having a 3'-O azido group) in comparison to an NLRT with a different nucleobase (NLRT-T, —C, or -G), a different blocking group, or no blocking group (e.g., deoxyadenosine with a 3'-OH). Specific binding between an affinity reagent and the NLRT sometimes means an affinity of at least $10^{-6}$ $M^{-1}$ (i.e., an affinity having a lower numerical value than $10^{-6}$ $M^{-1}$ as measured by the dissociation constant KA). Affinities greater than $10^{-8}$ $M^{-1}$ are preferred. Specific binding can be determined using any assay for binding (e.g., antibody binding) known in the art, including Western Blot, enzyme-linked immunosorbent assay (ELISA), flow cytometry, immunohistochemistry, and detection of fluorescently labeled affinity reagent bound to a target NLRT in a sequencing reaction. As discussed herein below, specificity of binding can be determined by positive and negative binding assays.

The specific binding interaction between an affinity reagent, such as an antibody, and an incorporated reversible terminator deoxyribonucleotide can be described in various ways including with reference to the portion, or moiety, of the incorporated reversible terminator deoxyribonucleotide responsible for the specificity. An analogy is useful here: Imagine a protein with two domains, domain 1 and domain 2. Two different antibodies may specifically bind the protein. However, they may recognize different epitopes. For example, one antibody may bind an epitope in domain 1 and the second antibody may bind an epitope in domain 2. In this hypothetical, if modifications are made in domain 1 this may affect the binding of the protein by the first antibody, without changing the binding by the second antibody. In this case the binding of protein by the first antibody may be said to be "dependent on" on domain 1, meaning that a change in domain 1 (e.g., a change in amino acid sequence) will change the binding properties of antibody 1 (e.g., abolish binding, increase binding affinity, reduce binding affinity, etc.). Equivalently, domain 1 may be said to be "responsible for" binding by antibody 1. In the case of an incorporated reversible terminator deoxyribonucleotide specificity of binding may be due to a structural feature of one moiety (e.g., the blocking group) and be unaffected by the structure of other moieties (e.g., the nucleobase) by other moieties. Alternatively, specificity of binding may be due to structural features of multiple moieties (e.g., both the nucleobase and blocking group), etc. Where binding of an affinity reagent to an incorporated reversible terminator deoxyribonucleotide requires the presence of particular structural features of a moiety, the binding by the affinity reagent may "be specific for" or "based on" the presence or absence of a moiety with those structural features. Equivalently, the moiety with those structural features may be "responsible" for binding by the affinity reagent, or binding of the affinity reagent may be "dependent" on the presence of a moiety with those structural features.

It should also be noted that "specificity" may depend on the environment. For example, imagine an affinity reagent that binds both A and A', but does not bind B, C or D. In a reaction or sample containing A, A', B and C, the affinity reagent may bind both A and A', and thus may not be considered to "specifically bind" A. However, in a reaction or sample containing A, B, C and D, the affinity reagent would bind only A, and in that environment would be said to specifically bind A. In another example, in a sample containing A, A', B and C, the affinity reagent may bind A and A' with different affinities, or efficiencies, so that the binding to A and the binding to A' could be distinguished on those bases.

Another related term is "discriminate" (or sometimes "distinguish"). An affinity reagent that binds incorporated reversible terminator deoxyribonucleotides only if particular blocking group (e.g., azidomethyl) is present, but binds to incorporated reversible terminator deoxyribonucleotides with azidomethyl blocking groups without regard to what nucleobase is present, can be said to "discriminate" between incorporated reversible terminator deoxyribonucleotides with and without an azidomethyl blocking group or, more broadly, can be said to "discriminate based on the blocking group."

The specificity of an affinity reagent is a result of the process used to make the affinity reagent. For example, a reagent that recognizes an azidomethyl blocking moiety may be tested empirically with positive and negative binding assays. For illustration, in one approach the reagent is an antibody that binds an NLRT based on the presence of an O-azidomethyl blocking moiety. In one approach antibodies are raised against the hapten O-azidomethyl using azidomethyl conjugated to keyhole limpet hemocyanin. The desired antibody can be selected for binding to 3'-O-azidomethyl-2'-deoxyguanine but against binding to other deoxyguanine nucleotides such as 3'-O-2-(cyanoethoxy)methyl-2'-deoxyguanine; 3'-O-(2-nitrobenzyl)-2'-deoxyguanine; and 3'-O-allyl-2'-deoxyguanine; and against binding other azidomethyl NLRTs such as 3'-O-azidomethyl-2'-deoxyadenosine; 3'-O-azidomethyl-2'-deoxycytosine; and 3'-O-azidomethyl-2'-deoxythymine.

The nature of antibody-hapten interactions can also be determined using art-known methods such as those described in Al Qaraghuli, 2015, "Defining the complementarities between antibodies and haptens to refine our understanding and aid the prediction of a successful binding interaction" *BMC Biotechnology*, 15(1)p. 1; Britta et al., 2005, "Generation of hapten-specific recombinant antibodies: Antibody phage display technology: A review" *Vet Med.* 50:231-52; Charlton et al., 2002. "Isolation of anti-hapten specific antibody fragments from combinatorial libraries" *Methods Mol Biol.* 178:159-71; and Hongtao et al., 2014, "Molecular Modeling Application on Hapten Epitope Prediction: An Enantioselective Immunoassay for Ofloxacin Optical Isomers" *J. Agric. Food Chem.* 62 (31) pp 7804-7812. It will be understood that describing an affinity reagent as binding certain moieties (e.g., a nucleobase and a sugar moiety) does not exclude binding to other parts of the incorporated nucleotide. For example, an affinity reagent that binding a nucleobase and a sugar moiety may also bind a blocking group.

Examples of useful affinity reagents include antibodies (including binding fragments of antibodies, single chain antibodies, bispecific antibodies, and the like), aptamers, knottins, affimers, labeled dNTPs that form a one-base triple helix, guanine nucleotide binding proteins (G-proteins), or any other known agent that binds an incorporated NLRT with a suitable specificity and affinity.

The affinity reagent may specifically recognize the nucleobase, the sugar (e.g., deoxyribose), the blocking group, or any other moiety or combination thereof in the target NLRT. In one approach the affinity reagent recognizes an epitope comprising the blocking group. In another approach the affinity reagent recognizes an epitope comprising the nucleobase. In another approach the affinity reagent recognizes an epitope comprising the nucleobase and the blocking group. It will be understood that even if the affinity reagent does not contact a moiety, the moiety may dictate the position of other moieties. For example, for an affinity reagent that discriminates NLRT based on the nucleobase and 3' blocking group, the deoxyribose moiety is required to position a nucleobase and 3' blocking group for recognition.

In the case of affinity reagents that are antibodies, specific binding can be determined using any assay for antibody binding known in the art, including Western Blot, enzyme-linked immunosorbent assay (ELISA), flow cytometry, or column chromatography. In one approach specific binding is demonstrated using an ELISA type assay. For example, serum antibodies raised against 3'-azidomethyl-dC can be serially titrated against a bound substrate of 3'-O-azidomethyl-dC (positive specificity assay) and nucleotide(s) such as 3'-O-azidomethyl-dG or -dA or 3'-OH-dC (negative specificity assay).

In some embodiments, the base-specific binding of an affinity reagent for its target nucleoside is 2-100-fold higher than binding to other nucleosides or analogs. In some embodiments base-specific binding of an affinity reagent for its target nucleoside is at least 10-fold higher than binding to other nucleosides, or at least 30-fold higher, or at least 100-fold higher The preferred the antibody binding efficiency to the specific base is at the concentration lower than 100 pM, or lower than 1 nM, or lower than 10 nM, or lower than 1 μM.

Affinity reagents with desired specificity can be selected using art-known methods. For example, an affinity reagent such as an antibody can be identified, selected, or purified by rounds of positive selection (i.e., binds to target molecule) and negative selection (i.e., does not binds to molecules that are not target molecule).

An affinity reagent may bind both a dNTP in solution and the corresponding nucleotide incorporated at the 3' terminus of a primer extension product. In some embodiments the affinity reagent does not bind an unincorporated NLRT (e.g., an NLRT in solution) or binds with a significantly lower specificity. In general, however, binding of non-incorporated NLRTs by affinity reagents does not occur in the process of sequencing because unincorporated NLRTs are removed (washed away) prior to introduction of the affinity reagents. Alternatively, complexes formed by affinity reagents bound to NLRTs are removed (washed away) prior to imaging.

In one approach, the affinity reagent binds specifically to the nucleobase and distinguishes among different bases (e.g., A, T, G, C) in part based on the presence or absence of a 3'-OH group. In this approach the affinity reagent distinguishes a nucleotide at the 3' end of a GDS with a 3'-OH from incorporated nucleotides interior to the GDS (not at the 3' end). In some cases the affinity reagent that recognizes a specific nucleobase also distinguishes between the presence or absence of a 3'-OH groups, thereby recognizing an incorporated NLRT as a 3' terminal nucleotide with a particular nucleobase.

In one approach the affinity reagent recognizes an epitope comprising the blocking group but does not distinguish between bases. For example, given four RT blocking groups [A. azidomethyl, B. 2-(cyanoethoxy)methyl, C. 3'-O-(2-nitrobenzyl), and D. 3'-O-allyl]affinity reagents can be produced that distinguish the four blocking groups. For illustration, given the deoxyguanine analogs labeled A to D below, an affinity reagent can be selected that recognizes only one, but not the other three, NLRTs.

A. 3'-O-azidomethyl-2'-deoxyguanine
B. 3'-O-2-(cyanoethoxy)methyl-2'-deoxyguanine
C. 3'-O-(2-nitrobenzyl)-2'-deoxyguanine
D. 3'-O-allyl-2'-deoxyguanine In some embodiments the selected affinity reagent does not distinguish between nucleotides with different nucleobases provided they share the same blocking group. For example, an affinity reagent that recognizes B (3'-O-2-(cyanoethoxy)methyl-2'-deoxyguanine), above, may also recognize 3'-O-2-(cyanoethoxy)methyl-2'-deoxyadenine; 3'-O-2-(cyanoethoxy)methyl-2'-deoxythymine; and 3'-O-2-(cyanoethoxy)methyl-2'-deoxycytosine.

Generating affinity reagents (e.g., monoclonal antibodies) that differentially recognize RT blocking groups is within the skill of one of ordinary skill in the art guided by this disclosure. In one approach an antibody is raised against the hapten O-azidomethyl (e.g., —O— azidomethyl or azidomethyl conjugated to keyhole limpet hemocyanin) and positively and negatively screened for binding to a 3'-O-azidomethyl-2'-dNM nucleotide at the 3' end of a GDS TP (where N is each of A, T, G or C) and for not binding to 3'-O-X-2'-dNM where O—X is a different blocking group present in the sequencing reaction. It will be recognized that in other embodiments, the hapten may be deoxyribose with the 3'-O blocking group, a nucleotide (e.g., monophosphate or triphosphate with a 3'-O blocking group), or the like, so long as the selection process identified affinity reagents with the desired specificity.

Although the example above described an embodiment in which the four nucleotides had different blocking groups with very distinct structural differences (e.g., azidomethyl vs 2-(cyanoethoxy)methyl, in some embodiments of the present invention there are only small differences between blocking groups bound by distinct affinity reagents. For example, in a blocking group a hydrogen atom may be replaced by a fluorine atom or methyl group to generate three related blocking groups [blocking group, F substitute blocking group, methyl substituted blocking group] that can be distinguished by a set of affinity reagents.

In some embodiments of the invention sequencing is carried out using four NLRT each having a 3'-O-blocking group in which the blocking groups of 2 or more, alternatively 3 or more, alternatively all 4 are structurally similar in the sense that (1) they have the same number of atoms or the number of atoms differs by no more than a small number (e.g., 1, 2, 3, 4, 5, 6, 7, 8, 9, or 10); (2) the molecular formulas of the blocking group moieties differ by 1 to 10 atoms (e.g., single H replaced by $CH_3$ is 3 differences; H replaced by F, O replaced by S), e.g., 1 atom, 2 atoms, 3 atoms, 4 atoms, 6 atoms, 7 atoms, 8 atoms, 9 atoms or 10 atoms. In these and other embodiments the blocking group moiety may have any of the properties described hereinabove in the section captioned "Properties of Reversible Terminator Blocking Groups and Nucleotides Containing Them."

In some embodiments the affinity reagent binds to a NLRT (e.g., 3'-O-azidomethyl-2'-deoxyguanine) but does not bind to the corresponding unblocked nucleotide (e.g., 3'-OH-2'-deoxyguanine).

In one embodiment, the affinity reagent binds to a NLRT (e.g., 3'-O-azidomethyl-2'-deoxyguanine) but disassociates from the nucleotide analog after treatment to remove the blocking group (e.g., after treatment with TCEP (tris(2-carboxyethyl)phosphine)).

An affinity reagent that specifically recognizes NLRT-A is referred to as antiA. An affinity reagent that specifically recognizes NLRT-T is referred to as antiT. An affinity reagent that specifically recognizes NLRT-G is referred to as antiG. An affinity reagent that specifically recognizes NLRT-C is referred to as antiC. An affinity reagent that specifically recognizes NLRT-U is referred to as antiU. Although this nomenclature is similar to that used to describe immunoglobulin specificity, the use of this terminology in the present invention is not intended to indicate that that the affinity reagent is necessarily an antibody. As noted, Affinity reagents may be directly labeled. Alternatively, affinity reagents may be an unlabeled primary affinity reagent detectable using a labeled secondary affinity reagent. For example an unlabeled primary affinity reagent that specifically binds a NLRT may be detected with a labeled secondary affinity reagent that binds the primary affinity reagent (for example, a labeled antibody that binds the primary affinity reagent). See Section 4.5, below 4.2 Exemplary Affinity Reagents In some embodiments, the affinity reagent is an antibody. Any method for antibody production that is known in the art may be employed.

4.2.1 Antibodies

As used herein, "antibody" means an immunoglobulin molecule or composition (e.g., monoclonal and polyclonal antibodies), as well as genetically engineered forms such as chimeric, humanized and human antibodies, heteroconjugate antibodies (e.g., bispecific antibodies), and antibody fragments. The antibody may be from recombinant sources and/or produced in animals, including without limitation transgenic animals. The term "antibody" as used herein includes "antibody fragments," including without limitation Fab, Fab', F(ab')$_2$, scFv, dsFv, ds-scFv, dimers, minibodies, nanobodies diabodies, and multimers thereof and bispecific antibody fragments. Antibodies can be fragmented using conventional techniques. For example, F(ab')$_2$ fragments can be generated by treating an antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques. The antibodies can be in any useful isotype, including IgM and IgG, such as IgG1, IgG2, IgG3 and IgG4. In some embodiments, the affinity reagents are minibodies. Minibodies are engineered antibody constructs comprised of the variable heavy (VH) and variable light (VL) chain domains of a native antibody fused to the hinge region and to the CH3 domain of the immunoglobulin molecule. Minibodies are thus small versions of whole antibodies encoded in a single protein chain which retain the antigen binding region, the CH3 domain to permit assembly into a bivalent molecule and the antibody hinge to accommodate dimerization by disulfide linkages. A single domain antibody (sdAb) may also be used. A single domain antibody, or NANOBODY (Ablynx), is an approximately antibody fragment with a single monomeric variable antibody domain. Single domain antibodies bind selectively to specific antigens and are smaller (MW 12-15 kDa) than conventional antibodies.

4.2.1.1 Production of Antibodies

Methods for raising polyclonal antibodies are known and may be used to produce NLRT-specific antibodies. For one approach see Example 2 below. According to one method for raising polyclonal antibodies specific for a particular NLRT, e.g., NLRT-A, a rabbit is injected with NLRT-A (conjugated to an immunogen) to raise antibodies, and antibodies are selected to do not bind to: the same structure lacking the blocking group (e.g., having a 3'-OH), and the other NLRTs (NLRT-T, NLRT-G, and NLRT-C). Thus, the polyclonal antibodies produced recognize the specific NLRT that is incorporated at the 3' end of a growing DNA chain at a particular position on a sequencing array, but not that same nucleoside at other interior positions of the growing chain or to other NLRTs that may be incorporated elsewhere on the array. (The polyclonal antibodies may also recognize unincorporated NLRT-A, but unincorporated NLRTs are washed away before incorporated NLRTs are probed using labeled affinity reagents.

It will be recognized that, depending on the needs of the investigator, it is not always necessary to raise antibodies against the entire NLRT. For example, if antibodies specific for the blocking group are desired, the hapten may be deoxyribose with a 3'-O-blocking group (i.e., no nucleobase) or the 3'-O-blocking group alone. In some embodiments antibodies are raised against a polynucleotide with a NLRT of interest at the 3' end. In some embodiments antibodies are raised against a polynucleotide annealed to a template molecule.

To produce monoclonal antibodies, antibody producing cells (lymphocytes) can be harvested from an animal immunized with an immunogen comprising an NLRT and fused with myeloma cells by standard somatic cell fusion procedures thus immortalizing these cells and yielding hybridoma cells. Such techniques are well known in the art (e.g., the hybridoma technique originally developed by Kohler and Milstein (Kohler and Milstein Nature 256:495-497, 1975) as well as other techniques such as the human B-cell hybridoma technique (Kozbor et al., 1983, *Immunol. Today* 4:72), the EBV-hybridoma technique to produce human monoclonal antibodies (Cole et al., 1986, *Methods Enzymol*, 121:140-67), and screening of combinatorial antibody libraries (Huse et al., 1989, *Science* 246:1275). Hybridoma cells can be screened immunochemically for production of antibodies specifically reactive with a particular RT and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., *Nature* 341:544-546, 1989; Huse et al. Science 246:1275, 1989; and McCafferty et al. Nature 348:552-554, 1990).

Additionally, antibodies specific for a target NLRT are readily isolated by screening antibody phage display libraries. For example, an antibody phage library is optionally screened by using to identify antibody fragments specific for a target NLRT. Methods for screening antibody phage libraries are well known in the art.

Anti-NLRT antibodies also may be produced in a cell-free system. Nonlimiting exemplary cell-free systems are described, e.g., in Sitaraman et al., Methods Mol. Biol. 498: 229-44, 2009; Spirin, Trends Biotechnol. 22: 538-45, 2004; and Endo et al., Biotechnol. Adv. 21: 695-713, 2003.

4.2.1.2 Antibody Purification

Anti-NLRT antibodies may be purified by any suitable method. Such methods include, but are not limited to, the use of affinity matrices or hydrophobic interaction chromatography. Hydrophobic interactive chromatography, for example, a butyl or phenyl column, may also suitable for purifying some polypeptides. See Section 8.4, below. Many methods of purifying polypeptides are known in the art. Affinity purification of anti-NLRT antibodies from a polyclonal antiserum are described in Example 2 below.

4.2.1.3 Antibody Labeling

Antibodies can be labeled using any methods known in the art. Methods for linking of antibodies and other affinity reagents to reporter molecules, e.g., signal-generating proteins including enzymes and fluorescent/luminescent proteins are well known in the art (Wild, *The Immunoassay Handbook*, $4^{th}$ ed.; Elsevier: Amsterdam, the Netherlands, 2013; Kobayashi and Oyama, Analyst 136:642-651, 2011).

4.2.2 Aptamers

An aptamer is an oligonucleotide or peptide molecule that binds to a specific target molecule. Aptamers can be classified as: (a) DNA or RNA or XNA aptamers, which consist of (usually short) strands of oligonucleotides; and (b) peptide aptamers, which consist of one (or more) short variable peptide domains, attached at both ends to a protein scaffold.

Nucleic acid aptamers are nucleic acid species that have been engineered through repeated rounds of in vitro selection or equivalently, SELEX (systematic evolution of ligands by exponential enrichment) to bind to various molecular targets, e.g., NLRTs. For example, aptamers with affinity for a target NLRT can be selected from a large oligonucleotide library through SELEX, an iterative process in which non-binding aptamers are discarded and aptamers binding to the proposed target are expanded. Initial positive selection rounds are sometimes followed by negative selection. This improves the selectivity of the resulting aptamer candidates. In this process, the target NLRT is immobilized to an affinity column. The aptamer library is applied and allowed to bind. Weak binders are washed away and bound aptamers are eluted and amplified using PCR. Then the pool of amplified aptamers is reapplied to the targets. The process is repeated multiple times under increasing stringency until aptamers of the desired selectivity and affinity are obtained. See, e.g., Jayasena, et al., Clinical Chemistry 45:1628-1650, 1999. Peptide aptamer selection can be made using different systems, including the yeast two-hybrid system. Peptide aptamers can also be selected from combinatorial peptide libraries constructed by phage display and other surface display technologies such as mRNA display, ribosome display, bacterial display and yeast display. These experimental procedures are also known as biopannings. See, e.g., Reverdatto et al., 2015, *Curr. Top. Med. Chem.* 15:1082-1101.

4.2.3 Affimers

Affimers are small (12-14 kDa), highly stable proteins that bind their target molecules with specificity and affinity similar to that of antibodies. These proteins share the common tertiary structure of an alpha-helix lying on top of an anti-parallel beta-sheet. Affimer proteins display two peptide loops and an N-terminal sequence that can all be randomised to bind to desired target proteins with high affinity and specificity in a similar manner to monoclonal antibodies. Stabilisation of the two peptides by the protein scaffold constrains the possible conformations that the peptides can take, increasing the binding affinity and specificity compared to libraries of free peptides.

Affimers specific for a NLRT can be selected by the use of phage display libraries that are screened to identify an Affimer protein with high-specificity binding to the target NLRT and high binding affinities (e.g., in the nM range). Many different labels, tags and fusion proteins, such as fluorophores, have been conjugated to Affimer proteins for use in various applications. See, e.g., U.S. Pat. Nos. 8,481,491, 8,063,019, and WO 2009/136182, which are incorporated herein by reference. See also Crawford et al., Brief Funct. Genomic Proteomic, 2:72-79, 2003.

4.2.4 Knottins

"Knottin" or "inhibitor cystine knot" (ICK) is a protein structural motif containing three disulfide bridges. Along with the sections of polypeptide between them, two disulfides form a loop through which the third disulfide bond (linking the third and sixth cysteine in the sequence) passes, forming a knot. New binding epitopes can be introduced into natural knottins using protein engineering, and knottins have been engineered to target a broad range of targets. One approach to production of knottins that are specific for NLRTs is to create and screen knottin libraries using yeast surface display and fluorescence-activated cell sorting. For information regarding production of knottins with selectivity and high affinity for a target NLRT and labeling such knottins for use in connection with the present invention, see, e.g., Kintzing and Cochran, *Curr. Opin. Chem. Biol.* 34:143-150, 2016; Moore et al., *Drug Discovery Today: Technologies* 9(1):e3-e11, 2012; and Moore and Cochran, Meth. Enzymol. 503:223-51, 2012.

4.3 Labeled Affinity Reagents

Labeled affinity reagents can be used to sequence a template nucleic acid by a variety of methods. They can also be used in a variety of applications other than sequencing, as will be apparent to those of skill in the art. Any method of labeling antibodies and other affinity reagents of the invention may be used.

4.3.1 Fluorescent Detectable Labels

The affinity reagents used in the practice of the invention, including antibodies, aptamers, affimers, knottins and other affinity reagents described herein, can be detectably labeled. For example the affinity reagents described herein can be detectably labeled with fluorescent dyes or fluorophores. "Fluorescent dye" means to a fluorophore (a chemical compound that absorbs light energy of a specific wavelength and re-emits light at a longer wavelength). Fluorescent dyes typically have a maximal molar extinction coefficient at a wavelength between about 300 nm to about 1,000 nm or of at least about 5,000, more preferably at least about 10,000, and most preferably at least about 50,000 cm-1 M$^{-1}$, and a quantum yield of at least about 0.05, preferably at least about 0.1, more preferably at least about 0.5, and most preferably from about 0.1 to about 1.

There is a great deal of practical guidance available in the literature for selecting appropriate detectable labels for attachment to an affinity reagent, as exemplified by the following references: Grimm et al., *Prog. Mol. Biol. Transl. Sci.* 113:1-34, 2013; Oushiki et al., Anal. Chem. 84:4404-4410, 2012; Medintz & Hildebrandt, editors, 2013, "FRET—Förster Resonance Energy Transfer: from theory to applications," (John Wiley & Sons); and the like. The literature also includes references providing lists of fluorescent molecules, and their relevant optical properties for choosing fluorophores or reporter-quencher pairs, e.g., Haugland, Handbook of Fluorescent Probes and Research Chemicals (Molecular Probes, Eugene, 2005); and the like. Further, there is extensive guidance in the literature for derivatizing reporter molecules for covalent attachment via common reactive groups that can be added to an RT or portion thereof, as exemplified by: Ullman et al., U.S. Pat. No. 3,996,345; Khanna et al., U.S. Pat. No. 4,351,760; and the like. Each of the aforementioned publications is incorporated herein by reference in its entirety for all purposes.

Exemplary fluorescent dyes include, without limitation, acridine dyes, cyanine dyes, fluorone dyes, oxazine dyes, phenanthridine dyes, and rhodamine dyes. Exemplary fluorescent dyes include, without limitation, fluorescein, FITC, Texas Red, ROX, Cy3, an Alexa Fluor dye (e.g., Alexa Fluor 647 or 488), an ATTO dye (e.g., ATTO 532 or 655), and Cy5. Exemplary fluorescent dyes can further include dyes that are used in, or compatible with, two- or four-channel SBS chemistries and workflows.

Exemplary label molecules may be selected from xanthene dyes, including fluoresceins, and rhodamine dyes. Many suitable forms of these compounds are widely available commercially with substituents on their phenyl moieties which can be used as the site for linking to an affinity reagent. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate, and 2-p-toluidinyl-6-naphthalene sulfonate. Other labels include 3-phenyl-7-isocyanatocoumarin; acridines, such as 9-isothiocyanatoacridine and acridine orange; N-(p-(2-benzoxazolyl)phenyl)maleimide; benzoxadiazoles; stilbenes; pyrenes; and the like.

In some embodiments, labels are selected from fluorescein and rhodamine dyes. These dyes and appropriate linking methodologies are described in many references, e.g., Khanna et al. (cited above); Marshall, *Histochemical J.*, 7:299-303 (1975); Menchen et al., U.S. Pat. No. 5,188,934; Menchen et al., European Pat. App. No. 87310256.0; and Bergot et al., International Application PCT/US90/05565. Fluorophores that can be used as detectable labels for affinity reagents or nucleoside analogues include, but are not limited to, rhodamine, cyanine 3 (Cy 3), cyanine 5 (Cy 5), fluorescein, Vic™, Liz™, Tamra™, 5-Fam™, 6-Fam™, 6-HEX, CAL Fluor Green 520, CAL Fluor Gold 540, CAL Fluor Orange 560, CAL Fluor Red 590, CAL Fluor Red 610, CAL Fluor Red 615, CAL Fluor Red 635, and Texas Red (Molecular Probes).

By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 1972; and Haugland, Handbook of Fluorescent Probes and Research Chemicals, Molecular Probes, Eugene (2005).

4.3.2 Enzymatically Labeled Affinity Reagents

In one approach the affinity reagent (e.g., antibody or affimer) is enzymatically labeled and, in the presence of substrate, the enzyme associated with an affinity reagent bound to a primer extension product produces a detectable signal. For example and without limitation, enzymes include peroxidase, phosphatase, luciferase, etc. In one approach the enzyme is a peroxidase. In one approach the affinity reagent (e.g., antibody or affimer) is directly labeled enzymatically In one approach, for example, an antibody or other affinity reagent is labeled using peroxidase, such as horseradish peroxidase (HRP) or a phosphatase, such as an alkaline phosphatase (Beyzavi et al., Annals Clin Biochem 24:145-152, 1987). In one approach, the affinity reagent is coupled to (or is part of a fusion protein with) luciferase or other protein that can be used to produce a chemiluminescent signal. In another approach, the affinity reagent can be coupled/fused to an enzyme system that is selected to produce a non-optical signal, such as a change in pH where protons can be detected, for example, by ion semiconductor sequencing (e.g., Ion Torrent sequencers; Life Technologies Corporation, Grand Island, N.Y.). Use of enzyme labeled affinity reagents has certain advantages, including high sensitivity resulting from signal amplification and the ability to tailor the sequencing method to a variety of instruments. Enzyme reporter systems are reviewed in Rashidian et al., *Bioconjugate Chem.* 24:1277-1294, 2013.

4.3.3 Antibody Fusion Affinity Reagents

In addition, fusions directly linking recombinant antibody fragments, e.g., single-chain Fv fragments (scFvs) with reporter proteins (Skerra and Pluckthun, Science 240:1038-1041, 1988; Bird et al., Science 242:423-426, 1988; Huston et al., Methods Enzymol 203:46-88, 1991; Ahmad et al., Clin. Dev. Immunol. 2012:1, 2012) may be used. For example, photoproteins with bioluminescent properties, e.g., luciferases and aequorin, may be used as reporter proteins in fusion proteins with antibody fragments, epitope peptides and streptavidin, for example (Oyama et al., Anal Chem 87:12387-12395, 2015; Wang et al., Anal Chim Acta 435: 255-263, 2001; Desai et al., Anal Biochem 294:132-140, 2001; Inouye et al., Biosci Biotechnol Biochem 75:568-571, 2011).

4.4 Indirect and Direct Detection Methods

An affinity reagent may be directly labeled (e.g., by conjugation to the label, e.g., via a covalent bond, to a fluorophore) or indirectly labeled, e.g., by binding of a labeled secondary affinity reagent that binds a primary affinity reagent directly bound to the extended primer with a 3' NLRT. Unlabeled primary affinity reagents bind the target nucleotide and labeled secondary affinity reagents (e.g., antibodies, aptamers, affimers or knottins) bind the primary affinity reagents. In some approaches the primary and/or secondary affinity reagent is an antibody. For example, in one approach the affinity reagent is a "primary" antibody (e.g., rabbit anti-NLRT-C antibody) and the secondary binder is a labeled anti-primary antibody (e.g., dye-labeled goat anti-rabbit antibody). In some approaches, use of a secondary affinity reagent provides advantageous signal amplification.

In the case of indirect detection, the assay comprises two distinct parts: first, there is a period of incubation (usually one hour) with the unlabeled primary antibody, during the antibody binds to the antigen (assuming of course that the antigen is present). Excess unbound primary antibody is then washed away and a labeled secondary reagent is added. After a period of incubation (again one hour), excess secondary reagent is washed away and the amount of label associated with the primary antibody (i.e., indirectly via the secondary reagent) is quantified. The label usually results in the production of a colored substance or an increase in the amount of light emitted at a certain wavelength, if the antigen is present. In the absence of antigen there is no binding of the primary antibody and no binding of the secondary reagent, and thus no signal. With direct detection, the prior covalent attachment of the label to the primary antibody means that only a single incubation step with the antigen is required and only a single round of wash steps, as opposed to two rounds of incubation and wash steps with indirect detection.

4.4.1 Secondary Antibody Specificity

Primary and secondary antibodies may be selected to distinguish multiple antigens (e.g., to distinguish RT-A, RT-C, RT-G and RT-T from each other). unlabeled primary antibodies (typically monoclonal or engineered antibodies) may have different isotypes and/or have sequences characteristic of different species (e.g., polyclonal antibodies raised in different animals or corresponding monoclonal antibodies or other affinity reagents). In such cases, labeled secondary (i.e., anti-primary) antibodies for each antigen be specific for the appropriate isotype or species sequence. For example, primary antibodies of isotypes IgG1, IgG2a, IgG2b, and IgG3 can be used with isotype-specific secondary antibodies.

4.4.2 Precombined Primary and Secondary Antibodies

Primary and secondary antibodies or other agents may be added to a sequencing array sequentially, simultaneously, may be precombined under conditions in which the secondary antibody(s) bind to the primary antibody and added to the array as a complex. See FIG. 2 and Example 7.

4.5 One-, Two-, Three-, or Four-Color Sequencing

Sequencing using methods of the invention may be two-, three-, or four-color sequencing. In one approach (four-color sequencing) each affinity reagent is directly or indirectly labeled with a different detectable label (e.g., a fluorescent dye) or combination of labels producing a unique signal. It will be appreciated that when a single antigen is recognized with two or more dyes (or other labels) it is possible, but not necessary, to label a single affinity reagent molecule with both (or all) of the dyes or other labels. Rather, a portion (e.g., 50%) of the affinity reagent molecules specific for the single antigen can be labeled with one dye and another portion (e.g., 50%) of the affinity reagent molecules specific for the single antigen can be labeled with the other dye.

According to one such method, an array is provided that comprises single-stranded nucleic acid templates disposed at positions on a surface. Sequencing by extension, or SBS, is performed in order to determine the identity of nucleotides at detection positions in nucleic acid templates in multiple sequencing cycles by: (i) binding (or incorporating) an unlabeled complementary nucleotide (NLRT) to a nucleotide at a detection position, (ii) labeling the NLRT by binding to it a directly or indirectly labeled affinity reagent that specifically binds to such an NLRT; (iii) detecting the presence or absence of a signal(s) associated with the complementary NLRT at the detection position, the signal resulting from the label (e.g., a fluorescent signal); wherein (1) detecting a first signal and not a second signal at the detection position identifies the complementary NLRT as selected from NLRT-A, NLRT-T, NLRT-G and NLRT-C; (2) detecting the second signal and not the first signal at the detection position identifies the complementary NLRT as an NLRT selected from NLRT-A, NLRT-T, NLRT-G or NLRT-C that is different from the NLRT selected in (1); (3) detecting both the first signal and the second signal at the detection position identifies the complementary NLRT as an NLRT selected from NLRT-A, NLRT-T, NLRT-G and NLRT-C that is different from nucleotides selected in (1) and (2); and (4) detecting neither the first signal nor the second signal at the position identifies the complementary NLRT as an NLRT selected from NLRT-A, NLRT-T, NLRT-G and NLRT-C that is different from the nucleotides selected in (1), (2) and (3); and (iii) deducing the identity of the nucleotide at the detection position in the nucleic acid template based on the identity of the complementary NLRT.

Another such method comprises: providing a plurality of nucleic acid templates each comprising a primer binding site and, adjacent to the primer binding site, a target nucleic acid sequence; performing sequencing reactions on the plurality of different nucleic acid templates by hybridizing an primer to the primer binding site and extending individual primers by one nucleotide per cycle in one or more cycles of sequencing-by-synthesis using a set of NLRTs and a corresponding set of affinity reagents, e.g.: (i) first NLRTs and first affinity reagents that specifically bind to the first NLRTs and that comprise a first label; (ii) second NLRTs and second affinity reagents that specifically bind to the second NLRTs and that comprise a second label; (iii) third NLRTs and third affinity reagents that specifically bind to the third NLRTs and that comprise both the first label and the second label; and (iv) fourth NLRTs and fourth affinity reagents that specifically bind to the fourth NLRTs and that comprise neither the first label nor the second label, wherein the first label and the second label are distinguishable from each other; and in each cycle of sequencing-by-synthesis, determining the identities of NLRTs at the detection positions by detecting the presence or absence of the first label and the presence or absence of the second label to determine the target nucleic acid sequences. An alternative to the foregoing method is to use a mixture of third affinity reagents that specifically bind to the third NLRTs, some of which comprise the first label and some of which comprise the second label (e.g., an equal mixture).

In a one-color sequencing method, the affinity reagents include a detectable label that is present at distinguishable intensities. For example, according to one such embodiment, such a method comprises: such method comprises: providing a plurality of nucleic acid templates each comprising a primer binding site and, adjacent to the primer binding site, a target nucleic acid sequence; performing sequencing reactions on the plurality of different nucleic acid templates by hybridizing a primer to the primer binding site and extending individual primers by one nucleotide per cycle in one or more cycles of sequencing-by-synthesis using a set of NLRTs and a corresponding set of affinity reagents, e.g.: (i) first NLRTs and first affinity reagents that specifically bind to the first NLRTs and that comprise a label at a first intensity; (ii) second NLRTs and second affinity reagents that specifically bind to the second NLRTs and that comprise the label at a second intensity; (iii) third NLRTs and third affinity reagents that specifically bind to the third NLRTs and that comprise the label at a third intensity; and (iv) fourth NLRTs and fourth affinity reagents that specifically bind to the fourth NLRTs and that are unlabeled (or, alternatively, the affinity reagent set includes only the first, second and third affinity reagent and does not include a fourth affinity reagent that binds to the fourth NLRT); and in each cycle of sequencing-by-synthesis, determining the identities of NLRTs at the detection positions by detecting the presence and intensity (or absence) of the label to determine the target nucleic acid sequences.

In another approach, affinity affinity reagents are used that are labeled with one or the same number of molecules of a single dye yet discriminate among the four NLRTs as a result of different binding efficiencies (i.e., the average number of affinity reagents that are bound to a single spot on an array, e.g., 10% of all copies of the target DNA molecule for NLRT-A, 30% for NLRT-T, and 60% for NLRT-C (and zero percent or little detectable binding for NLRT-G). In one approach, the targets have the same blocking group and affinity reagents are selected that have different affinities for their target. In another one approach blocking groups may be modified with small chemical changes to tune the efficiency of binding of the same affinity reagent, thus generating base specific levels of signal. For example, an unmodified blocking group may produce the highest signal (100% of signal), a blocking group with modification 1 may produce a lower level of signal (e.g. 50%),), a blocking group with modification 2 may produce a still lower signal with even less (25%), etc.

In a related approach, using 2 different blocking groups (azidomethyl and cyanoethoxymethyl) and one chemical variant of each (azidomethyl-prime and cyanoethoxymethyl-prime) and two antibodies can be used for 2-color sequencing (2-colors×2-intensities). For illustration,

| | |
|---|---|
| azidomethyl-dA | Affinity Agent 1, color 1, low intensity (0-40%) |
| azidomethyl-prime-dC | Affinity Agent 1, color 1, high intensity (60-100%) |
| cyanoethoxymethyl-dG | Affinity Agent 2, color 2, low intensity (0-40%) |
| cyanoethoxymethyl-prime-dT | Affinity Agent 2, color 2, high intensity (60-100%) |

In one embodiment, Affinity Agent 1, color 1, low intensity has an signal intensity close to zero and Affinity Agent 2, color 2, low intensity has a higher signal intensity (25-40%).

In a related approach embodiment, 2-color sequencing can be carried out in which a single species of nucleotide is uses as a mixture of nucleotides in which a portion are labeled with one blocking group and the remainder are labeled with the other blocking group. For illustration:

| | |
|---|---|
| azidomethyl-dA | Blocking group 1 |
| cyanoethoxymethyl-dG | Blocking group 2 |
| azidomethyl-prime-dC | Mixture with 70% of nucleotides having blocking group 1 and 30% of nucleotides having blocking group 2 |
| cyanoethoxymethyl-prime-dT | Mixture with 30% of nucleotides having blocking group 1 and 70% of nucleotides having blocking group 2 |

In another approach, only one affinity reagent is used. Nucleotide mixtures with different proportions of the blocking group recognized by the affinity reagent are used to generate distinguishable levels of signal. The balance of nucleotides in the mixtures have a blocking group with no corresponding affinity reagent. For illustration:

| | |
|---|---|
| dA | 0% Blocking group 1, 100% blocking group 2 |
| dG | 25% Blocking group 1, 75% blocking group 2 |
| dC | 50% Blocking group 1, 50% blocking group 2 |
| dT | 100% Blocking group 1, 0% blocking group 2 |

In another embodiment the antibody could recognize two bases (a nucleotide dimer) where the downstream base is modified with the addition of a cleavable or un-cleavable group.

In another embodiment the last-incorporated base is identified by the binding of two affinity reagents in combination: one affinity reagent specifically recognizes and binds to the nucleobase, and the second affinity reagent specifically recognizes and binds to the blocking group. Only when both affinity reagents bind and/or are in spatial proximity, can a determination of the identity of the terminal base be made such as when the two affinity reagents include a FRET donor-acceptor pair as their respective "labels." Alternatively, the binding of one of the affinity reagents could lead to a conformational change that allows or enhances binding of the second affinity reagent.

The nucleoside analogues described herein can be used in a variety of sequencing methods. For example, the analogues can be used in one label (sometimes called "no-label"), two-label, three-label, or four-label sequencing methods, in which unlabeled analogues are paired with affinity reagents directly or indirectly labeled according to a one-, two-, three-, or four-label scheme.

Exemplary one-label sequencing methods include, but are not limited to, methods in which nucleoside analogues having different nucleobases (e.g., A, C, G, T) are delivered in succession and incorporation is detected by detecting the presence or absence of the same signal or label for each different nucleobase. Thus, one-label methods are sometimes known as one-color methods because the detection signal and/or label is the same for all nucleobases, even though it may differ in intensity (or be absent) for each nucleoside analogue. For example, incorporation of a nucleoside into a primer by DNA polymerase mediated template directed polymerization can be detected by detecting a pyrophosphate cleaved from the nucleoside pyrophosphate. Pyrophosphate can be detected using a coupled assay in which ATP sulfurylase converts pyrophosphate to ATP, in the presence of adenosine 5' phosphosulfate, which in turn acts as a substrate for luciferase-mediated conversion of luciferin to oxyluciferin, generating visible light in amounts proportional to ATP generation.

According to another embodiment, two-label, or two-color, sequencing can be performed using the RTs and affinity reagents described herein, using two distinguishable signals in a combinatorial fashion to detect incorporation of four different RTs. Exemplary two-label systems, methods, and compositions include, without limitation, those described in U.S. Pat. No. 8,617,811, the contents of which are hereby incorporated by reference in the entirety for all purposes and particularly for disclosure related to two-label sequencing. Briefly, in two-label sequencing, incorporation of a first RT (e.g., RT-A) is detected by labeling the newly incorporated RT by specific binding of a first affinity reagent that includes a first label, then detecting the presence of the first label. Incorporation of a second RT (e.g., RT-C) is detected by labeling the second RT by specific binding of a second affinity reagent that includes a second label, then detecting the presence of the second label. Incorporation of a third RT (e.g., RT-T) is detected by labeling the third RT by specific binding of a third affinity reagent that includes both the first and the second label, then detecting the presence of both the first and second label; and, incorporation of a fourth RT (e.g., RT-G) is detected by detecting the absence of both first and second labels, whether this results from binding of a fourth affinity reagent that is unlabeled or from the fact that no fourth affinity reagent is included in the affinity reagent set that is used. In two-color sequencing the first label is distinguishable from the second label and the combination of the first and second label can be distinguished from the first and second label taken alone.

According to another embodiment, three-label sequencing can be performed using a first RT labeled by specific binding of an first affinity reagent that includes a first label, a second RT labeled by specific binding of an second affinity reagent that includes a second label, a third RT labeled by specific binding of a third affinity reagent that includes a third label. For the fourth RT, the corresponding affinity reagent is omitted from the affinity reagent set, or is unlabeled, or includes a combination of two or more of the first, second, and third labels (or a mixture of affinity reagents that are labeled with a different one of the labels and that specifically bind to the fourth RT). The first, second and third labels are distinguishable from each other.

Similarly, four-label sequencing can employ a first NLRT that is labeled by specific binding of a first affinity reagent that includes a first label, a second NLRT that is labeled by specific binding of a second affinity reagent that includes a second label, a third NLRT that is labeled by specific binding of a third affinity reagent that includes a third label, and a fourth NLRT that is labeled by specific binding of a fourth affinity reagent that includes a fourth label. Again, the first, second, third and fourth labels are distinguishable from each other.

4.6 Affinity Reagents Used In Combination

Affinity reagents that recognize different epitopes of a single NLRT may be used in combination. For example a first affinity reagent that recognizes the nucleobase portion of the incorporated NLRT may be used with a second affinity reagent that recognizes a blocking group. Staining may be done simultaneously or sequentially. In sequential staining the second affinity reagent may be applied while the first affinity reagent remains bound to the NLRT or after removal of the first affinity reagent in the case of re-probing (discussed below).

4.7 Affinity Reagent Sets

"Affinity reagent sets" are used to label RTs used in SBS. For example, in one embodiment, for an RT set that includes four RTs (RT-A, RT-T, RT-C and RT-G), there could be a corresponding affinity reagent set of four affinity reagents, each specifically recognizing and binding to one of the RTs (antiA, antiT, antiC and antiG). Affinity reagent sets describe combinations of affinity reagents that can be (i) provided in kit form, as a mixture or in separate containers and/or (ii) contacted with, or combined on, a sequencing array (e.g., within a sequencing flow cell).

According to one embodiment, each member of an affinity reagent set has a different, distinguishable detectable label, as in four-color SBS.

According to another embodiment, one member of an affinity reagent set is unlabeled, while the other members are labeled. Alternatively, the affinity reagent set could simply exclude the unlabeled affinity reagent and include only the labeled affinity reagents.

For example, according to one embodiment, one affinity reagent is labeled with a first label (e.g., antiA); a second affinity reagent is labeled with a second label (e.g., antiT); a third affinity reagent is labeled with a third label (e.g., antiC); and a fourth affinity reagent is unlabeled or simply excluded from the affinity reagent set (e.g., antiG). Such an affinity reagent set would be useful for three-color sequencing.

According to another embodiment, one affinity reagent (e.g., antiA) is labeled with a first label; a second affinity reagent (e.g., antiT) is labeled with a second label; a third affinity reagent (e.g., antiC) is labeled with both the first label and the second label; and a fourth affinity reagent (e.g., antiG) is unlabeled (or excluded from the affinity reagent set). Alternatively, the third affinity reagent may include a mixture of affinity reagent molecules, all of which specifically bind to a particular base (e.g., all are antiC), but some include the first label and some include the second label. Such affinity reagent sets would be useful for two-color sequencing.

According to another embodiment, only a single detectable label is used (or a single combination of two or more labels), but differs in intensity among members of the set, such as when the affinity reagent includes differing amounts of the label (or of at least one label of a combination of two or more labels). For example, in one embodiment, a first affinity reagent (e.g., antiA) is labeled with a label at a first intensity; a second affinity reagent (e.g., antiT) is labeled with the same label but at a second intensity; a third affinity reagent (e.g., antiC) is labeled with the same label but at a third intensity; and a fourth affinity reagent (e.g., antiG) is unlabeled (or the fourth affinity reagent is excluded from the affinity reagent set). In another embodiment, a first affinity reagent (e.g., antiA) is labeled with a first label at a first intensity and a second label; a second affinity reagent (e.g., antiT) is labeled with the same first label but at a second intensity and the same second label; a third affinity reagent (e.g., antiC) is labeled with the same first label but at a third intensity and the same second label; and a fourth affinity reagent (e.g., antiG) is unlabeled, is labeled only with the second label, or is excluded from the affinity reagent set.

4.8 Reaction Mixtures

Nucleoside analogues (e.g., NLRTs) and oligo- or polynucleotides containing such nucleoside analogues or reaction products thereof can be used as a component of a reaction mixture. For example, such components can be used in reaction mixtures for nucleic acid sequencing (e.g., SBS). Exemplary reaction mixtures include, but are not limited to, those containing (a) template nucleic acid; (b) polymerase; (c) oligonucleotide primer; (d) a 3'-O reversibly blocked nucleoside analogue, or a mixture of 3'-O reversibly blocked nucleoside analogues having structurally different nucleobases; and (e) a labeled affinity reagent. Exemplary sequencing reaction mixtures of the invention include, but are not limited to, arrays comprising a plurality of different template nucleic acids immobilized at different locations on the array; (b) polymerase; (c) oligonucleotide primer; (d) and one or a mixture of NLRTs. Exemplary sequencing reaction mixtures of the invention include, but are not limited to, arrays comprising a plurality of different template nucleic acids immobilized at different locations on the array; (b) growing DNA strands (GDS) (which may comprise a 3' NLRT; and (c) one or more affinity reagents (e.g., an affinity reagent set as described hereinabove).

5. Template Nucleic Acids and Nucleic Acid Arrays

In various embodiments, the template polynucleotide is DNA (e.g., cDNA, genomic DNA, transcriptome or microbiome DNA, amplification products, etc.) or RNA. In various embodiments, the polynucleotide is either double stranded or single stranded.

In some embodiments, the template nucleic acid is immobilized on a solid surface. In some embodiments, the template nucleic acid is immobilized on a substrate (e.g., a bead, flow cell, pad, channel in a microfluidic device and the like). The substrate may comprise silicon, glass, gold, a polymer, PDMS, and the like.

In some embodiments, the template nucleic acid is immobilized or contained within a droplet (optionally immobilized on a bead or other substrate within the droplet).

In some embodiments, the template nucleic acid is an immobilized DNA concatemer comprising multiple copies of a target sequence. In some embodiments, the template nucleic acid is represented as a DNA concatemer, such as a DNA nanoball (DNB) comprising multiple copies of a target sequence and an "adaptor sequence". See PCT Pat. Pub. WO 2007/133831, the content of which is hereby incorporated by reference in its entirety for all purposes. In some embodiments the template is a single polynucleotide molecule. In some embodiments the template is present as a clonal population of template molecules (e.g., a clonal population produced by bridge amplification or Wildfire amplification).

It will be understood that the method is not limited to a particular form of template, and the template can be any template such as, for example, a DNA concatemer, a dendrimer, a clonal population of templates (e.g., as produced by bridge amplification or Wildfire amplification) or a single polynucleotide molecule. Thus, the specification should be read as if each reference to a template can alternatively refer to a concatemer template, a dendrimer, a clonal population of, e.g., short linear templates, a single molecule template (e.g., in a zero-mode waveguide), and templates in other forms.

Suitable template nucleic acids, including DNBs, clusters, polonys, and arrays or groups thereof, are further described in U.S. Pat. Nos. 8,440,397; 8,445,194; 8,133,719; 8,445,196; 8,445,197; 7,709,197; 12/335,168; 7,901,891; 7,960,104; 7,910,354; 7,910,302; 8,105,771; 7,910,304; 7,906,285; 8,278,039; 7,901,890; 7,897,344; 8,298,768; 8,415,099; 8,671,811; 7,115,400; 8,236,499, and U.S. Pat. Pub. Nos. 2015/0353926; 2010/0311602; 2014/0228223; and 2013/0338008, all of which are hereby incorporated by reference in their entirety.

In one aspect the invention provides a DNA array comprising: a plurality of template DNA molecules, each DNA molecule attached at a position of the array, a complementary DNA sequence base-paired with a portion of the template DNA molecule at a plurality of the positions, wherein the complementary DNA sequence comprises at its 3' end an incorporated first reversible terminator deoxyribonucleotide; and a first affinity reagent bound specifically to at least some of the first reversible terminator deoxyribonucleotides. In one approach the DNA array comprises primer extension products with 3' terminal nucleotides comprising A, T, G or C nucleobases or analogs thereof, and affinity reagents bound to the primer extension products.

6. Kits

Kits may be provided for practicing the invention. As described above, NLRTs and NLRT sets may be provided in kit form. Also as described, above, affinity reagents and affinity reagent sets may be provided in kit form. Also contemplated are kits comprising both NLRTs and NLRT sets and affinity reagents or affinity reagent sets. For example, the invention provides kits that include, without limitation (a) a reversible terminator nucleotide (RT) or RT set that includes one, two, three, four or more different individual RTs; (b) a corresponding affinity reagent or affinity reagent set that includes one, two, three, four or more affinity reagents, each of which is specific for one of the RTs; and (c) packaging materials and or instructions for use.

According to another embodiment, such a kit comprises a plurality of the RTs, wherein each RT comprises a different nucleobase, and a plurality of affinity reagents, wherein each affinity reagent binds specifically to one of the RTs.

In one example, the invention provide a kit comprising (a) a reversible terminator nucleotide as herein described that may be incorporated into a primer extension product; (b) a first affinity reagent that is binds specifically to the reversible terminator nucleotide when incorporated at the 3' terminus of a primer extension product; and (c) packaging for (a) and (b). In one approach, the kit contains a plurality of reversible terminator deoxyribonucleotides, wherein each reversible terminator deoxyribonucleotide comprises a different nucleobase, and a plurality of first affinity reagents, wherein each first affinity reagent binds specifically a different one of the reversible terminator deoxyribonucleotides. In some embodiments the first affinity reagents are detectably labeled and can be distinguished from each other. In some embodiments the kit comprises secondary affinity reagents. In some embodiments the first and/or second affinity reagents are antibodies.

In one example, the reversible terminator deoxyribonucleotide has the structure of Formula I:

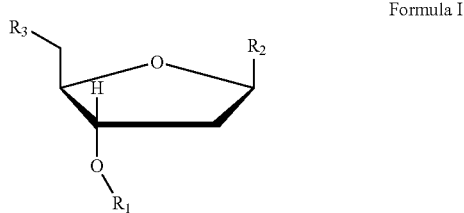

Formula I wherein $R_1$ is a 3'-O reversible blocking group; $R_2$ is a nucleobase selected from adenine (A), cytosine (C), guanine (G), thymine (T), and analogues thereof; and $R_3$ comprises of one or more phosphates.

7. Applications

In addition to the SBS applications described above, the novel affinity reagents, NLRTs, kits and methods described herein may be used in many other applications, such as detecting what is at the end of naturally or experimentally fragmented DNA (or in DNA gaps); capturing oligonucleotides or polynucleotides with a specific end-base (end of molecule or end within the gap of a strand) with or without specific modification. Both 5' or 3' end/gap bases may be detected. Affinity reagents may be used for ligation, hybridization, and other detection.

It will be appreciated that methods of the invention may also be used for direct RNA sequencing.

8. Methods

8.1 Removal of Blocking Groups, Removal of Affinity Reagents, and Detection Removal of blocking groups and affinity reagents can occur simultaneously. In one approach an array is exposed to conditions in which of blocking groups and affinity reagents are removed simultaneously. In one the array is contacted with a solution with a combination of agents some of which result in removal of the affinity reagents (e.g., high salt, small molecule competitors, protease, etc.) combined with agents that cleave the blocking group.

In some cases, removal of the 3' blocking group results in removal of the affinity reagent. Without intending to be bound by a particular mechanism, it is believed that in these cases, removal of the blocking moiety destroys the epitope required for binding of the antibody or other affinity reagent.

In a different approach, the removal of the affinity reagent and blocking group is uncoupled, such that the affinity reagent is removed but the blocking group is not cleaved from the nucleotide sugar. This is useful when reprobing is desired. See FIG. 2, Section 9, below, and Example 11.

It will be appreciated that conditions for removal conditions for removal of affinity reagents and/or blocking groups will be selected to preserve the integrity of the DNA being sequenced.

8.1.1 Removal of Blocking Groups

Nucleoside analogues or NLRTs include those that are 3'-O reversibly blocked. In some aspects, the blocking group provides for controlled incorporation of a single 3'-O reversibly blocked NLRT at the 3'-end of a primer, e.g., a GDS extended in a previous sequencing cycle.

generally, in each sequencing cycle in which NLRTs are used, the blocking group is removed and the affinity reagent is disassociated from the NLRT. These steps may be carried our concurrently. For example, a azidomethyl blocking group can be removed by treatment with phosphine (a widely used process) and an antibody affinity reagent can be removed by treatment with a low pH (e.g., 100 mM glycine pH 2.8) or high pH (e.g., 100 mM glycine pH 10), high salt, or chaotropic stripping buffer. In an embodiment, a single treatment or condition can be used to remove both the NLRT and the affinity reagent (e.g., phosphine in a high salt buffer). In some embodiments, removal of the blocking group results in disassociation of the affinity reagent if, for example, the blocking group is required for affinity reagent binding.

The 3'-O reversible blocking group can be removed by enzymatic cleavage or chemical cleavage (e.g., hydrolysis). The conditions for removal can be selected by one of ordinary skill in the art based on the descriptions provided herein, the chemical identity of the blocking group to be cleaved, and nucleic acid chemistry principles known in the art. In some embodiments, the blocking group is removed by contacting the reversibly blocked nucleoside with a reducing agent such as dithiothreitol (DTT), or a phosphine reagent such as tris(2-carboxyethyl)phosphine (TCEP), tris(hydroxymethyl)phosphine (THP), or tris(hydroxypropyl) phosphine. In some cases, the blocking group is removed by washing the blocking group from the incorporated nucleotide analogue using a reducing agent such as a phosphine reagent. In some cases, the blocking group is photolabile, and the blocking group can be removed by application of, e.g., UV light. In some cases, the blocking group can be removed by contacting the nucleoside analogue with a transition metal catalyzed reaction using, e.g., an aqueous palladium (Pd) solution. In some cases, the blocking group can be removed by contacting the nucleoside analogue with an aqueous nitrite solution. Additionally, or alternatively, the blocking group can be removed by changing the pH of the solution or mixture containing the incorporated nucleotide analogue. For example, in some cases, the blocking group can be removed by contacting the nucleoside analogue with acid or a low pH (e.g., less than 4) buffered aqueous solution. As another example, in some cases, the blocking group can be removed by contacting the nucleoside analogue with base or a high pH (e.g., greater than 10) buffered aqueous solution.

3'-O reversible blocking groups that can be cleaved by a reducing agent, such as a phosphine, include, but are not limited to, azidomethyl. 3'-O reversible blocking groups that can be cleaved by UV light include, but are not limited to, nitrobenzyl. 3'-O reversible blocking groups that can be cleaved by contacting with an aqueous Pd solution include, but are not limited to, allyl. 3'-O reversible blocking groups that can be cleaved with acid include, but are not limited to, methoxymethyl. 3'-O reversible blocking groups that can be cleaved by contacting with an aqueous buffered (pH 5.5) solution of sodium nitrite include, but are not limited to, aminoalkoxyl.

8.1.2 Removal of Affinity Reagents

Antibody-based affinity reagents can be removed by low pH, high pH, high or low salt, or denaturing agents such as a chaotropic stripping buffer. Other classes of affinity reagents (e.g., aptamers) can be removed by any means known in the art. In addition, affinity reagents, such as antibodies, can be removed by introducing an agent that competes with the bound epitope for affinity reagent binding, for example as illustrated in Example 10 below.

In addition, affinity reagents may also be removed by disrupting the ability of the agent to bind the incorporated NLRT. Typically this occurs when the 3' blocking group is cleaved from the incorporated nucleotide analog. In cases in which the affinity reagent binding depends on the presence of the blocking group (for example, in cases in which an epitope recognized by a 1° antibody includes the blocking group or a portion thereof) removal of the blocking group results in release of the affinity reagent as well.

Simultaneous removal of affinity reagents and blocking groups also may occur simultaneously may also be effected by addition of a solution comprising a blocking group cleaving component (e.g., a phosphine reagent) and an affinity reagent releasing agent (e.g., high salt).

alternatively, an affinity reagent may be removed without removing the 3'blocking group. This approach is useful when reprobing is desired (as described in Section 9, below).

8.1.3 Detection

Methods for detecting a binding event will vary with the nature of the detectable label(s) being used and are well known in the art. Detection (e.g., of a fluorescent signal) is generally performed prior to removal of the blocking group. However, detection can be performed either before or after removal of the blocking group as long as the labeled affinity reagent remains bound.

8.2 Antibody Production

For example, small compounds (drugs or peptides) are not sufficiently complex by themselves to induce an immune response or be processed in a manner that elicits production of specific antibodies. For antibody production to be successful with small antigens, they must be chemically conjugated with immunogenic carrier proteins such as keyhole limpet hemocyanin (KLH). Adjuvants can be mixed and injected with an immunogen to increase the intensity of the immune response. Carrier protein conjugation, use of adjuvants and other issues relating to preparation of samples for injection are described in this section on antibody production. Standard procedures for generating, purifying and modifying antibodies for use as antigen-specific probes may be used. See, e.g., Harlow and Lane, "Antibodies: A Laboratory Manual" (1988) and Harlow and Lane, "Using Antibodies: A Laboratory Manual" (1999).

Haptens: Small molecules that are used as antigens are referred to as haptens. They are able to act as recognition sites for production of specific antibodies but cannot by themselves stimulate the necessary immune response. Haptens can be made immunogenic by coupling them to a suitable carrier molecule.

Epitopes: An epitope is the specific site on an antigen to which an antibody binds. For very small antigens, practically the entire chemical structure may act as a single epitope. Depending on its complexity and size, an antigen may effect production of antibodies directed at numerous epitopes. Polyclonal antibodies are mixtures of serum immunoglobulins and collectively are likely to bind to multiple epitopes on the antigen.

Keyhole Limpet Hemocyanin (KLH). Keyhole limpet hemocyanin (KLH) is the most widely used carrier protein.

Bovine Serum Albumin. Bovine serum albumin (BSA; 67 kDa) belongs to the class of serum proteins called albumins.

8.3 Immunization Protocols

Immunization protocols are well known and only generally described here. See Example 2, below for additional descriptions. The concentration of the immunogen before mixing with adjuvant will ultimately determine the amount of conjugate that will be administered per injection. Immunization Schedule for Mice: Day 0: Collect pre-immune serum from the mouse to use as a blank when performing ELISA screening after immunization. Store frozen. Inject 50 to 100 μg of immunogen (equal to 100 to 200 μL of antigen-adjuvant mixture) per mouse. Typical routes of injection include intraperitoneal (i.p.) or subcutaneous (s.c.). One or two such injections may be made per animal. Day 14: Boost with an equivalent amount of immunogen in adjuvant. Day 21: Test bleed and assay antibody response by ELISA. (Typically, mice are bled under anesthesia through the tail vein or the retro-orbital plexis). Day 28: Boost again if necessary. Continue with a similar schedule of alternating boosts and test bleeds until a satisfactory response is observed. For monoclonal antibody production, inject either i.p. or intravenously (i.v.) 4 to 5 days before fusion with the immunogen dissolved in saline (no adjuvant).

Immunization Schedule for Rabbits: Day 0: Collect pre-immune serum from the rabbit to use as a blank when performing ELISA after immunization. Store frozen. Inject 100 μg of immunogen (equal to about 200 μL of the antigen adjuvant mixture) into each of 8 to 10 subcutaneous sites on the back of the rabbit. Other routes of injection may also be used, but this is by far the easiest with the rabbit. Day 14: Boost with an equivalent amount of adjuvant. Day 21: Test bleed and assay antibody response by ELISA. (Typically, rabbits are bled through the ear vein without anesthetic). It is not difficult to collect 5 to 10 mL of blood, which is more than adequate for measuring antibody response. Day 28: Boost again if necessary. Continue with a similar schedule of alternating boosts and test bleeds until a satisfactory response is observed.

General Purification of Immunoglobulins. Because antibodies have predictable structure, including relatively invariant domains, it has been possible to identify certain protein ligands that are capable of binding generally to antibodies, regardless of the antibody's specificity to antigen. Protein A, Protein G and Protein L are three bacterial proteins whose antibody-binding properties have been well characterized. These proteins have been produced recombinantly and used routinely for affinity purification of key antibody types from a variety of species. A genetically engineered recombinant form of Protein A and G, called Protein A/G, is also available. These antibody-binding proteins are available immobilized to beaded agarose resin.

8.4 Affinity Purification of Antibodies:

Various methods are used to enrich or purify a protein of interest from other proteins and components in a crude cell lysate or other sample. The most powerful of these methods is affinity chromatography, also called affinity purification, whereby the protein of interest is purified by virtue of its specific binding properties to an immobilized ligand.

Proteins and other macromolecules of interest can be purified from crude extracts or other complex mixtures by a variety of methods. Selective precipitation is perhaps the simplest method for separating one type of macromolecule from another.

Most purification methods, however, involve some form of chromatography whereby molecules in solution (mobile phase) are separated based on differences in chemical or physical interaction with a stationary material (solid phase). Gel filtration (also called size-exclusion chromatography or SEC) uses a porous resin material to separate molecules based on size (i.e., physical exclusion). In ion exchange chromatography, molecules are separated according to the strength of their overall ionic interaction with a solid phase material (i.e., nonspecific interactions).

By contrast, affinity chromatography (also called affinity purification) makes use of specific binding interactions between molecules. A particular ligand is chemically immobilized or "coupled" to a solid support so that when a complex mixture is passed over the column, those molecules having specific binding affinity to the ligand become bound. After other sample components are washed away, the bound molecule is stripped from the support, resulting in its purification from the original sample.

Each specific affinity system requires its own set of conditions and presents its own peculiar challenges for a given research purpose. Other Protein Methods articles describe the factors and conditions associated with particular purification systems 8.5 Antibody Labeling Antibody Structure and Modification Sites. Antibodies, like other proteins, can be covalently modified in many ways to suit the purpose of a particular assay. Many immunological methods involve the use of labeled antibodies and a variety of reagents have been created to allow labeling of antibodies. Enzymes, biotin, fluorophores and radioactive isotopes are all commonly used to provide a detection signal in biological assays. Understanding the functional groups available on an antibody is the key to choosing the best method for modification, whether that be for labeling, cross-linking or covalent immobilization. Most antibody labeling strategies use one of three targets: (1) Primary amines (—NH2): these occur on lysine residues and the N-terminus of each polypeptide chain. They are numerous and distributed over the entire antibody. (2) Sulfhydryl groups (—SH): these occur on cysteine residues and exist as disulfide bonds that stabilize the whole-molecule structure. Hinge-region disulfides can be selectively reduced to make free sulfhydryls available for targeted labeling. (3) Carbohydrates (sugars): glycosylation occurs primarily in the Fc region of antibodies (IgG). Component sugars in these polysaccharide moieties that contain cis-diols can be oxidized to create active aldehydes (—CHO) for coupling.

Antibody Labeling Methods. Any known method for labeling antibodies may be used in the practice of the present invention. Antibodies like all proteins are composed of amino acids, and the side chain of lysine, which terminates in a primary amine (—NH2), is commonly used to link labels covalently to antibody molecules.

The four main chemical approaches for antibody labeling are summarized below:

1. NHS esters. In the case of fluorescent dye labels it is usual to purchase an activated form of the label with an inbuilt NHS ester (also called a 'succinimidyl ester'). The activated dye can be reacted under appropriate conditions with antibodies (all of which have multiple lysine groups). Excess reactive dye is removed by one of several possible methods (often column chromatography) before the labeled antibody can be used in an immunoassay.

2. Heterobifunctional reagents. If the label is a protein molecule (e.g. horseradish peroxidase [HRP], alkaline phosphatase, or phycoerythrin) the antibody labeling procedure is complicated by the fact that the antibody and label have multiple amines. In this situation it is usual to modify some of the lysines on one molecule (e.g. the antibody) to create a new reactive group (X) and lysines on the label to create another reactive group (Y). A 'heterobifunctional reagent' is used to introduce the Y groups, which subsequently react with X groups when the antibody and label are mixed, thus creating heterodimeric conjugates. There are many variations on this theme and you will find hundreds of examples in the literature on the use of heterobifunctional reagents to create labeled antibodies and other labeled biomolecules.

3. Carbodiimides. These reagents (EDC is one very common example) are used to create covalent links between amine- and carboxyl-containing molecules. Carbodiimides activate carboxyl groups, and the activated intermediate is then attacked by an amine (e.g. provided by a lysine residue on an antibody). Carbodimides are commonly used to conjugate antibodies to carboxylated particles (e.g. latex particles, magnetic beads), and to other carboxylated surfaces, such as microwell plates or chip surfaces. Carbodiimides are rarely used to attach dyes or protein labels to antibodies, although they are important in the production of NHS-activated dyes (see above).

4. Sodium periodate. This chemical cannot be employed with the vast majority of labels but is quite an important reagent in that it is applicable to HRP, the most popular diagnostic enzyme. Periodate activates carbohydrate chains on the HRP molecule to create aldehyde groups, which are capable of reacting with lysines on antibody molecules. Since HRP itself has very few lysines it is relatively easy to create antibody-HRP conjugates without significant HRP polymerization.

In any particular antibody clone, lysines (primary amines) might occur prominently within the antigen binding site. Thus, the lone drawback to this labeling strategy is that it occasionally causes a significant decrease in the antigen-binding activity of the antibody. The decrease may be particularly pronounced when working with monoclonal antibodies or when attempting to add a high density of labels per antibody molecule.

9. Re-Probing

As noted Section 8, above, it is possible according to the invention to uncouple removal of affinity reagents (e.g., antibodies) and the 3' protecting group(s). Because affinity reagents can be removed without removing the blocking moiety, it is advantageously possible to reprobe some or all base positions to increase accuracy of base calling, test the integrity of the chip, or for other reasons. See Example 11, below, and FIG. 2. Any given base position can be probed once and reprobed 0, 1, 2 or more than 2 times. Usually, a single round of reprobing is considered sufficient. Solely for convenience, in a case in which a base position is probed two times, the first round of probing can be referred to as the first-halfcycle and the second round of probing can be referred to as the second-halfcycle.

When reprobing, it is possible to probe each position twice with the same affinity reagent, e.g., same primary antibody. More often, a different affinity reagent is used, such as a different antibody preparation (e.g., a different monoclonal antibody), a different class of affinity reagent (e.g., probing with an antibody in the first-halfcycle and with an aptamer in the second-halfcycle), or an affinity reagent with a different specificity. For example, in the first-half-cycle an array may be probed with anti-A, anti-T, anti-C and anti-G, and in the second-halfcycle the array may be probed with anti-purine and anti-pyrimidine used.

In one approach four NLRTs are blocked using two blocking groups, e.g., azidomethyl-T, azidomethyl-G, cyanoethenyl-C and cyanoethenyl-A and the array is probed once with two affinity reagents (one specific for 3'-O-azidomethyl-2'-deoxyribose and the other specific for 3'-O-cyanoethenyl-2'-deoxyribose) and probed a second time with a different pair of affinity reagents (one specific for purines and one specific for pyrimidines). An address on an array that shows signal characteristic of 3'-O-azidomethyl-2'-deoxyribose and purine would be identified as having a guanine base, and so forth.

10. Sequencing Process

Figure 2:
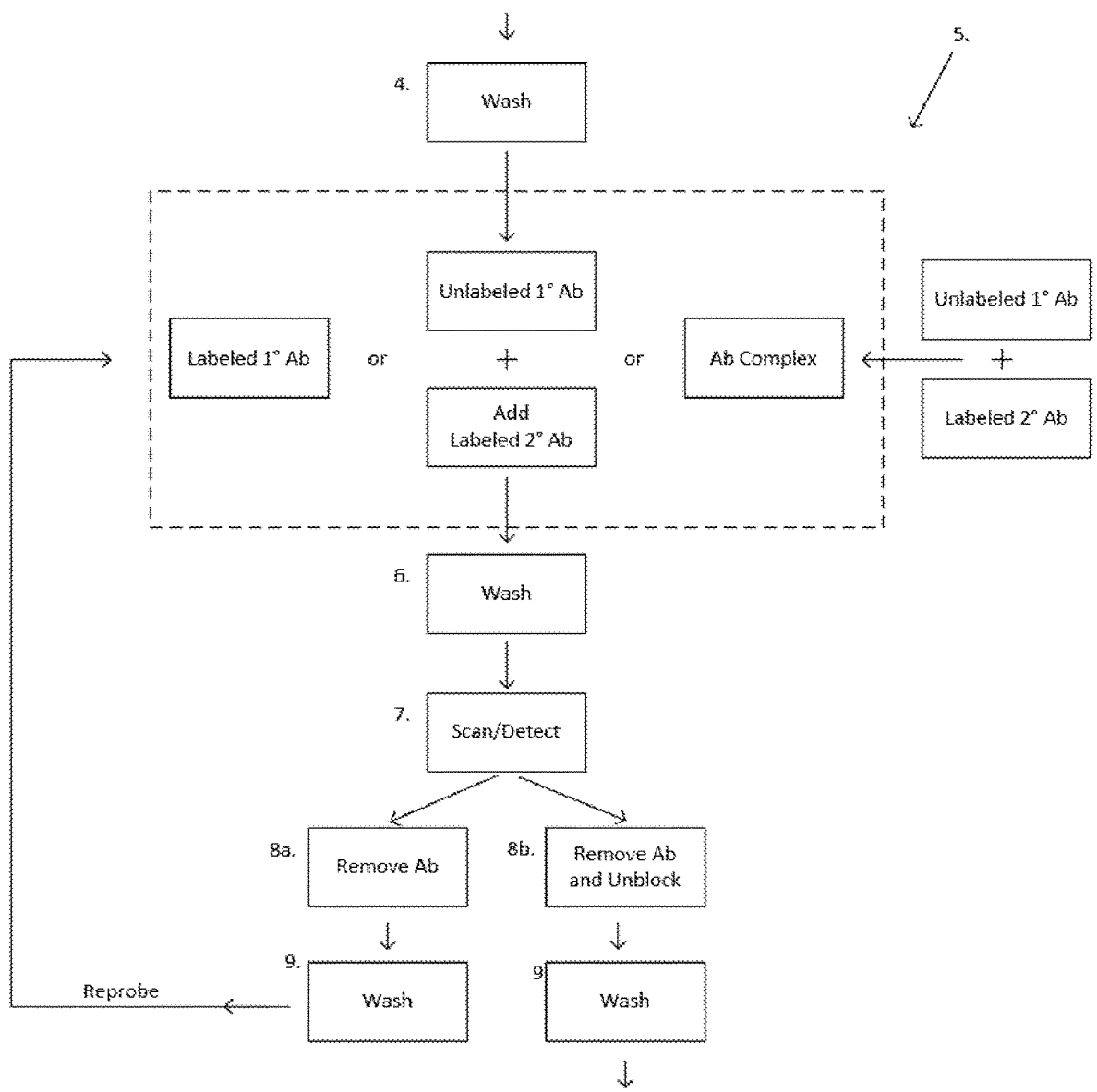
FIG. 2 is a flowchart that illustrates an example of an antibody staining process shown in FIG. 1.

FIGS. 1 and 2 provide additional guidance to the reader, but should not be construed as limiting. For example, when using an affinity reagent to detect a terminal 3'-OH of an extension product (see Section 3.8, above) the blocking group will be removed (Step 8b) prior to antibody staining (Step 5).

As discussed above, in one aspect the invention is directed to a method of sequencing-by-synthesis (SBS) using unlabeled reversible terminator nucleotides. SBS methods are well known including, but not limited to, methods described in references cited herein, each of which is incorporated by reference for all purposes. Typically SBS determines sequence of a single-stranded nucleic acid template immobilized at a position on a surface. As is known to the reader of ordinary skill in the art, usually there are many copies of the template at a position on the surface. For illustration and not limitation, the template copies are most often produced using DNA nanoball (DNB) methods or bridge PCR methods. DNB methods result in a single stranded concatemer with many copies of the template (e.g., genomic DNA sequences and adjacent primer binding sites). Bridge PCR methods result in a clonal cluster of template molecules (e.g., genomic DNA sequences flanked by adaptors which may serve as primer binding sites). In bridge PCR both strands of the template nucleic acid may be present, as separate single strands. It will be understood that references herein to a "template" nucleic acid (i.e., singular grammatical form), or equivalent terms, also refers to a plurality of copies of a template at a given position on a substrate. It will also be recognized that, although reference may be made herein to determining sequence of a template nucleic acid or template nucleic acid sequence (i.e., singular grammatical form), it is contemplated the methods of the invention are carried out using arrays comprising a plurality (often hundreds of millions) of positions containing one or a plurality of template nucleic acid molecules.

As used in this context, "array" is used in the broadest sense and includes, unless otherwise specified, ordered arrays (meaning template binding regions are arranged in an ordered, typically rectilinear, pattern, such as a grid, spiral, or other patterns) and disordered arrays (meaning template binding regions are at random positions). In one approach the identity of templates at any specific position (or "address") on an array may be known prior to sequencing of the templates. More often, the array is a "random array" in which the identity of a templates at a given address is not known prior to sequencing. Unless otherwise specified, in this disclosure "array" is not limited to positions on a planer surface, but can include bead arrays, droplet arrays, and the like.

Various SBS methods can be used with the nucleoside analogues and affinity reagents of the present invention. In some aspects, the SBS methods can be selected from those described in U.S. Pat. Nos. 6,210,891; 6,828,100, 6,833,246; 6,911,345; 6,969,488; 6,897,023; 6,833,246; and 6,787,308; U.S. Pat. Pub. Nos. 2003/0064398; 2003/0022207; 2016/0130647; and PCT Pat. Pub. WO 2016/133764; Margulies et al., 2005, Nature 437:376-380; Ronaghi et al., 1996, Anal. Biochem. 242:84-89; Constans, A, 2003, The Scientist 17(13):36; and Bentley et al., 2008, *Nature* 456(7218):53-59. DNA sequencers that perform sequencing by synthesis are commercially available, for example, from Illumina Inc. (San Diego, Calif.), including MiniSeq, MiSeq, NextSeq, HiSeq, HiSeq X, and NovaSeq sequencing systems. Other DNA sequencing systems that can be used with the compositions and methods of the present invention include the BGISEQ-50, BGISEQ-500, BGISEQ-1000, MGI-200, and MGISEQ-2000 (BGI, Shenzhen, People's Republic of China); and the GeneReader sequencing platform (QIAGEN, Manchester, United Kingdom).

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pat. App. Pub. Nos. 2009/0026082 A1; 2009/0127589 A1; 2010/0137143 A1; or 2010/0282617 A1.

Another sequencing procedures that use cyclic reactions can be used together with the compositions and methods of the present invention, such as, for example, pyrosequencing. Pyrosequencing detects the release of inorganic pyrophosphate (PPi) as particular nucleotides are incorporated into a nascent nucleic acid strand (Ronaghi et al., Anal Biochem 242:84-89, 1996; Ronaghi, Genome Res. 11:3-11, 2001; Ronaghi et al., Science 281:363, 1998); and U.S. Pat. Nos. 6,210,891; 6,258,568 and 6,274,320. In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, U.S. Pat. App. Pub. No. 2005/0191698 A1, U.S. Pat. Nos. 7,595,883, and 7,244,559.

In some aspects, sequencing by ligation methods can be selected from those described in PCT Pat. Pub. WO 1999/019341; WO 2005/082098; WO 2006/073504; and Shendure et al., 2005, Science, 309: 1728-1739. SBS methods can employ the ordered DNA nanoball arrays that are described, for example, in U.S. Pat. Pubs. 2010/0105052, 2007/099208, and US 2009/0264299) and PCT Pat. Pubs. WO 2007/120208, WO 2006/073504, and WO 2007/133831. The patent and non-patent publications listed in this paragraph above are hereby incorporated by reference in their entirety for all purposes.

According to one embodiment, sequencing is performed on ordered arrays of DNA nanoballs (DNBs). DNBs are produced by rolling circle replication of circular library constructs, each containing a fragment of a genome or other target nucleic acid of interest, resulting in a linear single-stranded DNA concatemer comprising multiple copies of the circular construct that collapses in aqueous solution to form a compact ball-like structure. The DNBs are disposed on the surface of a two-dimensional planar substrate to form a random array of single molecules. DNBs can be fixed directly or indirectly to the surface by a variety of techniques, including covalent attachment and non-covalent attachment. In some embodiments, patterned substrates with two dimensional arrays of spots are used to produce the DNB array. The spots are activated to capture and hold the DNBs, while the DNBs do not remain in the areas between spots. In general, a DNB on a spot will repel other DNBs, resulting in one DNB per spot. Since DNBs are three-dimensional (i.e., are not linear short pieces of DNA), arrays of the invention result in more DNA copies per square nanometer of binding surface than traditional DNA arrays. This three-dimensional quality further reduces the quantity of sequencing reagents required, resulting in brighter spots and more efficient imaging. Occupancy of DNB arrays often exceed 90%, but can range from 50% to 100% occupancy. Since DNBs are disposed on a surface and then stick to the activated spots in these embodiments, a high-density DNB array essentially "self-assembles" from DNBs in solution.

When such DNB arrays are used in sequencing-by-synthesis, the DNB array is contacted with a primer and the primer is extended by one complementary base by a polymerase in each cycle of sequencing. The identity of the RT incorporated by the polymerase at each position in the array is revealed as a result of binding of a specific affinity reagent to its corresponding RT. In four color sequencing, for example, the result is an array of DNBs, each of which is labeled with an affinity reagent, such that the identity of the RT incorporated at a particular position on the array is identifiable by the fluorescent label (or other detectable label) that is part of the affinity reagent bound to the RT.

In SBS methods using reversible terminators, a template nucleic acid is immobilized on a surface and an oligonucleotide primer is hybridized to a predetermined position on the template (i.e., the primer binding site). A nucleotide analog in which the deoxyribose 3'-OH is replaced with a removable blocking moiety, e.g., 3'-O-azidomethyl, is incorporated at the 3'-terminus of the primer in a primer extension reaction. The incorporated nucleotide analog is complementary to, and basepairs with, the nucleotide at the corresponding position on the template. Conventionally, the nucleotide analog includes a detectable label that identifies the nucleobase of the incorporated nucleotide analog, and therefore also identifies the base of the complementary nucleotide in the template. In commonly used SBS methods, the nucleotide analog includes a fluorescent label attached to the nucleobase by a cleavable linker.

In SBS methods using reversible terminators, after the incorporation of the nucleotide analog is detected, the blocking group is removed, typically chemically or enzymatically, to produce an incorporated nucleotide with a 3'-OH group. Additional rounds of incorporation of 3' blocked nucleotide analogs, detection, and de-blocking may be carried out in additional primer extension reactions. Although in each round of primer extension a nucleotide is added, the process may be referred to as extension of the primer, although it may be more precise to say that the extension product of the previous round (and not the original oligonucleotide primer) that is extended. The primer extension strand may be referred to various ways, including as the "growing DNA strand (GDS)," "primer extension product," or "extended primer."

It will be appreciated that when a dNTP (i.e., nucleoside triphosphate) is added to the 3' terminus of the primer, pyrophosphate is removed such that a nucleoside monophosphate (or nucleotide) is incorporated. An unlabeled or nonlabeled reversible terminator nucleotide can refer to either form (free nucleoside triphosphate or incorporated nucleotide monophosphate), unless otherwise specified, as will be clear from context. An unlabeled, or nonlabeled reversible terminator, nucleotide can be referred to as an NLRT.

In an aspect of the present invention the dNTP analog(s) that is incorporated are not detectably labeled. In this context "not detectably labeled" means that the incorporated dNTP is not conjugated to a dye that produces a detectable (e.g., fluorescent) signal or an enzyme that in the presence of substrates produces a detectable (e.g., chemiluminescent) signal. As used herein a "reversible terminator nucleotide" refers to a naturally occurring nucleotide, or a nucleotide analog, in which the deoxyribose 3'-OH is replaced with a removable blocking moiety, e.g., 3'-O-azidomethyl.

In an aspect of the present invention, in a sequencing reaction the incorporated NLRT is detected by an affinity reagent(s), such as an antibody(s), that distinguishes among 3' terminal nucleotides of the primer extension products and thereby identifies the nucleobase of the 3' terminal nucleotide of the template. In one approach, the affinity reagent specifically binds to an incorporated NLRT with containing a specific base (e.g., A, T, G, or C), or analog of the specific base, with much greater affinity than it binds incorporated NLRT with the other bases or other base analogs present in the sequencing reaction. In another approach, the affinity reagent binds to an incorporated NLRT with containing a specific base (e.g., A, T, G, or C), or analog of the specific base, with a characteristic affinity or efficiency that is different from the affinity or efficiency with which it binds to the other bases, or other base analogs present, present in the sequencing reaction.

According to the invention, the affinity reagents may also distinguish an NLRT incorporated at the 3' terminus of the primer extension product from previously incorporated, "internal," nucleotides not at the 3' terminus. Generally, the NLRT at the 3' terminus of the primer extension product differs from previously incorporated nucleotides by the presence of a free 3'-OH (which in internal nucleotides is replaced by a phosphodiester linkage) or the presence of a 3' blocking moiety, as well as differential accessibility of the sugar and nucleobase.

According to the present invention SBS reactions are carried out using four NLRTs with different nitrogenous bases (e.g., A, T, G and C). In an SBS reaction, different affinity reagents (e.g., 2, 3 or 4 different affinity reagents) are used, each of which binds an NLRTs with a specific nitrogenous base and does not bind NLRTs with different nitrogenous bases or, in some embodiments, binds NLRTs with different nitrogenous bases or non-identical blocking group but does so at different levels of efficiency.

The affinity reagent may distinguish one incorporated NLRT from a different NLRT based on structural differences in the nitrogenous base, the sugar, the cleavable blocking group or a combination of these elements. In some cases, different NLRTs are distinguished because of, for example, significant structural differences in the nitrogenous base (e.g., adenosine vs guanine) and/or significant structural differences in the blocking group (e.g., azidomethyl vs cyanoethenyl).

In addition, the affinity reagent may distinguish one incorporated NLRT from a different NLRT based on small structural differences (e.g., in some cases, addition or substitution fewer than 5 atoms) preferably in combination with natural differences. These small structural changes can be made in the nitrogenous base, the sugar, and/or blocking group. Affinity reagents such as antibodies can be made that distinguish such small differences between different NLRTs.

According to an aspect of the invention, each of the affinity reagents can be distinguished from the other(s) present in the sequencing reaction (for example, because each is differently labeled) or is bound by different secondary binders.

According to the invention there are constraints on the structures of each of the nitrogenous base, the sugar, and the cleavable blocking group.

For example, suitable modified bases will retain normal Watson-Crick binding specificity and should be compatible with incorporation by a DNA polymerase. In some embodiments, the base analog does not have fluorescent properties (Renatus et al., 2010, *Chem Rev.* 110(5): 2579-2619).

similarly, the sugar portion of the NLRTs may be modified. Nucleic acids with such modified NLRTs should retain the ability to anneal to the template strand and should be compatible with incorporation by a DNA polymerase.

Similarly, NLRT's with blocking groups that differ only slightly may be used. For example, 2, 3, or 4 different such NLRT's may be used.

In certain embodiments of the invention, a blocking group (not including the deoxyribose 3' oxygen atom) has a molecular weight (MW) less than 184, often less than 174, often less than 164, often less than 154, often less than 144, often less than 134, often less than 124, often less than 114, often less than 104, often less than 94, and sometimes less than 84.

In certain embodiments the molecular weights of deoxyribonucleotide monophosphates are in the range of about 300 to 325 (dAMP 331.2, dCMP 307.2, dGMP 347.2 and dTMP 322.2). In certain embodiments, the NLRT moiety when incorporated into a primer extension product (i.e., including the reversible terminator blocking group but not including the pyrophosphate of the dNTP) has a molecular weight less than 700, less than 600, less than 550, often less than 540, often less than 530, often less than 520, often less than 510, often less than 500, often less than 490, often less than 480, often less than 470, and sometimes less than 460.

In certain embodiments the methods of the invention are used to generate sequencing reads longer than 1000 nucleotide, sometimes 10-500 nucleotides, sometimes 10-250, sometimes more than 25, sometimes more than 50 nucleotides. In some cases sequencing is carried out with fewer than one error per 2000 bases, one error per 5000 bases.

Figure 5:
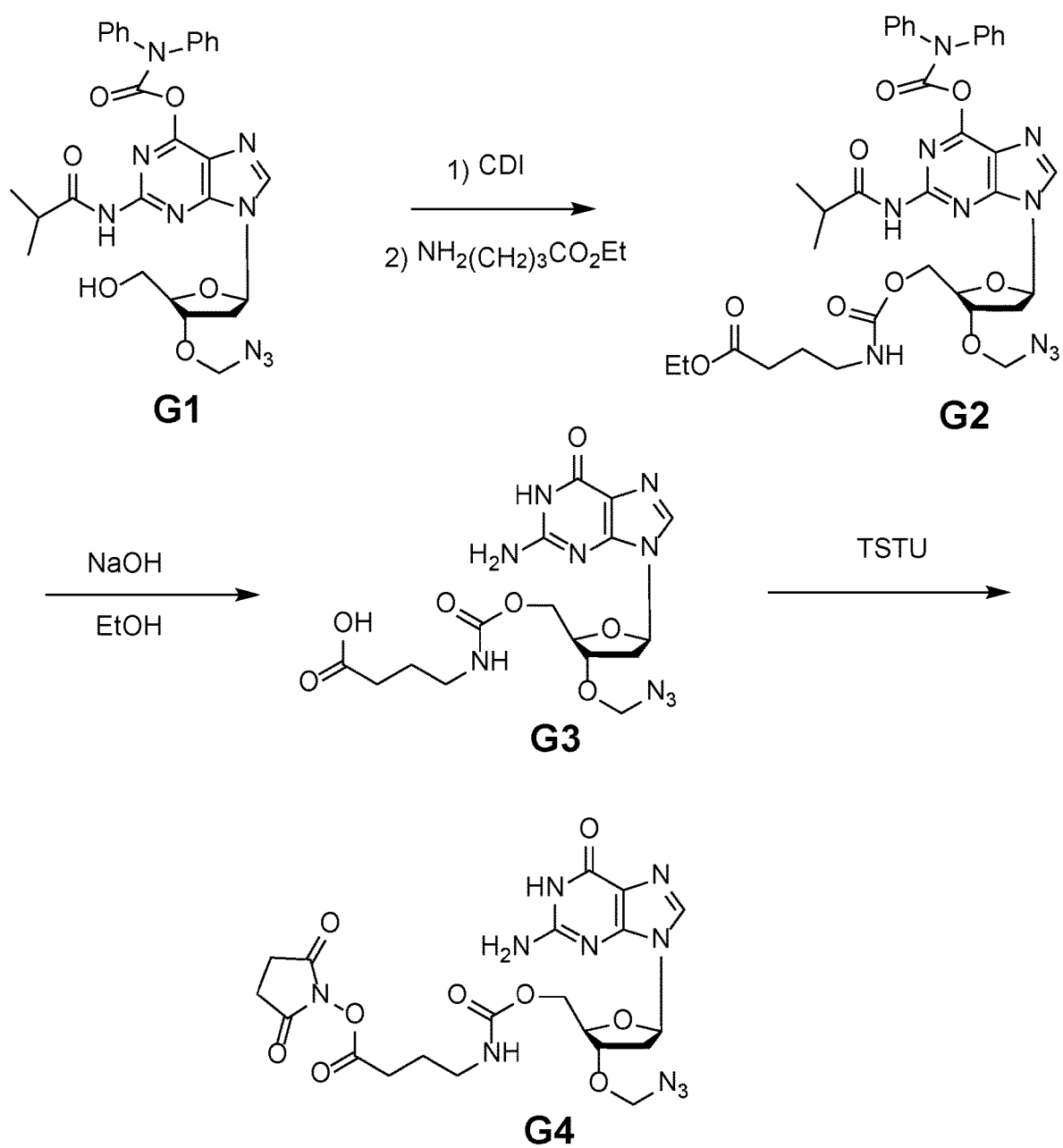
FIG. 5 illustrates the synthesis of the active ester of 3'-O-azidomethyl-2'-deoxyguanine (G4).

11. Examples 11.1 Example 1. Preparation of Conjugated 3'-O-azidomethyl-2'-dG, -dC, -dA and -dT Antigens Synthesis of active ester of 3'-O-azidomethyl-2'-deoxyguanine. Synthesis of the amino-reactive N-hydroxysuccinimide (NHS) ester of 3'-O-azidomethyl-2'-deoxyguanine is shown in FIG. 5. Compound G1 (416 mg, 0.708 mmol), anhydrous DMF (3 mL) and 1,1'-carbonyldiimidazole (CDI) (171 mg, 1.054 mmol) were added into a 50 mL flask. The reaction mixture was stirred at room temperature for 20 h. Ethyl 4-aminobutyrate hydrochloride (384 mg, 2.29 mmol) and triethylamine (300 µL, 2.155 mmol) were added. The mixture was stirred at 40° C. for 10 h. Most DMF was removed on a rotary evaporator (or rotovap) under vacuum to give crude compound G2.

To the crude compound G2, EtOH (5 mL) and 1N NaOH/H$_2$O (7 mL) were added. The mixture was stirred at room temperature for three days. 1N HCl/H$_2$O was added to adjust the pH to 7.4. Most EtOH was removed on a rotovap and then filtered. The filtrate was purified by preparatory HPLC using 25 mM TEAB buffer (triethylamine bicarbonate, pH 8.0 at room temperature) and CH$_3$CN to give compound G3 (341 mg) as a white solid. LCMS: 452.1 (MS+).

In a 5 mL vial, compound G3 (42 mg, 0.076 mmol), anhydrous dimethyl-formamide (DMF) (0.6 mL) and O—(N-Succinimidyl)-N,N,N',N'-tetramethyluronium tetrafluoroborate (TSTU) (19 mg, 0.063 mmol) were added. The reaction mixture was stirred at room temperature for 1 hour, and the desired activated NHS ester G4 was obtained for making biological conjugates. LCMS: 548 (MS+).

Conjugation of 3'-O-azidomethyl-dG with bovine serum albumin (BSA). 20 mg BSA (10 mg/ml) in 50 mM Na bicarbonate buffer (pH=9.0) with 150 mM NaCl was reacted with 5 mg Compound G4. The reaction was run at room temperature for 1 hour, and the reaction mixture was purified with a desalting column (Bio-Gel© P Polyacrylamide Beads [P6DG beads], Bio-Rad Laboratories, Hercules, Calif.) in phosphate-buffered saline. The conjugate was lyophilized to give a white powder.

Conjugation of 3'-O-azidomethyl-dG with keyhole limpet hemocyanin (KLH). 20 mg KLH (10 mg/ml) in 50 mM sodium bicarbonate buffer (pH=9.0) with 150 mM NaCl was reacted with 7 mg Compound G4. The reaction was run at room temperature for one hour, and the reaction mixture was purified with a desalting column (P-6DG beads) in phosphate-buffered saline. The conjugate was lyophilized to give a white powder.

Figure 9:
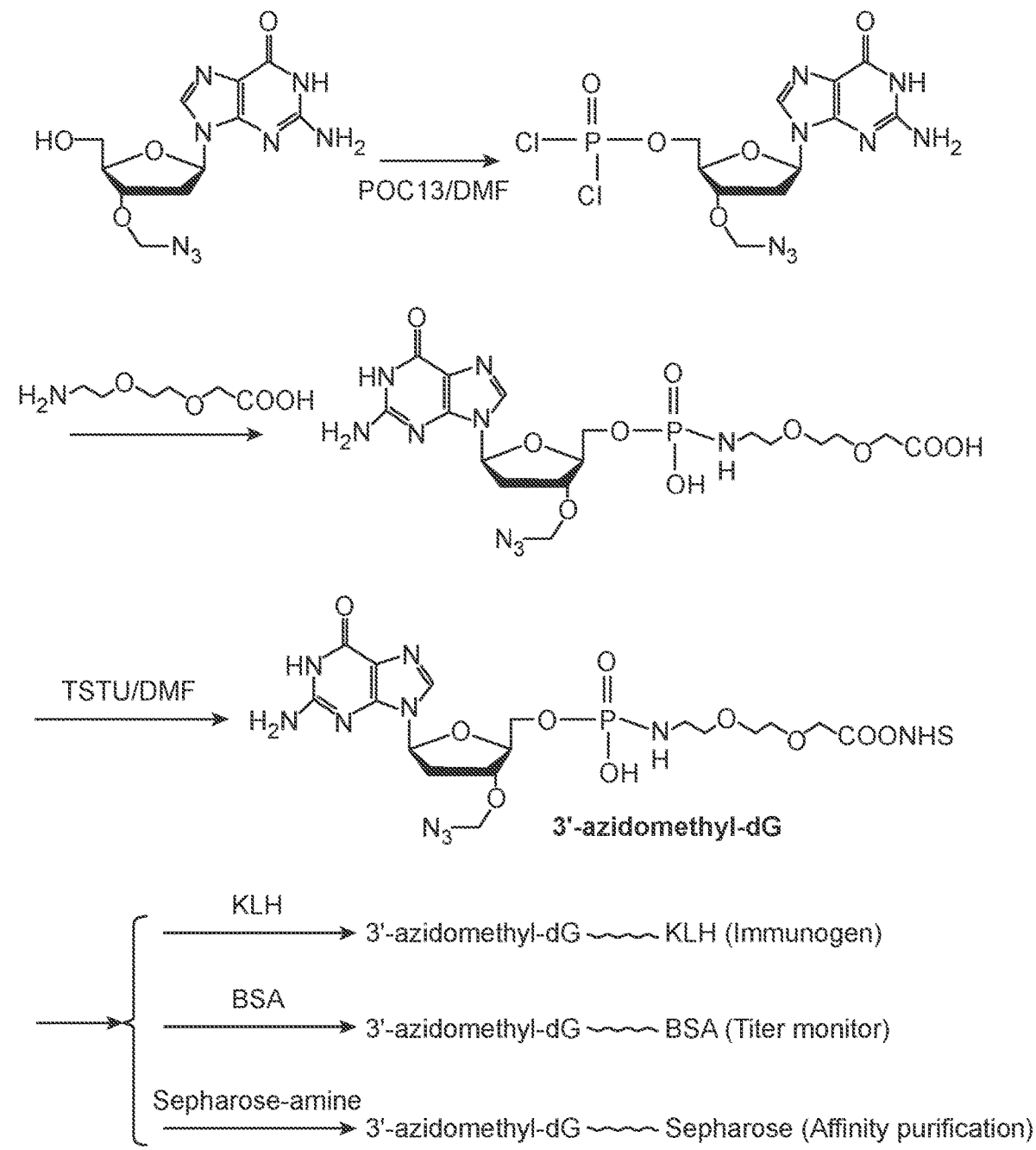
FIG. 9 illustrates (using 3'-O-azidomethyl-2'-deoxycytosine) conjugation of 3'-O-azidomethyl-dC-NHS ester to BSA, KHL and agarose resin for use as immunogen, titer monitor, and substrate for affinity purification.

Conjugation of the 3'-O-azidomethyl-dC-NHS ester to BSA, KLH and agarose resin is shown in FIG. 9, using a synthetic method slightly different from that shown in FIG. 5 in which a different linker is used.

Conjugation of 3'-O-azidomethyl-dG with amine-activated agarose resin. 20 ml wet amine-activated agarose resin (5 µmole activated group/ml) was washed with 30 mL 50 mM sodium bicarbonate buffer (pH=9.0), and 150 mM NaCl. 70 mg compound G4 was added to 20 ml wet beads, the reaction was incubated and rotated at room temperature (RT) for two hours. After reaction, the resin was washed with 50 mL phosphate-buffered saline until the absorbance of 260 nm was lower than 0.02 to give the desired purification resin.

Figure 6:
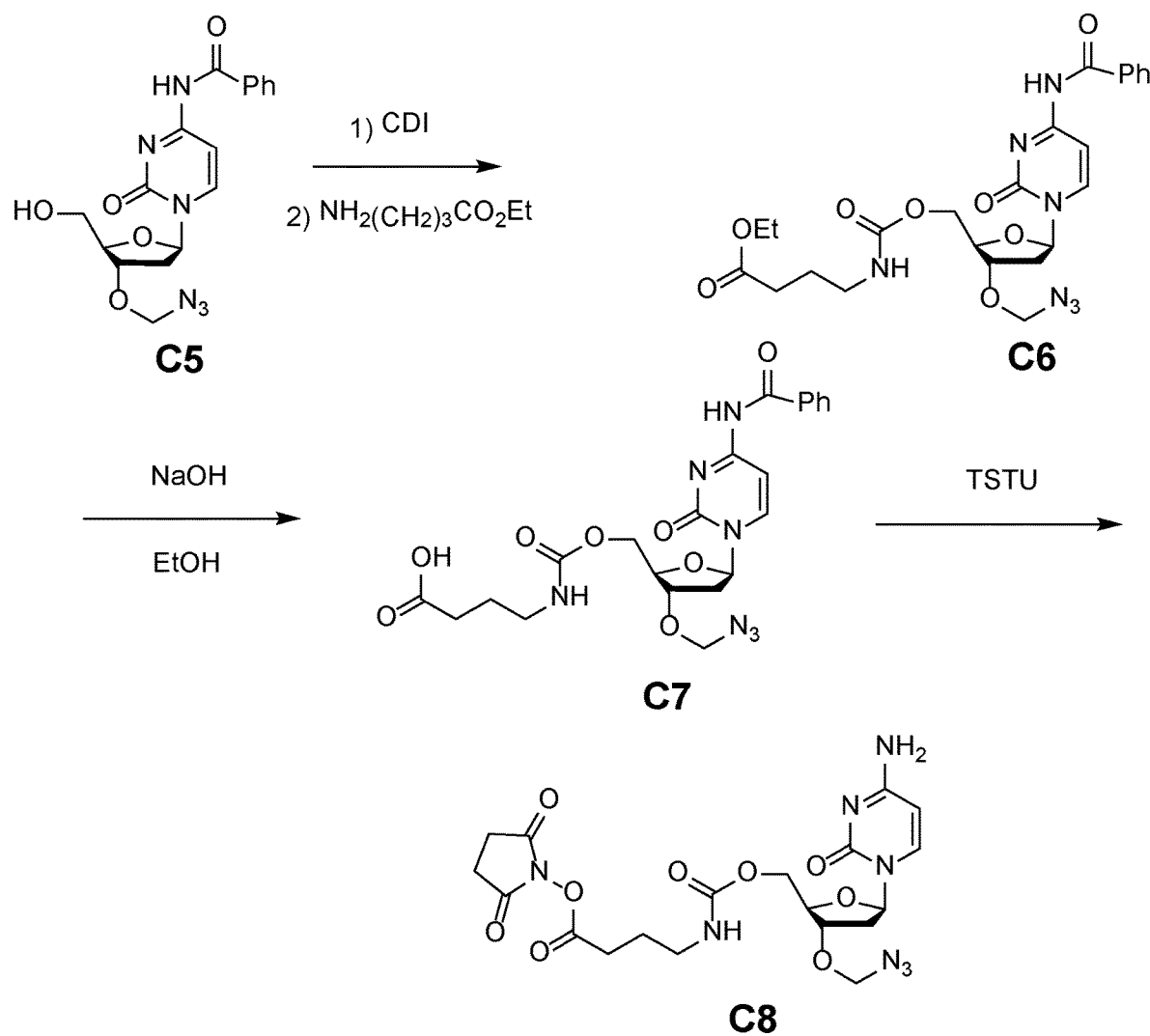
FIG. 6 illustrates the synthesis of the active ester of 3'-O-azidomethyl-2'- (C8)

Synthesis of amino-reactive NHS ester of 3'-O-azidomethyl-2'-deoxycytosine (C8). Synthesis of the amino-reactive NHS ester of 3'-O-azidomethyl-2'-deoxycytosine (C8) is shown in FIG. 6. Compound C5 (410 mg, 1.061 mmol), anhydrous DMF (3 mL) and 1,1'-carbonyldiimidazole (CDI) (213 mg, 1.314 mmol) were added to a 50 mL flask. The reaction mixture was stirred at room temperature for 20 hours. Ethyl 4-aminobutyrate hydrochloride (223 mg, 1.330 mmol) and triethylamine (200 µL, 1.437 mmol) were added. The mixture was stirred at 40° C. for 6 hours. Most DMF was removed on a rotovap under vacuum to give crude compound C6.

To the crude compound C6 was added EtOH (5 mL) and 1N NaOH/H$_2$O (5 mL). The mixture was stirred at room temperature for 24 hours. 1N HCl/H$_2$O was added to adjust the pH to 7.4, most of the EtOH was removed on a rotovap, and then the filtrate was filtered. The filtrate was purified by prep HPLC using 25 mM TEAB buffer and CH$_3$CN to give compound C7 (518 mg) as a white solid. LCMS: 412.1 (MS+).

In a 5 mL vial, compound C7 (49 mg, 0.096 mmol), anhydrous DMF (0.8 mL) and TSTU (27 mg, 0.090 mmol) were added. The reaction mixture was stirred at room temperature for 1 hour, and the desired activated NHS ester C8 was obtained for making biological conjugates. LCMS: 509.2 (MS+).

Conjugation of 3'-O-azidomethyl-dC with bovine serum albumin (BSA). 20 mg BSA (10 mg/ml) in 50 mM Na bicarbonate buffer (pH=9.0) with 150 mM NaCl was reacted with 5 mg Compound C8. The reaction was run at room temperature for 1 hour, and the reaction mixture was purified with a desalting column (P6DG beads) in phosphate-buffered saline. The conjugate was lyophilized to give a white powder.

Conjugation of 3'-O-azidomethyl-dC with keyhole limpet hemocyanin (KLH). 20 mg KLH (10 mg/ml) in 50 mM Na bicarbonate buffer (pH=9.0) with 150 mM NaCl was reacted with 7 mg Compound C8. The reaction was run at room temperature for 1 hour, and the reaction mixture was purified with desalting column (P-6DG beads, Bio-Rad Laboratories, Inc.) in phosphate-buffered saline. The conjugate was lyophilized to give a white powder.

Conjugation of 3'-O-azidomethyl-dC with amine-activated agarose resin. 20 ml wet amine-activated agarose resin (5 μmole activated group/ml) was washed with 30 mL 50 mM sodium bicarbonate buffer (pH=9.0) and 150 m M NaCl. 70 mg Compound C8 was added to 20 ml wet beads, the reaction was incubated and rotated at RT for 2 hours. After reaction, the resin was washed with 50 mL phosphate-buffered saline until the absorbance of 260 nm was lower than 0.02 to give the desired purification resin.

Figure 7:
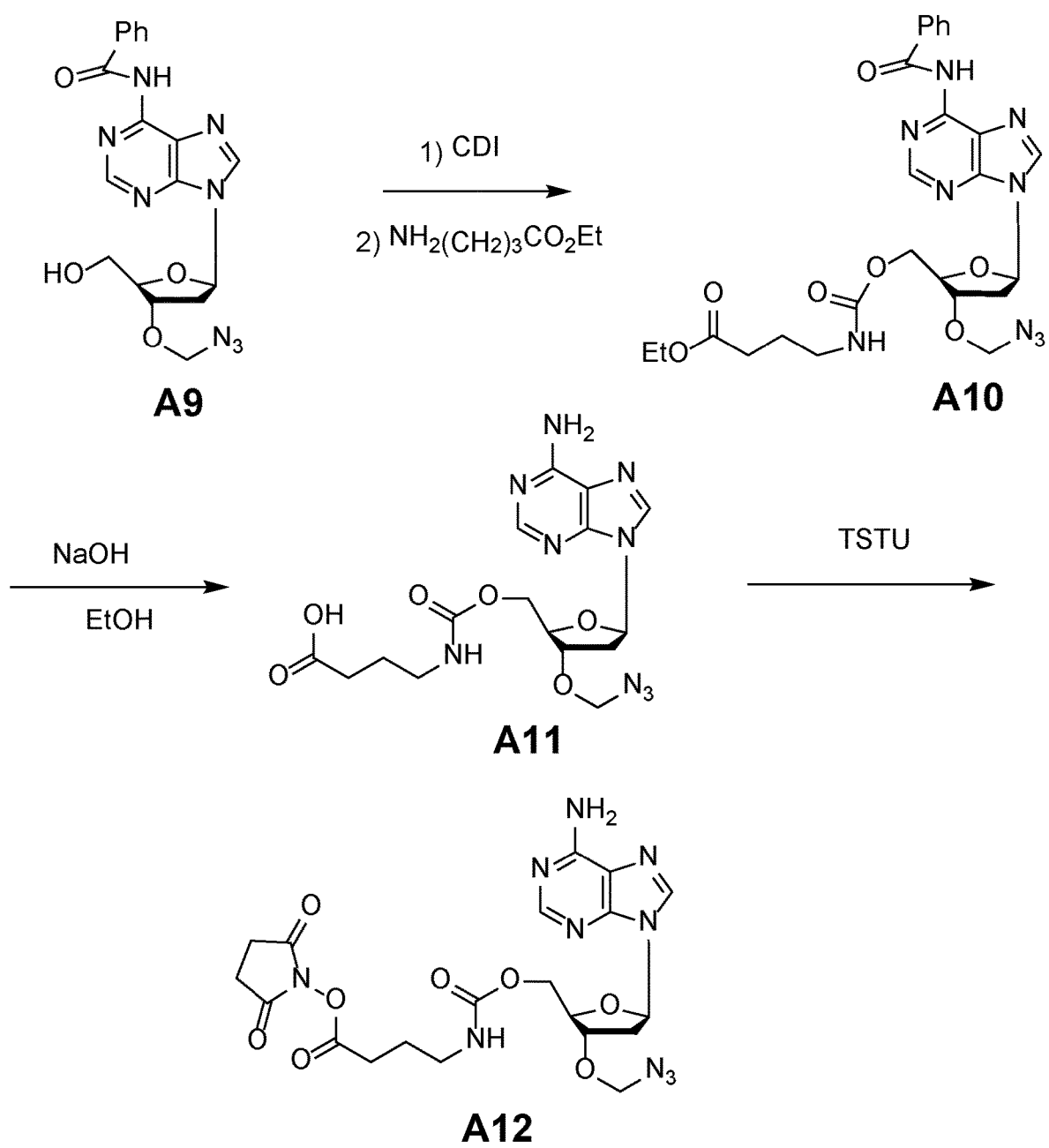
FIG. 7 illustrates the synthesis of the active ester of 3'-O-azidomethyl-2'-deoxyadenine (A12).

Synthesis of amino-reactive NHS ester of 3'-O-azidomethyl-2'-deoxyadenine (A12). Synthesis of the amino-reactive NHS ester of 3'-O-azidomethyl-2'-deoxyadenine (A12) is shown in FIG. 7. Compound A9 (111 mg, 0.270 mmol), anhydrous DMF (1 mL) and 1,1'-carbonyldiimidazole (CDI) (70 mg, 0.431 mmol) were added to a 25 mL flask. The reaction mixture was stirred at room temperature for 24 hours. Ethyl 4-aminobutyrate hydrochloride (78 mg, 0.465 mmol) and triethylamine (75 uL, 0.539 mmol) were added. The mixture was stirred at 40° C. for 16 h. Most DMF was removed on a rotovap under vacuum to give crude compound 10.

To the crude compound A10, EtOH (2 mL) and 1N NaOH/H$_2$O (4 mL) were added. The mixture was stirred at 40° C. for 24 hours. 1N HCl/H$_2$O was added to adjust the pH to 8.5, most EtOH was removed on a rotovap, and then the mixture was filtered. The filtrate was purified by preparative HPLC using 25 mM TEAB buffer and CH$_3$CN to give compound A11 (107 mg) as a white solid. LCMS: 435.9 (MS+).

In a 5 mL vial, compound 11 (61 mg, 0.114 mmol), anhydrous DMF (1 mL) and TSTU (20 mg, 0.066 mmol) were added. The reaction mixture was stirred at room temperature for 1 hour, and the desired activated NHS ester A12 was obtained for making biological conjugates. LCMS: 555.2 (MS+).

Conjugation of 3'-O-azidomethyl-dA with bovine serum albumin (BSA). 20 mg BSA (10 mg/ml) in 50 mM Na bicarbonate buffer (pH=9.0) with 150 mM NaCl was reacted with 5 mg Compound A12. The reaction was run at room temperature for 1 hour, and the reaction mixture was purified with a desalting column (P-6DG beads) in phosphate-buffered saline. The conjugate was lyophilized to give a white powder.

Conjugation of 3'-O-azidomethyl-dA with keyhole limpet hemocyanin (KLH). 20 mg KLH (10 mg/ml) in 50 mM Na bicarbonate buffer (pH=9.0) with 150 mM NaCl was reacted with 7 mg Compound A12. The reaction was run at room temperature for 1 hour, and the reaction mixture was purified with desalting column (P-6DG beads) in phosphate-buffered saline. The conjugate was lyophilized to give a white powder.

Conjugation of 3'-O-azidomethyl-dC with amine-activated agarose resin. 20 ml wet amine-activated agarose resin (5 μmole activated group/ml) was washed with 30 mL 50 mM sodium bicarbonate buffer (pH=9.0), and 150 mM NaCl. 70 mg compound A12 was added to 20 ml wet beads, the reaction was incubated and rotated at room temperature for 2 hours. After reaction, the resin was washed with 50 mL phosphate-buffered saline until the absorbance of 260 nm was lower than 0.02 to give the desired purification resin.

Figure 8:
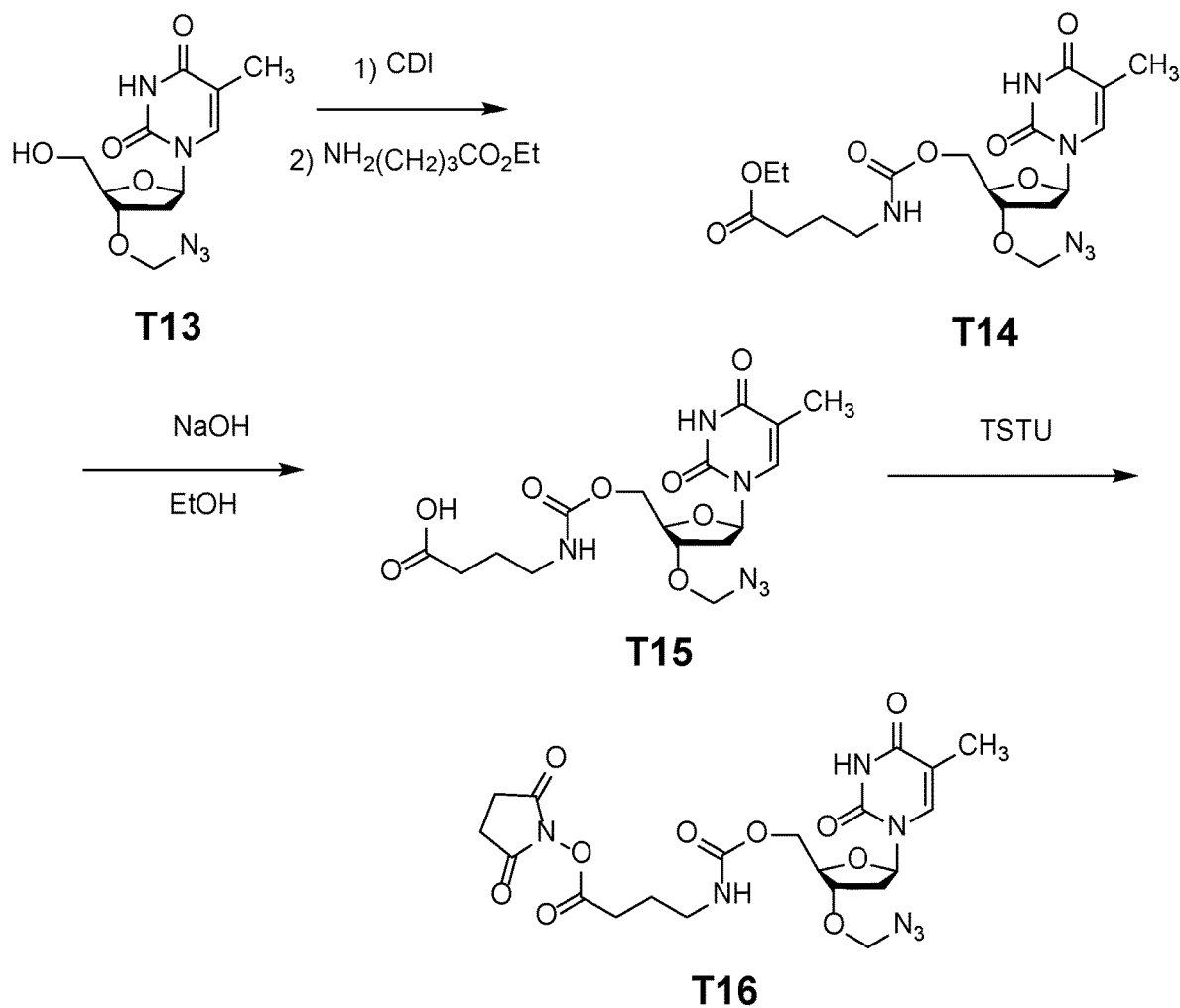
FIG. 8 illustrates the synthesis of the active ester of 3'-O-azidomethyl-2'-deoxythymine (T16).

Synthesis of amino-reactive NHS ester of 3'-O-azidomethyl-2'-deoxythymine (T16). Synthesis of the amino-reactive NHS ester of 3'-O-azidomethyl-2'-deoxythymine (T16) is shown in FIG. 8. Compound T13 (108 mg, 0.363 mmol), anhydrous DMF (1 mL) and 1,1'-carbonyldiimidazole (CDI) (74 mg, 0.456 mmol) were added into a 25 mL flask. The reaction mixture was stirred at room temperature for 24 hours. Ethyl 4-aminobutyrate hydrochloride (80 mg, 0.477 mmol) and triethylamine (75 uL, 0.539 mmol) were added. The mixture was stirred at 40° C. for 6 hours. Most DMF was removed on a rotovap under vacuum to give crude compound T14.

To the crude compound T14, EtOH (2 mL) and 1N NaOH/H$_2$O (2 mL) were added. The mixture was stirred at room temperature for 1 hour. 1N HCl/H$_2$O was added to adjust the pH to 7.5, then most EtOH was removed on rotovap, and the mixture was then filtered. The filtrate was purified by preparatory HPLC using 25 mM TEAB buffer and CH$_3$CN to give compound T15 (286 mg) as a white solid. LCMS: 426.5 (MS$^+$).

In a 5 mL vial, Compound 15 (121 mg, 0.225 mmol), anhydrous DMF (1 mL) and TSTU (40 mg, 0.132 mmol) were added. The reaction mixture was stirred at room temperature for 1 hour, and the desired activated NHS ester T16 was obtained for making biological conjugates. LCMS: 546.1 (MS+Na$^+$).

Conjugation of 3'-O-azidomethyl-dT with bovine serum albumin (BSA). 20 mg BSA (10 mg/ml) in 50 mM Na bicarbonate buffer (pH=9.0) with 150 mM NaCl was reacted with 5 mg Compound T16. The reaction was run at room temperature for 1 hour, and the reaction mixture was purified with desalting column (P-6DG beads) in phosphate-buffered saline. The conjugate was lyophilized to give a white powder.

Conjugation of 3'-O-azidomethyl-dT with keyhole limpet hemocyanin (KLH). 20 mg KLH (10 mg/ml) in 50 mM Na bicarbonate buffer (pH=9.0) with 150 mM NaCl was reacted with 7 mg Compound T16. The reaction was run at room temperature for 1 hour, and the reaction mixture was purified with a desalting column (P-6DG beads) in phosphate-buffered saline. The conjugate was lyophilized to give a white powder.

Conjugation of 3'-O-azidomethyl-dT with amine-activated agarose resin. 20 ml wet amine-activated agarose resin (5 μmole activated group/ml) was washed with 30 mL 50 mM sodium bicarbonate buffer (pH=9.0) and 150 mM NaCl. 70 mg Compound T16 was added to 20 ml wet beads, the reaction was incubated and rotated at room temperature for 2 hours. After reaction, the resin was washed with 50 mL phosphate-buffered saline until the absorbance of 260 nm was lower than 0.02 to give the desired purification resin.

11.2 Example 2. Making Polyclonal Antibodies Against Non-Labeled Reversible Terminators (NLRT)

This example describes protocols use for immunization and antibody purification use to produce reagents for sequencing. This protocol has been used to make polyclonal antisera with antibodies specific for NLRT-A, -T, -G, and —C with azidomethyl as the 3' blocking group.

Materials: The following materials were used for immunizing rabbits: 3 mg of KLH-antigen (to inject rabbit), 3 mg BSA-antigen (to titer), and 2-3 ml Sepharose-antigen (for purification).

Immunization of two rabbits: Rabbits were immunized with KLH-antigens described in Example 1.

In one approach a 70-day immunization schedule was followed: The first immunization was Day 1; the second immunization day was Day 20; the third immunization day was Day 40; the fourth immunization day was Day 60. 5 ml of pre-immune serum was collected before the first immunization, and a 5 ml test bleed was collected after the third immunization for quality control. Finally, a total of 100 ml antiserum was collected from two rabbits after 10 days of the fourth immunization.

Polyclonal Antibody Titer: The following protocol was used to monitor the titers:
a) Coat each well of plate with 3'-O-azidomethyl-2'-deoxy guanine-BSA at a concentration of 1 ug/per well (100 µl) overnight 4° C. or 2-3 hours at 37° C.
b) Add 100 ul serially diluted antisera from immunized rabbits body to each well and incubate for 30 min at 37° C.
c) Wash three times with excess 1×PBS.
d) Add 100 ul HRP-conjugated goat anti-rabbit IgG (1:4000) to each well and incubate for 30 min at 37° C.
e) Wash three times with excess 1×PBS.
f) Add 100 ul of ABTS substrate solution to each well and incubate at room temperature for 20 min.
g) Read the plate at $A_{405\ nm}$.

The same protocol was used to generate antisera to 3'-O-azidomethyl-2'-deoxy-cytosine, -adenine and -thymine.

Purification: The following protocol was used to purify the antibody from the serum. An Affi-Gel (Bio-Rad) was prepared by conjugation of 3'-azidomethyl-2'-deoxyribonucleobase to Sepharose 6B through an aminocaproic acid linker and a purification column was packed with the Affi-Gel. Antisera recovered from one or two rabbits (up to 100 ml) was applied to on an affinity column of Sepharose 6G immobilized with azido-dG, azido-dC, azido-dA, or azido-dT. A high titer of polyclonal antibodies specific for each of the 3'-azidomethyl NLRTs was obtained.

We have also used 50-day and 90-day immunization programs for raising polyclonal antibodies. For example, four rabbits were immunized with the antigen KLH-3'-azido-2'-deoxyguanosine conjugate. The schedule of immunizations was as follows: first immunization, day 1; second immunization, day 14; third immunization, day 28; and fourth immunization, day 42. 5 ml pre-immune serum was collected before the first immunization, and a 5 ml test bleed was collected after the third immunization for quality control. Finally, total 100 ml antiserum was collected from two rabbits after 10 days of the fourth immunization.

11.3 Example 3. Preparation of an E. coli DNA Library

DNA nanoball (DNB) arrays of an *E. coli* genomic DNA library were used in the sequencing experiments described in the Examples. DNBs and DNB arrays are described in, e.g., Drmanac et al., 2010, "Human genome sequencing using unchained base reads on self-assembling DNA nanoarrays," *Science* 327:78-81, incorporated herein by reference. During sample preparation, circular library constructs were made from fragments of *E. coli* genomic DNA, and the library constructs were amplified by rolling circle amplification (RCA) to produce DNBs comprising genomic DNA inserts with adjacent primer binding sites. The DNBs were arrayed in a DNA sequencing flow-cell (e.g., a BGISEQ-500 flow-cell or BGISEQ-1000 flow-cell) and sequencing was carried out using a BGISEQ-500 (BGI, Shenzhen, China; see Huang et al., 2017, "A reference human genome dataset of the BGISEQ-500 sequencer" Gigascience 6:1-9) or a BGISEQ-1000 (BGI, Shenzhen, China).

11.4 Example 4. Using dN-Azidomethyl-Specific Rabbit Polyclonal Antibodies and Labeled Goat Anti Rabbit Secondary Antibodies to Detect Incorporated NLRTs in a DNB Array Serum-derived antibodies raised against KLH conjugates of 3'-azidomethyl-dA, 3'-azidomethyl-dC, 3'-azidomethyl-dG, or 3'-azidomethyl-dT as described in Example 2 were used in this experiment. Four (4) different purification preparations of anti-NLRT antibodies were prepared for each of the four bases (i.e., RT-A, RT-C, RT-G and RT-T), resulting in sixteen (16) antibody preparations denoted A1-A4, C1-C4, G1-G4, and T1-T4. DNB arrays containing *E. coli* genomic DNA inserts, as described in Example 4, were primed and primers were extended using BG9 DNA polymerase (BGI Shenzhen, China), a polymerase engineered to incorporate 3' modified dNTPs and four non-labeled reversible terminators with a 3'-azidomethyl blocking group (e.g., 3'-azidomethyl-dATP, -dCTP, -dGTP and -dTTP). The sixteen (16) antibody preparations were individually applied to separate lanes on the DNB arrays at 10 µg/mL and incubated for at 35° C. for 5 min (16 separate incubations). At the end of the incubation unbound primary antibody the array was removed by washing with antibody buffer (AbB) (Tris buffered saline pH 7.4+0.1% BSA and 0.05% Tween-20) at 35° C. The array was then incubated with an AF488-labeled goat anti-rabbit secondary antibody (Fab fragment) obtained from Jackson Immune Research (West Grove, Pa., USA) for 5 min at 35° C. The array was washed with AbB to remove unbound secondary antibody and imaged using a BGISEQ-1000 sequencing system. It will be appreciated that each of the 16 antibody preparations stained with a single primary antibody would be expected to bind to incorporated NLRTs at approximately 25% of DNA sites.

Four control lanes in the sequencing arrays were generated by priming the DNBs and extending the primers using all four 3'-azidomethyl dNTPs labeled by a fluorophore attached to the base via a cleavable linker Control signal values shown here are for C-AF488.

TABLE 1 shows signal obtained using the control array and the antibody arrays. The highest level of antibody-mediated signal is shown in bold font. Although variation in signal intensity was observed between arrays (depending on the specific preparation of rabbit polyclonal antibody used) the results show that it is possible to meet or exceed the control signal intensity at relatively low antibody concentrations using this indirect detection technique.

TABLE 1

| NLRT-A | signal | NLRT-C | signal |
| --- | --- | --- | --- |
| Control | 30845.90 | Control | 30384.00 |
| A1 | 21268.92 | C1 | 13922.90 |
| A2 | 39444.35 | C2 | 10901.23 |
| A3 | 41803.23 | C3 | 27530.57 |
| A4 | 40488.85 | C4 | 18990.98 |
| NLRT-G | signal | NLRT-T | signal |
| Control | 24367.88 | Control | 28462.74 |
| G1 | 14171.97 | T1 | 9163.79 |
| G2 | 23279.56 | T2 | 17026.13 |
| G3 | 22748.62 | T3 | 25232.90 |
| G4 | 19498.47 | T4 | 41832.23 |

Figure 10A:
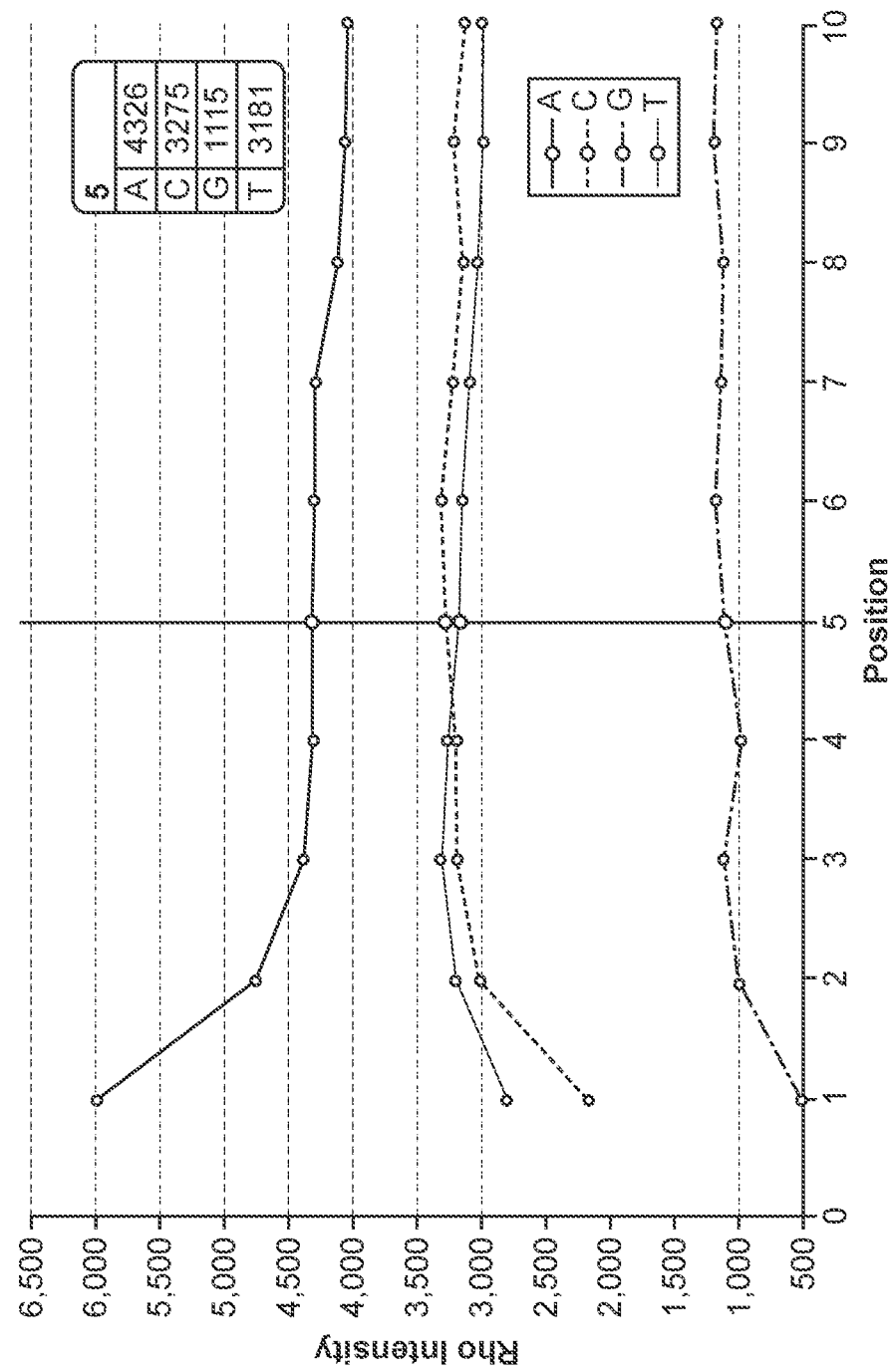
FIGS. 10A and 10B show Rho for 5 and 10 cycles of sequencing using three labeled RTs and one NLRT.
Figure 10B:
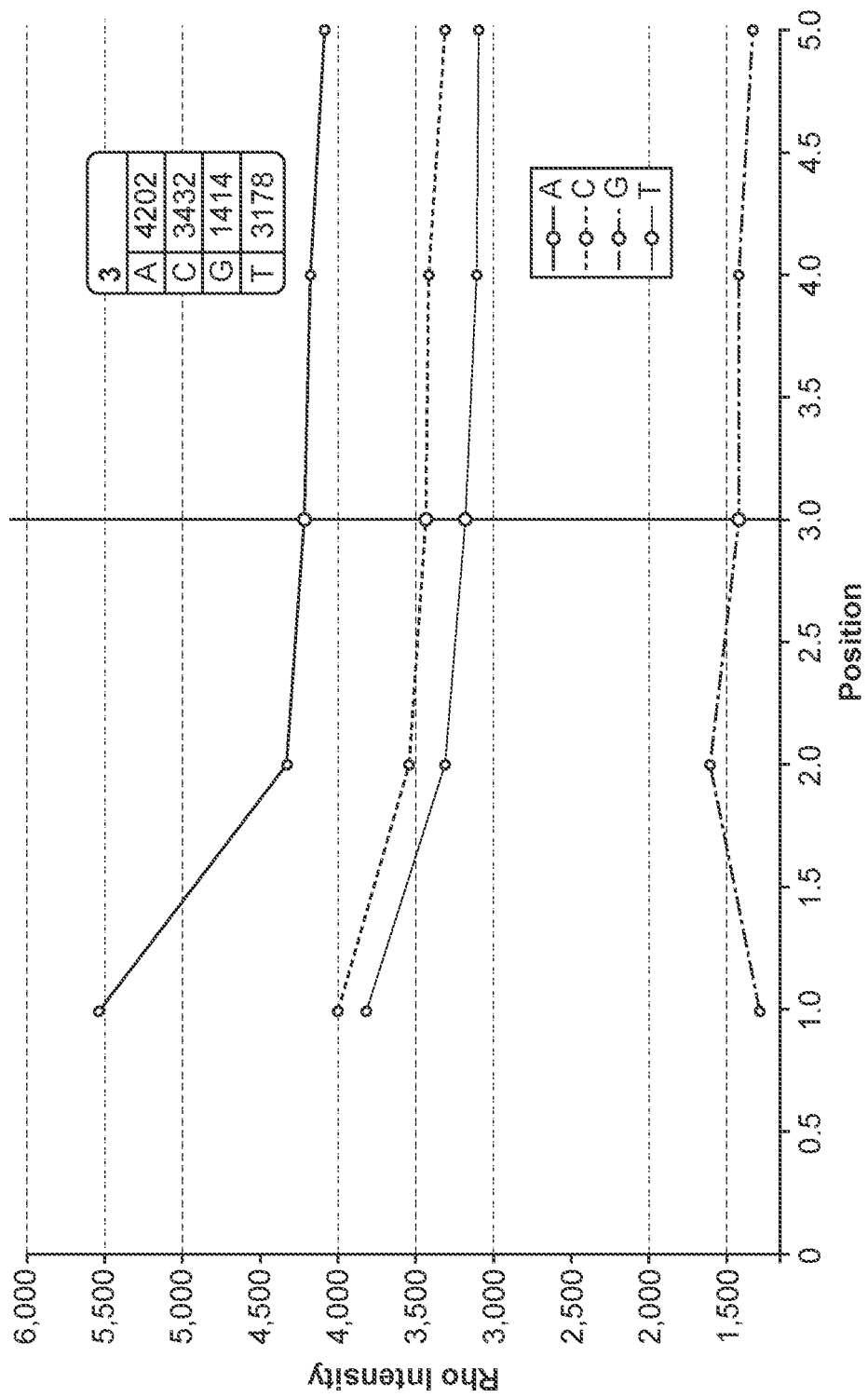
Figure 10C:
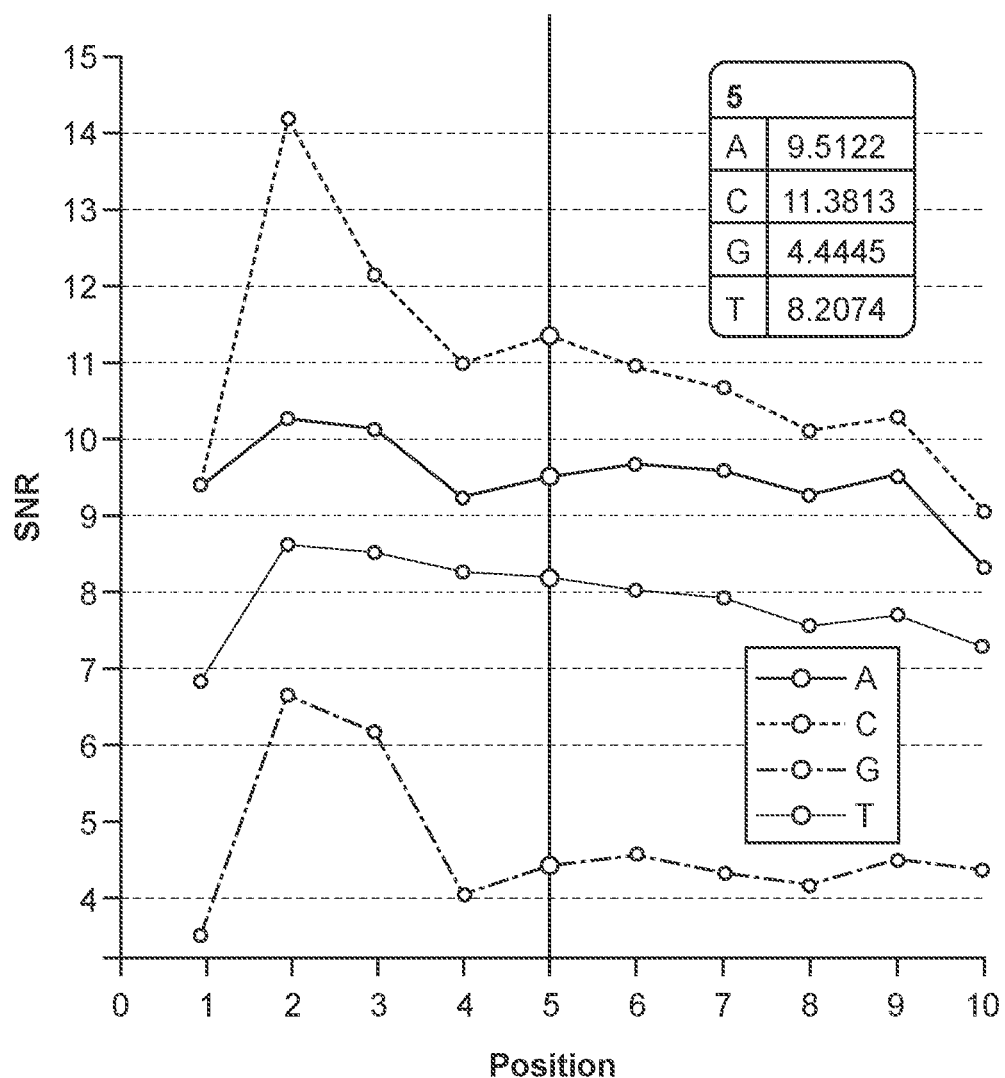
FIGS. 10C and 10D show Signal-Noise-Ratios (SNR) for 5 and 10 cycles of sequencing using three labeled RT and one NLRT.
Figure 10D:
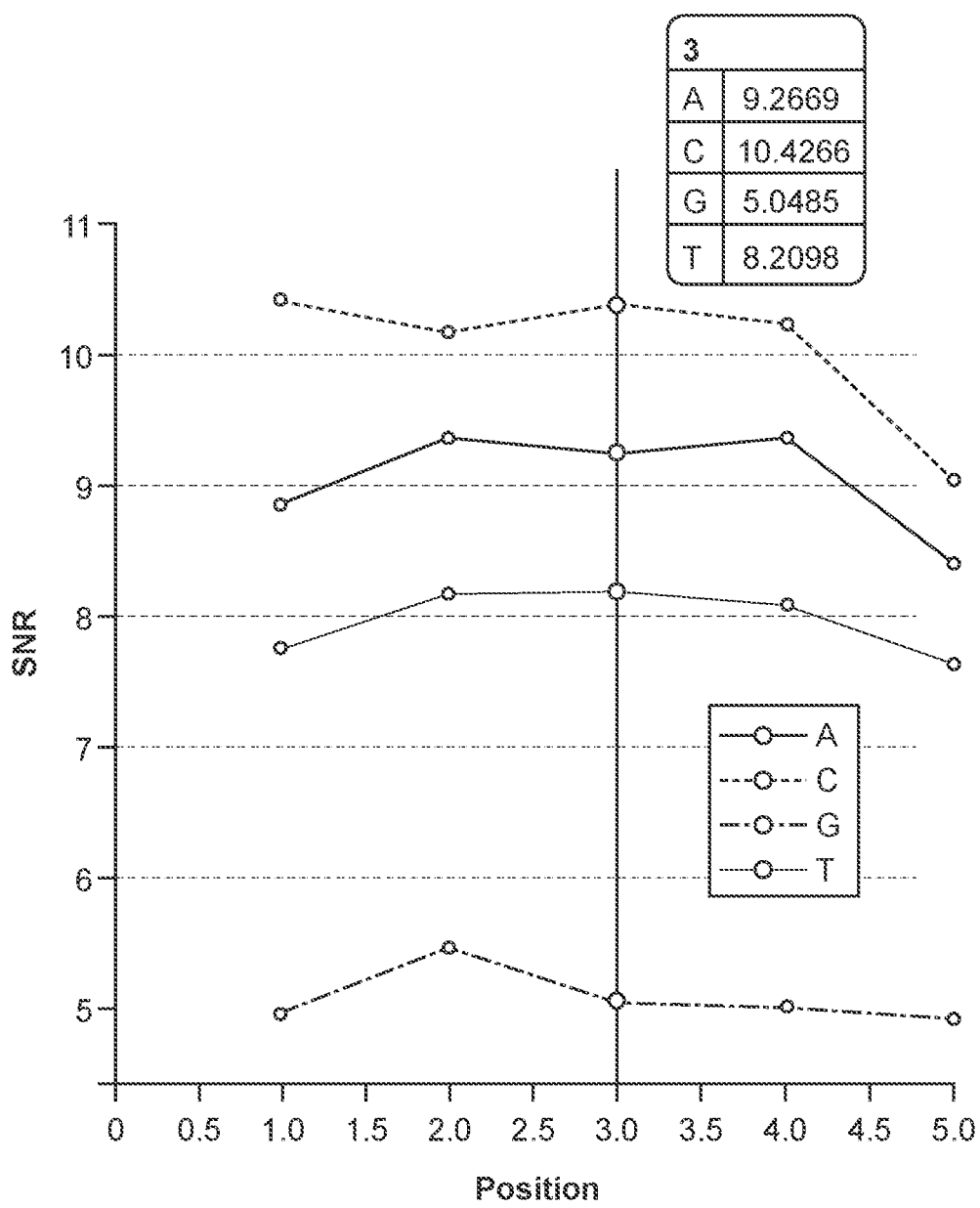

11.5 Example 5. DNA Sequencing Using Fluorescently Labeled RT-A, -C and -T and Unlabeled RT-G A DNA nanoball *E. coli* genomic DNA library was sequenced using fluorescently labeled RT-A, -C and -T and unlabeled RT-G, all with 3'-azidomethyl blocking groups. Sequencing was performed using a BGISEQ-500 sequencer (BGI, Shenzhen, China) and data were analyzed using a base calling analysis report provided with the sequencer. Sequencing was carried out for 5 cycles (FIGS. 10A and 10C) or 10 cycles (FIGS. 10B and 10D). FIGS. 10A and 10C show the Rho value. (Rho values are calculated by the subtraction of the background from the signal intensities obtained after image analysis. The normalization of the signal is also applied including the cross-talk correction.) FIGS. 10B and 10D show the signal-to-noise ratio (SNR).

The data, including the Rho of intensities and SNS (signal-to-noise ratio) from the successful base calling report, indicates that sequencing can be performed successfully with unlabeled RTs and labeled affinity reagents that bind specifically to the RT.

11.6 Example 6. DNA Sequencing Using Four Unlabeled RTs and Unlabeled Anti-NLRT Polyclonal Antibodies TABLE 2 illustrates sequencing data generated using a BGISEQ-1000 sequencer (BGI, Shenzhen, China) with 8-lane chip arrays (see Fehlmann et al., *Clin. Epigenetics* 8:123, 2016). Column 5 shows results using non-labeled reversible terminators in which the cleavable blocking moiety is a 3'-O-azidomethyl (NLRT-A, -T, -C and -G) and polyclonal antibodies ("1° antibodies") directed against each of the four NLRTs. Antibody binding was detected using a 2° antibody (AF488-labeled goat anti-rabbitFab fragment obtained from Jackson Immune Research. Signal was measured in the FIT channel. In the non-control lanes (e.g., TABLE 2, columns 3-8, each primary antibody is separately applied (i.e., applied in a separate channel) and detected. The raw signal values are shown.

The rows of TABLE 2 correspond to one NLRT with a 3' cleavable azidomethyl group as the reversible blocking group. Each row of TABLE 2 related to one target dNTP, and each column shows a test against that target. The columns are as follows:

Column 1: The specificity and concentration (in µg/mL) of the 1° antibody used in column 5 (Positive control 2).

Columns 2 and 9: Extension was carried out using four fluorescently labeled ("hot") reversible terminator dNTPs (with the fluorescent dye attached to the base via a cleavable linker. (Positive controls for the DNA arrays.)

Column 3: Extension was carried out using BG9 DNA polymerase. All four 1° antibodies at a concentration of 100 µg/ml (Positive control 1).

Column 4: Primary antibodies are omitted (Negative control; secondary antibody background only).

Column 5: Extension was carried out using four (4) unlabeled azidomethyl NLRTs. Results showing staining by each primary antibody used at the concentration in Column 1.

Column 6: Extension was carried out omitting the target NLRT but including 3 non-target NLRTs (Antibody specificity control 1);

Column 7: Negative control in which the target base at the 3' terminus of the GDS has 3'-OH rather then an azidomethyl blocking group (Antibody specificity control 2).

Column 8: Negative control in which no sequencing primer is used (specificity control 3).

TABLE 2

Sequencing Data on BGISeq-1000 with 8 Line Chip Arrays

| | 1 | 2 | 3 | 4 | 5 | 6 | 7 | 8 | 9 |
| --- | --- | --- | --- | --- | --- | --- | --- | --- | --- |
| | | | Median at $50^{th}$ percentile values in FIT channel | | | | | | |
| T | 600 | 29317 | 7073 | 3638 | 8999 | 5940 | 7356 | 8725 | 28805 |
| G | 50 | 27592 | 27781 | 3507 | 19959 | 3681 | 3774 | 4050 | 28611 |
| C | 300 | 28702 | 11008 | 3540 | 22063 | 4539 | 4538 | 4789 | 28949 |
| A | 75 | 27636 | 22569 | 3527 | 21693 | 4264 | 4227 | 4316 | 28242 |

11.7 Example 7. 50 Cycles of Sequencing in which Unlabeled RT-G is Detected Using an Anti-RT-G Rabbit Primary Antibody and a Labeled Goat Anti-Rabbit Secondary Antibody This Example shows results of fifty (50) cycles of sequencing-by-synthesis (SBS) carried out using an BGISEQ-1000 DNA sequencer and an *E. coli* genomic DNB library. A DNA primer complementary to the sequence flanking the genomic DNA insert was hybridized onto the DNB array and primer extension was carried out using 3'-azidomethyl reversible terminators (RT-A, —C, -G, -T) at a concentration of 2 µM each. Three of the reversible terminators (azidomethyl-A, —C, -T) were fluorescently labeled via cleavable linker attached to the base (used at a ratio of 50% labeled/50% non-labeled) and one reversible terminator (3'-azidomethyl-dGTP) was unlabeled. Primer extension was carried out at 35° C. for 2 min using BG9 DNA.

After one cycle of primer extension the array was washed to remove unincorporated nucleotides. Incorporated 3'-azidomethyl-dG was detected by incubating with anti-3'-azidomethyl-dG rabbit primary antibody pre-combined with an AF647-labeled goat anti-rabbit fluorescently labeled Fab fragment. The primary antibody and secondary antibodies (Fab fragment) were precombined by incubating them together for 15 min at 35° C. This precombined complex was incubated on the array at 25 µg/mL primary and 50

μg/mL secondary concentration for 10 min at 35° C. and the array was washed three times to remove any unbound antibodies.

After antibody incubation, the three labeled RTs (RT-A, —C, -T) were detected using their unique fluorescent label, and the non-labeled base (RT-G) was detected using the fluorescent label conjugated to the goat anti-rabbit fragment secondary antibody. After DNB base identity was determined via fluorescence wavelength detection, the linker to label (RT-A, -C, -T) and the 3' blocking group (RT-G, -A, —C, -T) were removed by reduction with THPP at 13 mM for 2 min at 35° C., allowing for the regeneration of the 3'-OH group and the ability to further extend the nascent DNA strand. This series of steps (extension, antibody incubation, detection, and unblocking) was repeated for a total of 50 cycles of sequence identification.

Figure 11A:
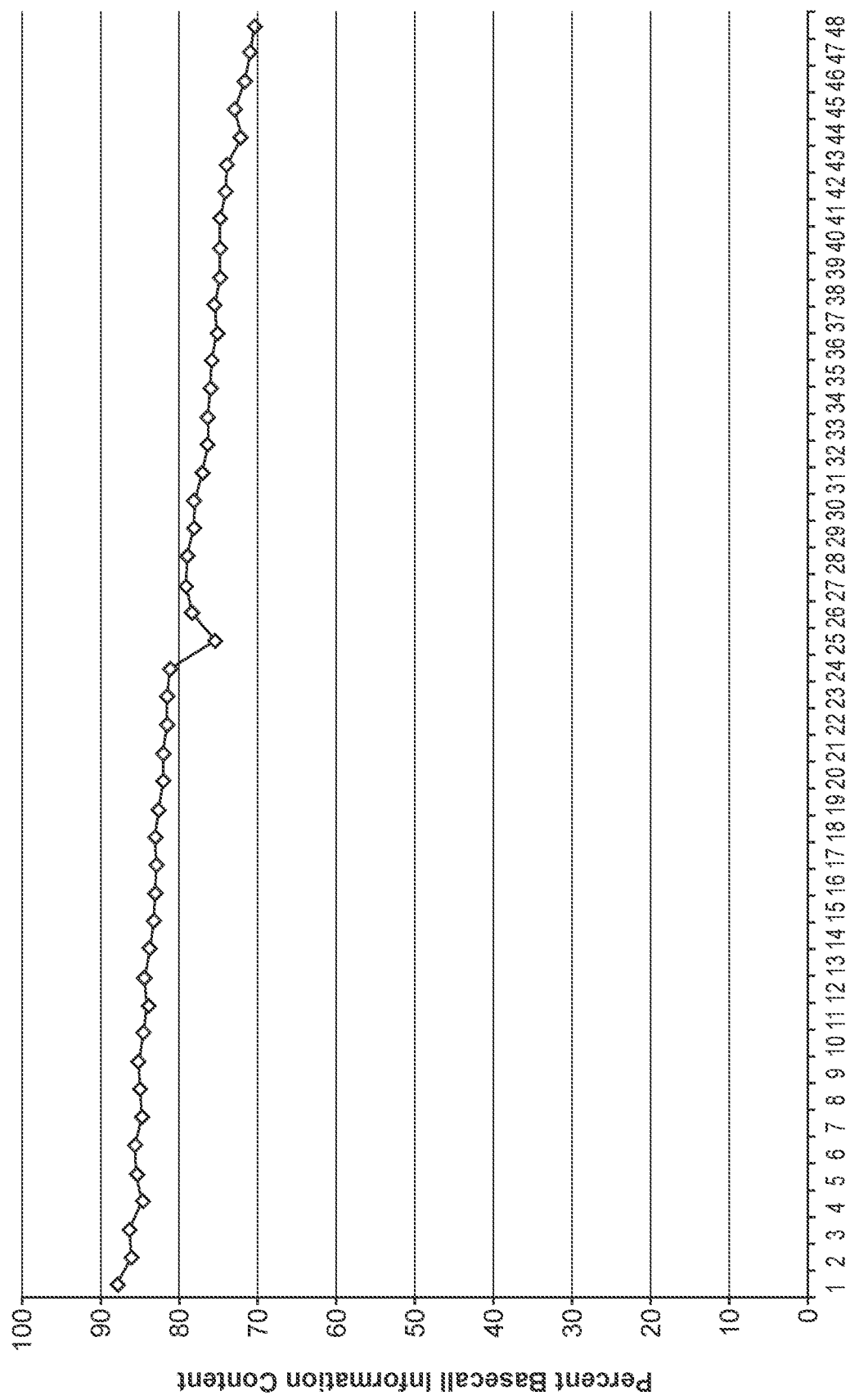
FIGS. 11A and 11B illustrate sequencing data metrics obtained using the BGISEQ-1000 DNA sequencer with non-labeled 3'-azidomethyl-dGTP detected by anti-3'-azidomethyl-dG rabbit primary antibody and anti-rabbit AF647 fragment secondary antibody for 50 cycles of sequencing-by-synthesis.

FIG. 11A shows the percent Basecall Information Content (BIC). This graph shows that the identity of the unlabeled base when detected indirectly through anti-3'-azidomethyl-dG rabbit primary antibody pre-combined with anti-rabbit AF647 fluorescently labeled fragment secondary antibody provides sufficient information for basecall analysis and identification of the unknown DNA residue(s).

Figure 11B:
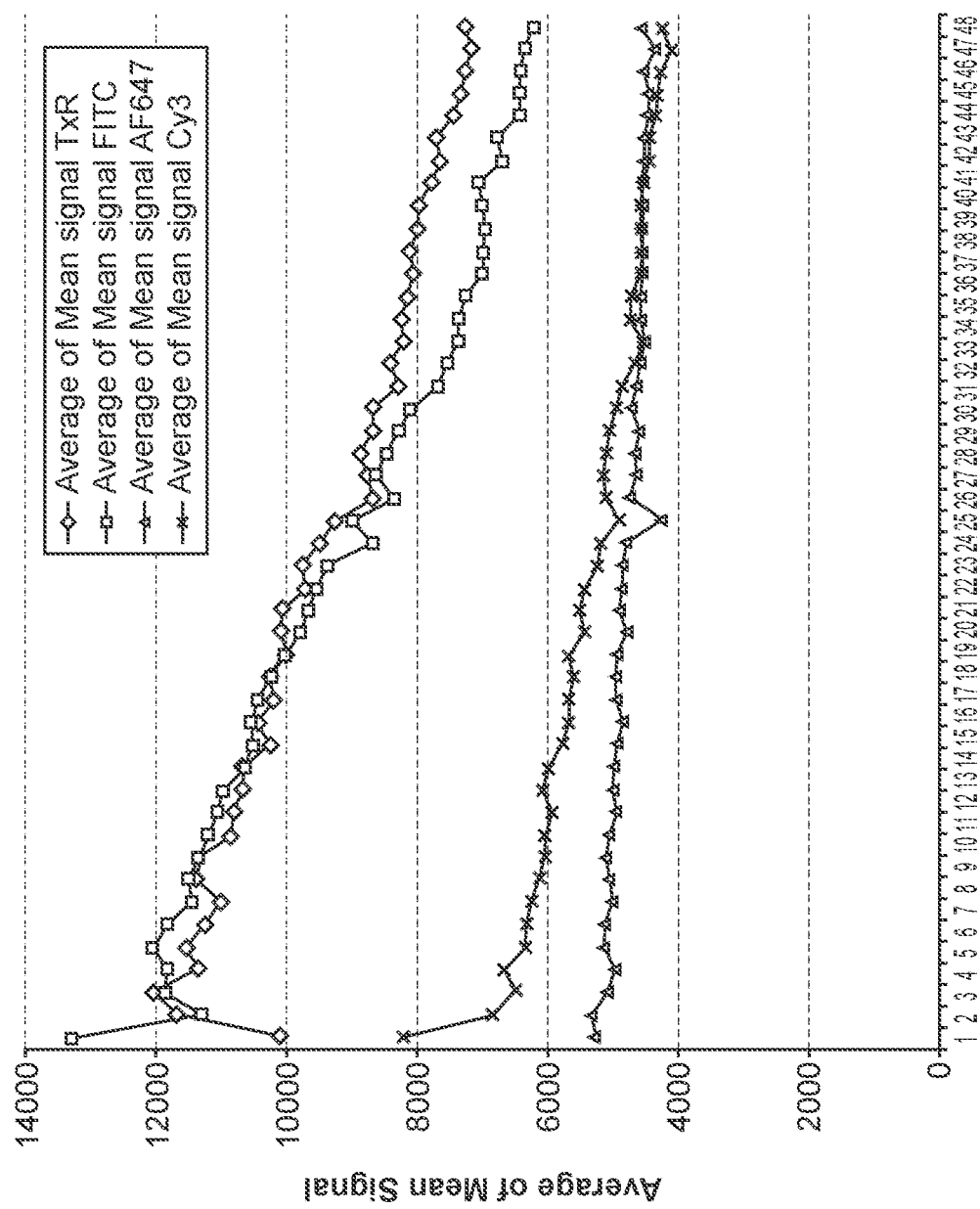

FIG. 11B shows the signal intensities and trends for each of the unique fluorescent labels. Three nucleotides (dATP, dCTP, dTTP) that contained a fluorescently labeled cleavable linker attached to the base were used at a ratio of 50% labeled/50% non-labeled and correspond to Cy3, FITC, and TxR respectively. Non-labeled 3'-azidomethyl-dGTP was detected by anti-3'-azidomethyl-dG rabbit primary antibody pre-combined with anti-rabbit AF647 fluorescently labeled fragment secondary antibody. These data show that the rate of degradation of signal intensity for the non-labeled 3'-azidomethyl-dG base is less than that of the cleavable linker labeled nucleotides. This reduced degradation of signal intensity indicates that longer reads may be possible using this technique than conventional methods using a dNTPs labeled using a cleavable linker.

11.8 Example 8. Antibodies Bind NLRT with Sufficient Specificity to Generate Signal-to-Noise-Ratio (SNR) Values Suitable for Basecalling Analysis The data in TABLES 3, 4, 5 and 6 show top signal, Rho (background and cross-talk subtracted signal), background signal ("back") and signal-to-noise ratio (SNR) values obtained with staining of non-labeled reversible terminators on *E. coli* genomic DNA using directly labeled anti-azidomethyl-base antibodies and for control arrays using labeled azidomethyl-bases. The experiment was performed on a BGISEQ-500 flow-cell array with an *E. coli* genomic DNA library and scanned on a BGISEQ-500 DNA sequencer.

Control values are results of sequencing using four labeled 3'-azidomethyl RTs (labels connected to the base via cleavable linker). 3'-Azidomethyl RTs were used at a ratio of 60% labeled ("hot"), 40% unlabeled ("cold") in TABLES 4, 5 and 6 and 25% labeled and 75% unlabeled in TABLE 3.

Pre-stain values are scanned after one round of primer extension but prior to addition of antibody.

Stained values were obtained by scanning after incubation (2×2 min at 35° C.) with the appropriate anti-azidomethyl-base antibodies at indicated concentrations. The anti-azidomethyl-base antibodies were directly labeled with the fluorophore shown. Values corresponding to the anti-azidomethyl-base binding are in bold.

TABLE 3 shows results using polyclonal antibodies against 3'-O-azidomethyl-2'-deoxyadenine. TABLE 4 shows results using polyclonal antibodies against 3'-O-azidomethyl-2'-deoxycytosine. TABLE 5 shows results using polyclonal antibodies against 3'-O-azidomethyl-2'-deoxyguanine. TABLE 6 shows results using polyclonal antibodies against 3'-O-azidomethyl-2'-deoxythymidine.

TABLE 3

| | N3A | | | |
|---|---|---|---|---|
| | A | C | G | T |
| | Control values (25% hot) | | | |
| Top | 3735 | 1801 | 1358 | 3139 |
| Rho | 2771 | 1542 | 1149 | 2894 |
| back | 330 | 424 | 275 | 440 |
| SNR | 8 | 7.3 | 7.9 | 9.5 |
| | 100% cold azido A incorporation prestain values: | | | |
| Top | 312 | 1833 | 1339 | 2948 |
| Rho | 263 | 1671 | 1160 | 1116 |
| back | 174 | 513 | 370 | 372 |
| SNR | 1.8 | 7.1 | 5.1 | 1.7 |
| | stained with anti-N3A-AF532 (F/P 4.8) at 75 ug/mL | | | |
| Top | 2185 | 1687 | 1295 | 3252 |
| Rho | 1896 | 1512 | 1147 | 3112 |
| back | 498 | 476 | 339 | 581 |
| SNR | 6.7 | 7 | 5.9 | 9.3 |

TABLE 4

| | N3C | | | |
|---|---|---|---|---|
| | A | C | G | T |
| | Control values (60% hot) | | | |
| Top | 13341 | 4541 | 5077 | 7646 |
| Rho | 10449 | 3618 | 4006 | 6344 |
| back | 153 | 460 | 422 | 468 |
| SNR | 13.5 | 11.1 | 11 | 11.4 |
| | 100% cold azido C incorporation prestain values: | | | |
| Top | 12596 | 3104 | 4419 | 7960 |
| Rho | 8688 | 930 | 1050 | 5055 |
| back | 122 | 384 | 322 | 512 |
| SNR | 9.5 | 3 | 2.8 | 7.4 |
| | stained with anti-N3C-IF700 (F/P 4.6) at 400 ug/mL | | | |
| Top | 13844 | 4454 | 4161 | 7924 |
| Rho | 10635 | 4028 | 3232 | 6504 |
| back | 7 | 1082 | 460 | 438 |
| SNR | 13.9 | 9.5 | 11.6 | 12.4 |

TABLE 5

| | N3G | | | |
|---|---|---|---|---|
| | A | C | G | T |
| | Control values (60% hot) | | | |
| Top | 13441 | 4541 | 5077 | 7646 |
| Rho | 10449 | 3618 | 4006 | 6344 |
| back | 153 | 460 | 422 | 468 |
| SNR | 13.5 | 11.1 | 11 | 11.4 |
| Top | 12251 | 2693 | 681 | 6911 |
| Rho | 7893 | 1709 | 551 | 4903 |
| back | 492 | 286 | 131 | 742 |
| SNR | 6.2 | 9.5 | 2.2 | 8 |

TABLE 5-continued

| | N3G | | | |
|---|---|---|---|---|
| | A | C | G | T |
| | stained with anti-N3G-AF647 (F/P 3.5) at 25 ug/mL | | | |
| Top | 13831 | 2921 | 2759 | 7278 |
| Rho | 11133 | 2208 | 2028 | 6437 |
| back | 441 | 444 | 297 | 689 |
| SNR | 12.2 | 7.5 | 8.9 | 12.3 |

TABLE 6

| | N3T | | | |
|---|---|---|---|---|
| | A | C | G | T |
| | Control values (60% hot) | | | |
| Top | 13341 | 4541 | 5077 | 7646 |
| Rho | 10449 | 3618 | 4006 | 6344 |
| back | 153 | 460 | 422 | 468 |
| SNR | 13.5 | 11.1 | 11 | 11.4 |
| | 100% cold azido T incorporation prestain values: | | | |
| Top | 7121 | 3258 | 2727 | 3926 |
| Rho | 1765 | 2884 | 2235 | 686 |
| back | 190 | 665 | 638 | 241 |
| SNR | 2.95 | 8.6 | 5.1 | 1.8 |
| | stained with anti-N3T-ROXtra (F/P 2.2) 600 ug/mL | | | |
| Top | 6698 | 2658 | 2506 | 4237 |
| Rho | 4782 | 2329 | 2279 | 2419 |
| back | 256 | 613 | 571 | 498 |
| SNR | 9.6 | 6.6 | 6.3 | 5.3 |

11.9 Example 9. Sequencing for 25 Cycles Using Labeled Anti NLRT Polyclonal Antibodies An *E. coli* genomic DNA library was made as described in Example 2, and arrayed on a BGISEQ-500 flow-cell. Primers were added and sequencing by synthesis was performed by primer extension using unlabeled nucleotide 3'-azidomethyl reversible terminators (dATP, dCTP, dGTP, dTTP). The unlabeled 3'-blocked dNTPs were present at a concentration of 1 µM each and were incorporated using BG9 DNA at 55° C. for 1 min per cycle. After incorporation and washing to remove unincorporated nucleotides, the four 3'-azidomethyl-base nucleotides were detected by contacting the array with a mixture of four directly labeled anti-3'-azidomethyl-base antibodies in the concentrations shown in TABLE 11 (range of 10-100 µg/mL) were incubated on the array at 35° C. 2×2 min per cycle. "2×2" refers to incubation with antibody for two minutes, followed by further 2 minute incubation after adding additional antibody. The array was washed three times to remove any unbound antibodies. TABLE 7 shows the identity of fluorophore directly conjugated to each detection antibody.

TABLE 7

| Rabbit Polyclonal Antibody Specificity | Fluorescent Dye | |
|---|---|---|
| 3'-O-azidomethyl-2'-deoxyguanine | Cy5 | |
| 3'-O-azidomethyl-2'-deoxyadenine | AF532 | Invitrogen |
| 3'-O-azidomethyl-2'-deoxycytosine | IF700 | AAT Bioquest |
| 3'-O-azidomethyl-2'-deoxythymine | 6-ROXtra ™ | AAT Bioquest |

The fluorescence signal at each position on the DNB array was determined by scanning for 80 ms during laser excitation of the fluorophore. After DNB base identity was determined, the 3' blocking group was removed by reduction with THPP (13 mM) for 2 min at 35° C., allowing for the regeneration of 3'-OH group and permitting further extension of the nascent DNA strand. Removal of the 3' blocking group also resulted in disassociation of the antibody from the primer extension product.

This series of steps (extension, antibody incubation, detection, and unblocking) was repeated for a total of 25 cycles of DNA sequence identity.

Figure 12A:
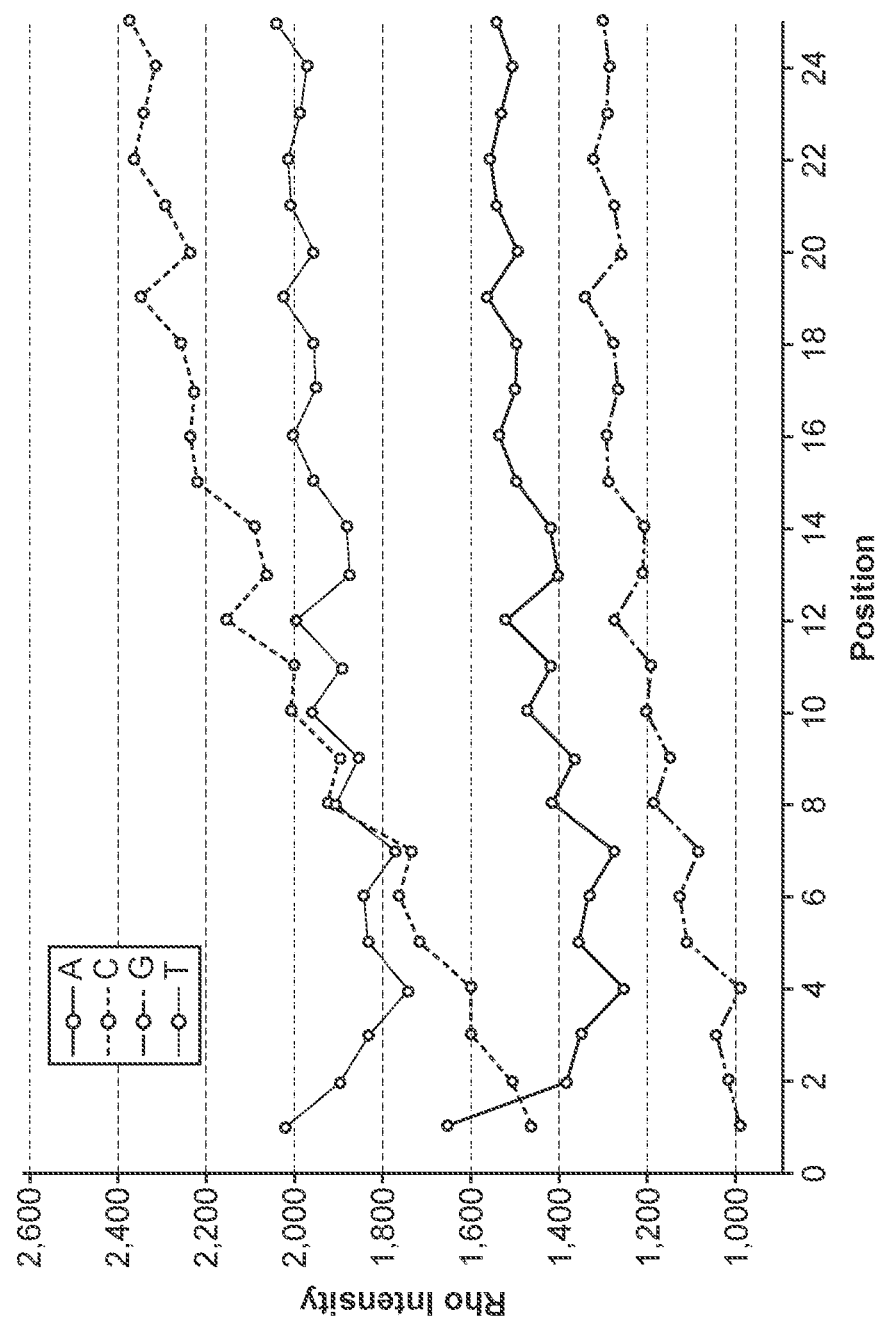
FIGS. 12A and 12B illustrate results from 25 sequencing cycles of *E. coli* genomic DNA on a BGISEQ-500 instrument using fluorescent directly labeled anti-azidomethyl-base antibodies.
Figure 12B:
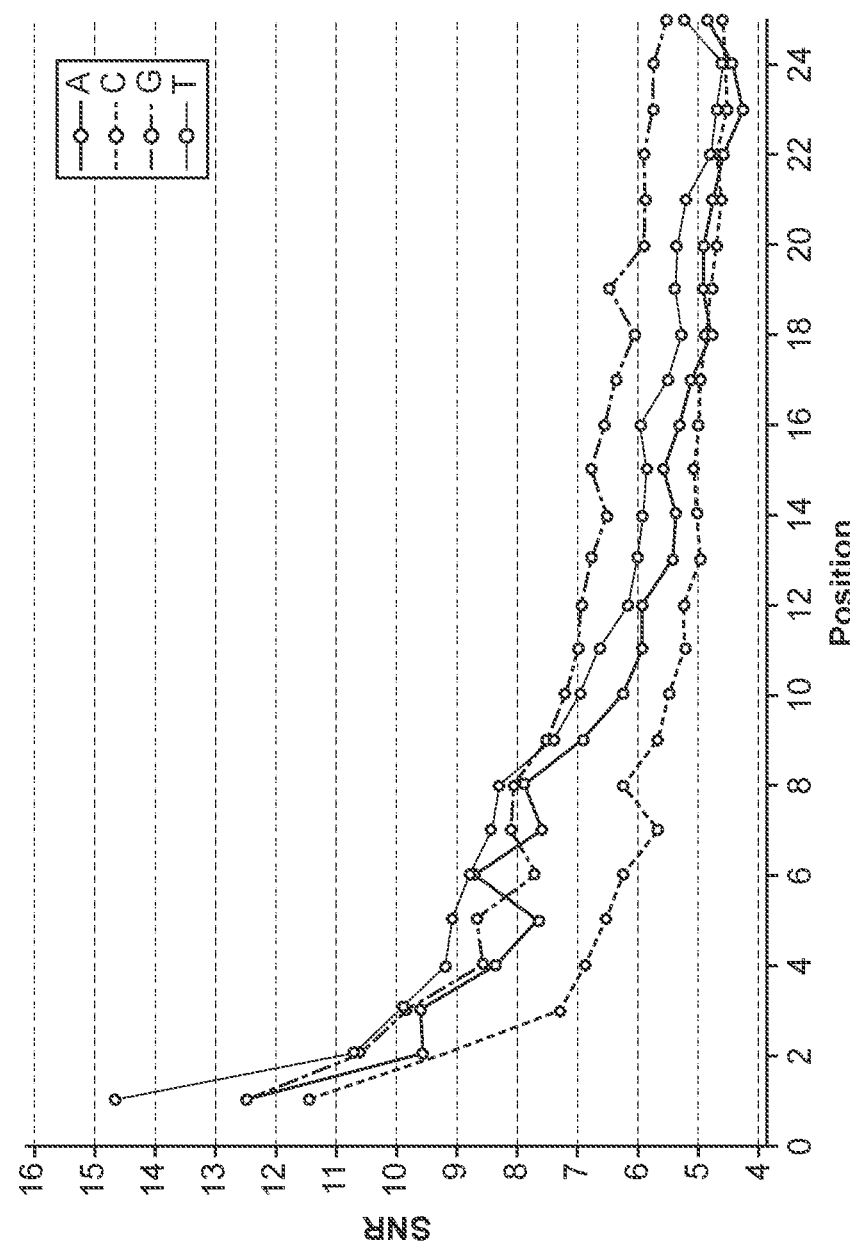

FIGS. 12A and 12B show the Rho and signal to noise ratio (SNR) for each base at each sequencing cycle. TABLE 8 shows the number of DNBs read as well as mapping and error rates when compared to a reference *E. coli* genome.

These data, including the Rho of intensities and SNR from the successful base calling report demonstrates that multiple cycles of DNA sequencing can be carried out using unlabeled reversible terminators and antibodies that bind the blocking group and base.

TABLE 8

| Total Reads (M) | 0.57 |
|---|---|
| >Q30% | 73.84 |
| Mapping Rate % | 88.3 |
| AvgErrorRate % | 1.58 |

11.10 Example 10: Differently Labeled Antibody Sets Give Comparable Results

TABLES 9 and 10 show (Top signal), Rho (background and cross-talk subtracted signal), background signal and signal-to-noise ratio (SNR) values obtained with staining of non-labeled reversible terminators on *E. coli* genomic DNA using directly labeled anti-azidomethyl-base antibodies. This experiment was performed on a BGISEQ-500 flow-cell array with an *E. coli* genomic DNA library and scanned on a BGISEQ-500 DNA sequencer. Primers were hybridized onto the immobilized DNBs and extended in the presence of all four non-labeled nucleotide 3'-azidomethyl RTs (dATP, dCTP, dGTP, dTTP) at 1 µM each concentration for 2 min at 35° C. using BG9 polymerase. After incorporation and washing to remove unincorporated nucleotides, the incorporated 3'-azidomethyl-base nucleotides were detected simultaneously by incubating all four labeled anti-3'-azidomethyl-base antibodies (Antibody Set 1) at the concentrations shown (e.g., "@30" means 30 ug/mL) for two sequential incubations of two minutes each at 35° C.

As second array was probed using an Antibody Set 2. Antibody Set 2 comprises the same antibody preparations but the antibodies are labeled differently. TABLE 10 shows signal after applying Antibody Set 2. The data demonstrate that signal and SNR values are suitable for basecalling analysis independent of the identity of the directly labeled fluorophore.

TABLE 9

| Stained Using Antibody Set 1 and Color Set 1 | | | | |
|---|---|---|---|---|
| | A @ 30* AF532 | C @ 80 IF700 | G @ 30 Cy5 | T @ 50 RoxTra |
| Top | 4567 | 2538 | 2698 | 3545 |
| Rho | 3721 | 1867 | 1905 | 3335 |
| back | 353 | 417 | 215 | 432 |
| SNR | 12.8 | 8.8 | 12 | 12.8 |

*Antibody specificity and concentration (mg/mL)

TABLE 10

| Stained Using Antibody Set 2 and Color Set 2 | | | | |
| --- | --- | --- | --- | --- |
| | G @ 30 AF532 | T @ 50 IF700 | A @ 30 Cy5 | C @ 80 RoxTra |
| Top | 4954 | 1712 | 1647 | 4348 |
| Rho | 4004 | 1395 | 1165 | 3844 |
| back | 305 | 320 | 162 | 414 |
| SNR | 13.5 | 11.5 | 12.7 | 14.8 |

11.11 Example 11: Removal of Anti-NLRT Antibody without Removing 3' Blocking Group As discussed elsewhere herein, antibody removal (disassociation from primer extension product) can be decoupled from the cleavage and removal of the 3' blocking group, TABLE 11 shows results of an experiment in which antibody was removed by specific competition. Primer extension was performed on a DNB array comprising an *E. coli* library using four non-labeled 3'-azidomethyl-base nucleotides. Staining was simultaneously incubating all four anti-3'-azidomethyl-base antibodies directly labeled with the Color Set 1 fluorophores (see Example 10). Specific competition was used to remove the detecting affinity reagents by incubating in the presence of 20 μM free antigen (3'-O-azidomethyl-2'-deoxyguanine, deoxyadenine, deoxycytosine, deoxythymine, each in triphosphate form) at 57° C. for 2 min in 50% WB1, 50% Ab buffer. The Ab removal procedure was (1) WB1, 55° C.; (2) removal solution; (3) WB1, 20° C.; (4) WB2; (5) SRE. WB1: NaCl 0.75 M, sodium citrate 0.075M, Tween 20 0.05%, pH 7.0; WB2 NaCl 50 mM, Tris-HCl pH9 50 mM, Tween 20 0.05%, EDTA 1 mM. pH 9.0; SRE NaCl 400 mM, Tris HCl pH7 1000 mM, Sodium L ascorbate 100 mM, Tween 20 0.05%, pH 7.0.

Data shows that signal and SNR are significantly reduced, indicating the removal of a majority of affinity detection reagents from the DNB array.

TABLE 11

| Labeled Antibody Removed | | | | |
| --- | --- | --- | --- | --- |
| | G-AF532 | T-IF700 | A-Cy5 | C-ROXtra |
| Before antibody removal: | | | | |
| Top | 2577 | 1708 | 1557 | 2274 |
| Rho | 2071 | 1396 | 1154 | 1987 |
| back | 234 | 407 | 243 | 340 |
| SNR | 12.1 | 7.9 | 7.8 | 11.7 |
| After antibody removal | | | | |
| Top | 355 | 577 | 419 | 511 |
| Rho | 383 | 516 | 321 | 529 |
| back | 191 | 302 | 153 | 272 |
| SNR | 3.2 | 2.1 | 2.2 | 2.9 |

11.12 Example 12: Removal of Anti-NLRT Antibody and Reprobing in Multiple Cycles of Sequencing The Example describes a process in which (1) the identity of a base at a first position is determined by detecting the binding by a first primary antibody specific for the base and 3' blocking group; (2) removing the first primary antibody without removing the 3' blocking group; (3) reprobing the same position using a second primary antibody specific for the base and 3' blocking group. The results of these experiments are summarized in TABLE 12.

TABLE 12 Illustrates an improved DNA sequence identity mapping rate when two independent reads from different fluorescent color combinations (as described in Example 10) are combined for each position of the nascent sequencing-by-synthesis strand for a total of 20 positions read. "Odd indep" represents the initial read in "conventional colors" for each sequencing position. "Even indep" represents the subsequent read in "alternate colors" after removal by specific competition using the procedure outlined in TABLE 12. "Combo" represents the result of comparing each of the two independent reads and weighting the result to the higher intensity and therefore higher confidence value of the two reads. Results show significantly higher mapping rates and significantly lower mismatch rates when the two independent reads are combined using this technique.

TABLE 12

| | Even Indep | Odd Indep | Even Wins Combo | Odd Wins Combo |
| --- | --- | --- | --- | --- |
| Number of point mutations | 26921.06 | 10992.38 | 7023.389 | 6535.383 |
| Number of indels | 220.3288 | 50.29348 | 41.78804 | 40.59239 |
| Mapping Rate | 82.78% | 95.23% | 96.30% | 96.36% |
| Total Readlength (mapping yield) | 604945.5 | 695260.7 | 702350.5 | 702764.2 |
| Average Readlength | 20 | 20 | 20 | 20 |
| Input Dnb Count | 36452.47 | 36452.47 | 36452.47 | 36452.47 |
| Mapped Dnb Count | 30247.28 | 34763.04 | 35117.53 | 35138.21 |
| Mismatch Rate | 4.52% | 1.67% | 1.02% | 0.95% |
| Uniquely Mapped Count | 28985.11 | 33533.36 | 33899.15 | 33922.32 |
| Uniquely Mapped Mismatch Rate | 4.47% | 1.65% | 1.01% | 0.94% |
| Indel Proportion | 0.04% | 0.01% | 0.01% | 0.01% |
| Concordant Yield Percent | 95.45% | 98.33% | 98.97% | 99.04% |
| Concordant Yield (bp) | 577804.2 | 684218 | 695285.4 | 696188.3 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

We claim:

1. A method for identifying a nucleobase of a non-labeled reversible terminator (NLRT) deoxyribonucleotide incorporated at a 3' terminus of a primer extension product, wherein the NLRT deoxyribonucleotide comprises a nucleobase, a sugar moiety, and a cleavable blocking group, said method comprising
  (a) combining (i) the primer extension product including the incorporated NLRT deoxyribonucleotide and (ii) a first affinity reagent that binds to the incorporated NLRT deoxyribonucleotide, wherein the first affinity reagent binds to the nucleobase, the cleavable blocking group, or both, and
  (b) detecting binding of the first affinity reagent to the incorporated NLRT deoxyribonucleotide, wherein binding of the first affinity reagent identifies a nucleobase associated with the incorporated NLRT deoxyribonucleotide.

2. A method for identifying a nucleobase of a non-labeled reversible terminator NLRT deoxyribonucleotide at a 3' terminus of a primer extension product, wherein the NLRT deoxyribonucleotide comprises a nucleobase, a sugar moiety, and a cleavable blocking group, said method comprising
  (a) producing a primer extension product comprising a NLRT deoxyribonucleotide incorporated at the 3' terminus of the primer extension product, wherein the primer extension product is base paired to a DNA template immobilized on a substrate;
  (b) removing the cleavable blocking group of the NLRT deoxyribonucleotide incorporated at the 3' terminus of the primer extension product to produce a primer extension product comprising a 3'-OH moiety;
  (c) combining the primer extension product produced in step (b) with a first affinity reagent, wherein the first affinity reagent binds the nucleobase and the 3'-OH moiety; and
  (d) detecting binding of the first affinity reagent in step (c), wherein binding of the first affinity reagent identifies the nucleobase of the incorporated NLRT deoxyribonucleotide.

3. A method for performing a sequencing-by-synthesis reaction, said method comprising the steps of:
  (a) providing a plurality of immobilized template nucleic acids comprising a plurality of different sequences;
  (b) annealing oligonucleotide primers to the plurality of immobilized template nucleic acids, wherein the oligonucleotide primers hybridize to predetermined positions on the plurality of immobilized template nucleic acids;
  (c) carrying out multiple cycles of steps (i)-(iv):
    (i) combining the plurality of immobilized template nucleic acids and primers annealed thereto with a polymerase and four reversible terminator deoxyribonucleotide triphosphates (dNTPs), each of said four reversible terminator dNTPs comprising a nucleobase (N), a sugar moiety, and a cleavable blocking group,
    wherein N is adenine (A) or an analog thereof (A'), guanine (G) or an analog thereof (G'), thymine (T) or an analog thereof (T'), and cytosine (C) or an analog thereof (C'),
    wherein at least one of said four reversible terminator dNTPs is a non-labeled reversible terminator (NLRT),
    under conditions in which a plurality of the oligonucleotide primers are extended by incorporation of a single reversible terminator dNTP to produce a plurality of primer extension products each comprising one of four incorporated reversible terminator dNTPs at a 3' terminus, some of which comprise A or A' incorporated at the 3' terminus, some of which comprise T or T' incorporated at the 3' terminus, some of which comprise G or G' incorporated at the 3' terminus, and some of which comprise C or C' incorporated at the 3' terminus;
    (ii) contacting the plurality of primer extension products with one or more first affinity reagents under conditions in which each of said one or more first affinity reagents binds to only one of the four incorporated reversible terminator dNTPs, wherein the one or more first affinity reagents bind to the nucleobase, the cleavable blocking group, or a combination thereof, of said one of four incorporated reversible terminator dNTPs;
    (iii) detecting the binding of the one or more first affinity reagents, wherein the binding of a first affinity reagent to a primer extension product comprising an incorporated reversible terminator dNTPs identifies the nucleobase complementary to the nucleobase of the incorporated reversible terminator dNTPs; and
    (iv) removing the cleavable blocking groups of the incorporated reversible terminator dNTPs.

4. A kit comprising (i) a first affinity reagent that binds a first non-labeled reversible terminator (NLRT) deoxyribonucleotide comprising a first naturally occurring nucleobase or analog thereof, wherein the first affinity reagent is an antibody or aptamer, and (ii) a second affinity reagent that binds a second NLRT deoxyribonucleotide comprising a second naturally occurring nucleobase or analog thereof, wherein the second affinity reagent is an antibody or aptamer, and wherein the first NLRT and the second NLRT are different.

5. A method for detecting a non-labeled reversible terminator (NLRT) deoxyribonucleotide incorporated at a 3' terminus of a primer extension product, wherein the NLRT deoxyribonucleotide comprises a nucleobase, a sugar moiety, and a cleavable blocking group, said method comprising:
  (a) providing the primer extension product comprising the incorporated NLRT deoxyribonucleotide;
  (b) combining the primer extension product from (a) with a first affinity reagent that binds to the incorporated NLRT deoxyribonucleotide, wherein the first affinity reagent binds to the nucleobase, the cleavable blocking group, or both, or to the nucleobase and a 3'-OH moiety of the primer extension product; and
  (c) detecting binding of the first affinity reagent to the incorporated NLRT deoxyribonucleotide,
  wherein the first affinity reagent is an antibody, aptamer, or affimer.

6. The method of claim 5, wherein the first affinity reagent is detectably labeled with a fluorescent dye.

7. The method of claim 5, wherein the first affinity reagent is an antibody detectably labeled with a luciferase.

8. The method of claim 5, wherein detecting binding of the first affinity reagent comprises contacting the first affinity reagent with a detectably labeled secondary affinity reagent that specifically binds the first affinity reagent, wherein said contacting occurs before or after step (b).

9. The method of claim 5, wherein the nucleobase is a naturally occurring nucleobase selected from adenine, guanine, thymine, and cytosine.

10. The method of claim 5, wherein the nucleobase is a nucleobase analog selected from an adenine analog with a molecular weight no greater than 185, a guanine analog with a molecular weight no greater than 201, a thymine analog with a molecular weight no greater than 176, and a cytosine analog with a molecular weight no greater than 161.

11. The method of claim 5, wherein the first affinity reagent discriminates
a) a 3' terminal nucleotide comprising adenine (A) from a 3' terminal nucleotide comprising guanine (G), thymine (T), or cytosine (C);
b) a 3' terminal nucleotide comprising G from a 3' terminal nucleotide comprising T, C, or A;
c) a 3' terminal nucleotide comprising T from a 3' terminal nucleotide comprising G, C, or A; or
d) a 3' terminal nucleotide comprising C from a 3' terminal nucleotide comprising G, T, or A.

12. The method of claim 5, wherein the cleavable blocking group is selected from the group consisting of allyl, azidomethyl, aminoalkoxyl, 2-cyanoethyl, substituted alkyl, unsubstituted alkyl, substituted alkenyl, unsubstituted alkenyl, substituted alkynyl, unsubstituted alkynyl, substituted heteroalkyl, unsubstituted heteroalkyl, substituted heteroalkenyl, unsubstituted heteroalkenyl, substituted heteroalkynyl, unsubstituted heteroalkynyl, allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl, amino, cyanoethenyl, cyanoethyl, alkoxy, acyl, methoxymethyl, aminoxyl, carbonyl, nitrobenzyl, coumarinyl, and nitronaphthalenyl.

13. The method of claim 1, wherein detecting binding of the first affinity reagent comprises:
(i) detecting a fluorescence signal from a fluorescent dye attached to the first affinity reagent or from a fluorescent dye attached to a secondary affinity reagent that binds the first affinity reagent, or
(ii) detecting a chemiluminescence signal produced by an enzyme attached to the first affinity reagent or an enzyme attached to a secondary affinity reagent that binds the first affinity reagent.

14. The method of claim 13, wherein the detecting in step (b) comprises detecting a chemiluminescence signal produced by an enzyme attached to the first affinity reagent or an enzyme attached to the secondary affinity reagent, and wherein the enzyme is a luciferase.

15. The method of claim 1, further comprising producing the primer extension B product prior to Step (a), wherein the primer extension product is base paired to a template DNA immobilized on a substrate.

16. The method of claim 15, wherein the substrate is an ordered DNA array used for massively parallel sequencing.

17. The method of claim 16, wherein the ordered DNA array comprises template DNA molecules immobilized at different locations on the ordered DNA array, and wherein said template DNA molecules are DNA nanoballs or are clonal populations of amplicons produced using bridge amplification.

18. The method of claim 1, wherein the first affinity reagent binds to the nucleobase and the cleavable blocking group.

19. The method of claim 1, wherein the first affinity reagent is an antibody.

20. The method of claim 1, wherein the first affinity reagent is an aptamer.

21. The method of claim 1, further comprising removing the first affinity reagent from the primer extension product after Step (b).

22. The method of claim 21, further comprising removing the cleavable blocking group after Step (b).

23. The method of claim 21, wherein the first affinity reagent is removed without removing the cleavable blocking group.

24. The method of claim 2, wherein the substrate is an ordered DNA array used for massively parallel sequencing.

25. The method of claim 2, wherein the first affinity reagent is an antibody.

26. The method of claim 2, wherein the first affinity reagent is an aptamer.

27. The method of claim 3, wherein all of the four reversible terminator dNTPs are unlabeled.

28. The method of claim 27, wherein at least two of the reversible terminator dNTPs comprise different cleavable blocking groups.

29. The method of claim 28, wherein at least one of the cleavable blocking groups is azidomethyl.

30. The method of claim 3, wherein the first affinity reagents are antibodies, aptamers, or a combination of antibodies and aptamers.

31. The method of claim 30, wherein the first affinity reagents are single chain antibodies or fusion proteins comprising a single-chain Fv fragment domain and a luciferase domain.

32. The kit of claim 4, wherein the first and second NLRT deoxyribonucleotides comprise naturally occurring nucleobases.

33. The kit of claim 4, the kit further comprising (iii) a third affinity reagent that binds a third NLRT deoxyribonucleotide comprising a third naturally occurring nucleobase or analog thereof, wherein the first, second and third naturally occurring nucleobases or analogs thereof are different from each other.

34. The kit of claim 33, the kit further comprising (iv) a fourth affinity reagent that binds a fourth NLRT deoxyribonucleotide comprising a fourth naturally occurring nucleobase or analog thereof, wherein the first, second, third and fourth naturally occurring nucleobases or analogs thereof are different from each other.

35. The kit of claim 33, wherein each of said first, second, and third affinity reagents comprises a detectable label.

36. The kit of claim 35, wherein the detectable label is selected from the group consisting of a dye(s) that produces a fluorescence signal and an enzyme(s) that produces a chemiluminescence signal.

37. The kit of claim 36, wherein the enzyme(s) that produce a chemiluminescence signal is a luciferase.

38. The kit of claim 35, wherein:
(i) each of said first, second, and third affinity reagents comprises a different detectable label; or (ii) each of said first, second, and third affinity reagents comprises the same detectable label in different amounts or intensities from each other; or (iii) the first affinity reagent comprises a first detectable label, the second affinity reagent comprises a second detectable label that is different from the first detectable label, and the third affinity reagent comprises both the first detectable label and the second detectable label.

39. The kit of claim 33, comprising a first secondary affinity reagent, a second secondary affinity reagent, and a third secondary affinity reagent that bind the first, second and third affinity reagents, respectively, wherein the first, second and third secondary affinity reagents each comprise a detectable label.

40. The kit of claim 39, wherein:

(i) each of the first, second, and third secondary affinity reagents comprises a different detectable label; or (ii) each of the first, second, and third secondary affinity reagents comprises the same detectable label in different amounts or intensities from each other; or (iii) the first secondary affinity reagent comprises a first detectable label, the second secondary affinity reagent comprises a second detectable label that is different from the first detectable label, and the third secondary affinity reagent comprises both the first detectable label and the second detectable label.

41. The kit of claim 39, wherein the detectable label is selected from the group consisting of a dye(s) that produces a fluorescence signal and an enzyme(s) that produces a chemiluminescence signal.

42. The kit of claim 41, wherein the enzyme(s) that produce a chemiluminescence signal is a luciferase.

43. The kit of claim 4, wherein the first and second affinity reagents are antibodies.

44. The kit of claim 4, wherein the first and second affinity reagents are aptamers.

45. The kit of claim 4, further comprising one or more NLRT deoxyribonucleotides.

46. The kit of claim 45, wherein the kit comprises two or more NLRT deoxyribonucleotides, and wherein at least two of the NLRT deoxyribonucleotides comprise different cleavable blocking groups.

47. The kit of claim 46, wherein one of the cleavable blocking groups is azidomethyl.

\* \* \* \* \*

UNITED STATES PATENT AND TRADEMARK OFFICE
CERTIFICATE OF CORRECTION

PATENT NO. : 11,788,138 B2  
APPLICATION NO. : 17/084482  
DATED : October 17, 2023  
INVENTOR(S) : Radoje Drmanac et al.

Page 1 of 1

It is certified that error appears in the above-identified patent and that said Letters Patent is hereby corrected as shown below:

In the Claims

In Column 67, Line 33:  
In Claim 2, delete "NLRT" and  
Insert -- (NLRT) --.

In Column 69, Line 63:  
In Claim 15, delete "extension B" and  
Insert -- extension --.

Signed and Sealed this  
Twenty-eighth Day of November, 2023

Katherine Kelly Vidal  
*Director of the United States Patent and Trademark Office*